(12) United States Patent
Fineman et al.

(10) Patent No.: US 8,329,648 B2
(45) Date of Patent: Dec. 11, 2012

(54) METHODS FOR TREATING DIABETES AND REDUCING BODY WEIGHT

(75) Inventors: Mark Fineman, San Diego, CA (US); Leigh MacConell, San Diego, CA (US); Kristin Taylor, San Diego, CA (US)

(73) Assignee: Amylin Pharmaceuticals, LLC, San Diego, CA (US)

(*) Notice: Subject to any disclaimer, the term of this patent is extended or adjusted under 35 U.S.C. 154(b) by 0 days.

(21) Appl. No.: 13/084,757

(22) Filed: Apr. 12, 2011

(65) Prior Publication Data

US 2011/0245162 A1 Oct. 6, 2011

Related U.S. Application Data

(63) Continuation of application No. 12/064,216, filed as application No. PCT/US2006/032354 on Aug. 18, 2006, now abandoned.

(60) Provisional application No. 60/779,216, filed on Mar. 3, 2006, provisional application No. 60/709,604, filed on Aug. 19, 2005.

(51) Int. Cl.
*A61P 3/08* (2006.01)
*A61P 3/10* (2006.01)
*A61K 38/26* (2006.01)

(52) U.S. Cl. ............ 514/6.8; 514/4.8; 514/6.9; 514/7.2

(58) Field of Classification Search .................. None
See application file for complete search history.

(56) References Cited

U.S. PATENT DOCUMENTS

| | | | |
|---|---|---|---|
| 5,424,286 A | 6/1995 | Eng | |
| 6,479,065 B2 | 11/2002 | Jaworowicz et al. | |
| 6,495,164 B1 | 12/2002 | Ramstack et al. | |
| 6,667,061 B2 | 12/2003 | Ramstach et al. | |
| 6,824,822 B2 | 11/2004 | Rickey et al. | |
| 6,858,576 B1 | 2/2005 | Young et al. | |
| 6,872,700 B1 | 3/2005 | Young et al. | |
| 6,902,744 B1 | 6/2005 | Kolterman et al. | |
| 6,924,264 B1 | 8/2005 | Prickett et al. | |
| 6,956,026 B2 | 10/2005 | Bhavsar et al. | |
| 7,223,440 B2 | 5/2007 | Rickey et al. | |
| 7,259,233 B2 | 8/2007 | Dodd et al. | |
| 7,456,254 B2 | 11/2008 | Wright et al. | |
| 7,563,871 B2 | 7/2009 | Wright et al. | |
| 7,741,269 B2 | 6/2010 | Bhavsar et al. | |
| 2003/0036504 A1 | 2/2003 | Kolterman et al. | |
| 2003/0087820 A1* | 5/2003 | Young et al. ................ | 514/12 |
| 2003/0087821 A1 | 5/2003 | Beeley et al. | |
| 2004/0121009 A1* | 6/2004 | Dasch et al. ............. | 424/468 |
| 2006/0183677 A1 | 8/2006 | Young et al. | |
| 2008/0057131 A1 | 3/2008 | Dasch et al. | |

FOREIGN PATENT DOCUMENTS

| | | |
|---|---|---|
| WO | WO 00/41546 | 7/2000 |
| WO | WO 2004/056317 | 7/2004 |
| WO | WO 2005/041873 | 5/2005 |
| WO | WO 2005/058252 | 6/2005 |
| WO | WO 2005/102293 | 11/2005 |

OTHER PUBLICATIONS

DeFronzo et al., Diabetes Care, 28: 1092-1100, 2005.*
Buse et al., Diabetes Care, 27: 2628-2635, 2004.*
Adis International, *Drugs in R&D* 5(1):35-40 (2004) *Exenatide: AC2993, AC002993, AC2993A, Exendin 4, LY2148568.*
Blase et al., *J. Clin. Cpharmacol.* 45:570-577 (2005): *Pharmacokinetics of an Oral Drug (Acetaminophen) Administered at Various Tiomes in Relation to Subcutaneous Injection of Exenatide (Exendin-4) in Healthy Subjects.*
Amylin Pharmaceuticals, Inc. Press Release dated Nov. 2, 2004: *Exenatide LAR data support initiation of phase 2 multi-dose study in 2005.*
Buse et al., *Diabetes Care* 27(11):2628-2635 (Nov. 2004): *Effects of exenatide (exendin-4) on glycemic control over 30 weeks in sulfonylurea-treated patients with type 2 diabetes.*
Calera et al., *Clinical Ther.* 27(2):210 (2005): *A Randomized, Open Label, Crossover Study Examining the Effect of Injection Site on Bioavailability of Exenatide (Synthetic Exendin-4).*
Gedulin et al., *Diabetologia* 48(7):1380-1385 (Jul. 2005), XP002431948 ISSN: 00123-186X abstract, figure 1: *Dose-Response for glucaemic and metabolic changes 28 days after single injection of long-acting release exenatide in diabetic fatty Zucker Rats.*
Kolterman et al., *Am. J. Health-Syst. Pharm* 62:173 (2005): *Pharmacokinetics, Pharmacodynamics, and safety of exenatide in patients with type 2 diabetes mellitus.*

* cited by examiner

*Primary Examiner* — Gyan Chandra

(57) ABSTRACT

Methods for reducing body weight, altering body composition, treating diabetes, reducing $HbA_{1c}$ and reducing average daily blood glucose by the use of exendins, exendin agonists or exendin analog agonists are provided.

20 Claims, 6 Drawing Sheets

US 8,329,648 B2

METHODS FOR TREATING DIABETES AND REDUCING BODY WEIGHT

CROSS REFERENCE TO RELATED APPLICATIONS

This application is a continuation of U.S. application Ser. No. 12/064,216 filed Oct. 27, 2008, now abandoned, which is a §371 of PCT/US2006/32354 filed Aug. 18, 2006, which claims priority to U.S. Application No. 60/779,216, filed Mar. 3, 2006, and U.S. Application No. 60/709,604 filed Aug. 19, 2005, each of which is incorporated by reference in its entirety.

FIELD OF THE INVENTION

The present invention relates to the fields of medicine, health and nutrition. More particularly, the present invention relates to methods and compositions for treating diabetes and reducing body weight or altering body composition in a subject.

BACKGROUND

Obesity is a condition that affects millions of Americans. Recent statistics from the Center for Disease Control ("CDC") estimate that approximately 65% of all Americans are overweight or obese and it is generally believed that these numbers are increasing. Being obese or overweight may substantially increase the risk of morbidity from hypertension; dyslipidemia; type 2 diabetes; coronary heart disease; stroke; gallbladder disease; osteoarthritis; sleep apnea and respiratory problems; and endometrial, breast, prostate, and colon cancers. Higher body weights are also associated with increases in all-cause mortality. Furthermore, being obese or overweight may cause a person to have negative self-image about him or her self.

In humans, patients who are overweight or obese are considered those with a Body Mass Index (BMI) of equal to or greater than 25. BMI is a common measure expressing the relationship (or ratio) of weight-to-height. It is a mathematical formula in which a person's body weight in kilograms is divided by the square of his or her height in meters (i.e., $wt/(ht)^2$). Individuals with a BMI of 25 to 29.9 are considered overweight, while individuals with a BMI of 30 or more are considered obese.

According to the NIH Clinical Guidelines on the Identification, Evaluation, and Treatment of Overweight and Obesity in Adults, all adults (aged 18 years or older) who have a BMI of 25 or more are considered at risk for premature death and disability as a consequence of being overweight or obese. These health risks increase even more as the severity of an individual's obesity increases.

For these reasons, there is an enormous interest in treating obesity. Existing therapies include standard diets and exercise, very low calorie diets, behavioral therapy, pharmacotherapy involving appetite suppressants, thermogenic drugs, food absorption inhibitors, mechanical devices such as jaw wiring, waist cords and balloons, and surgery, such as gastric bypass. Jung and Chong, *Clinical Endocrinology*, 35:11-20 (1991); Bray, *Am. J. Clin. Nutr.*, 55:538 S-544S (1992). However, additional methods for reducing weight or treating obesity are still needed.

In general, however, while loss of body fat is desired, loss of lean body mass and in particular protein, is not. Lean body mass is comprised of muscle, vital organs, bone, connective and other non-fatty tissues in the body. Lean body mass is 50-60% muscle by weight, with the majority of the muscle being skeletal muscle. Lean body mass is highly active, metabolically and physiologically, and it is believed that loss of lean body mass is deleterious to the health of an individual. An increase in lean body mass helps increase body metabolism and so aids in weight loss and the maintenance of any weight reduction. Thus, during the process of weight loss, it is desirable that the loss of lean body mass be prevented or minimized.

Caloric restriction, regardless of its form, is often associated with catabolism of body protein resulting in a negative nitrogen balance and a loss of lean body mass. Protein supplemented diets have been used as a means of lessening nitrogen loss during caloric restriction. Protein-sparing modified fasting has been reported to be effective in weight reduction in adolescents; however, these diets may produce only moderate nitrogen sparing. Lee et al., *Clin. Pediatr.*, 31:234-236, 1992.

Diabetes mellitus is a serious metabolic disease that is defined by the presence of chronically elevated levels of blood glucose (hyperglycemia). This state of hyperglycemia is the result of a relative or absolute lack of activity of the peptide hormone, insulin. Insulin is produced and secreted by the β cells of the pancreas. Insulin is reported to promote glucose utilization, protein synthesis, and the formation and storage of carbohydrate energy as glycogen. Glucose is stored in the body as glycogen, a form of polymerized glucose, which may be converted back into glucose to meet metabolism requirements. Under normal conditions, insulin is secreted at both a basal rate and at enhanced rates following glucose stimulation, all to maintain metabolic homeostasis by the conversion of glucose into glycogen.

The term diabetes mellitus encompasses several different hyperglycemic states. These states include Type I (insulin-dependent diabetes mellitus or IDDM) and Type II (non-insulin dependent diabetes mellitus or NIDDM) diabetes. The hyperglycemia present in individuals with Type I diabetes is associated with deficient, reduced, or nonexistent levels of insulin which are insufficient to maintain blood glucose levels within the physiological range. Treatment of Type I diabetes involves administration of replacement doses of insulin, generally by a parenteral route. The hyperglycemia present in individuals with Type II diabetes is initially associated with normal or elevated levels of insulin; however, these individuals are unable to maintain metabolic homeostasis due to a state of insulin resistance in peripheral tissues and liver and, as the disease advances, due to a progressive deterioration of the pancreatic β cells which are responsible for the secretion of insulin. Thus, initial therapy of Type II diabetes may be based on diet and lifestyle changes augmented by therapy with oral hypoglycemic agents such as sulfonylureas. Insulin therapy is often required, however, especially in the latter states of the disease, in order to produce some control of hyperglycemia and minimize complications of the disease.

Exendins are peptides that are found in the saliva of the Gila-monster, a lizard endogenous to Arizona, and the Mexican Beaded Lizard. Exendin-3 is present in the saliva of *Heloderma horridum*, and exendin-4 is present in the saliva of *Heloderma suspectum* (Eng., J., et al., *J. Biol. Chem.*, 265: 20259-62, 1990; Eng., J., et al., *J. Biol. Chem.*, 267:7402-05, 1992). The exendins have some amino acid sequence similarity to several members of the glucagon-like peptide family, with the highest amino acid identity, 53%, being to GLP-1 (Goke, et al., *J. Biol. Chem.*, 268:19650-55, 1993).

Exendin-4 is a potent GLP-1 receptor agonist in vitro. The peptide also stimulates somatostatin release and inhibits gastrin release in isolated stomachs (Goke, et al., *J. Biol. Chem.*, 268:19650-55, 1993; Schepp, et al., *Eur. J. Pharmacol.*, 69:183-91, 1994; Eissele, et al., *Life Sci.*, 55:629-34, 1994). Exendin-3 and exendin-4 were found to be GLP-1 receptor agonists in stimulating cAMP production in, and amylase release from, pancreatic acinar cells (Malhotra, R., et al., *Regulatory Peptides*, 41:149-56, 1992; Raufman, et al., *J. Biol. Chem.*, 267:21432-37, 1992; Singh, et al., *Regulatory Peptides.*, 53:47-59, 1994). The use of the insulinotropic activities of exendin-3 and exendin-4 for the treatment of diabetes mellitus and the prevention of hyperglycemia has been proposed (Eng, U.S. Pat. No. 5,424,286). Twice daily and sustained administration of exendins has been proposed (U.S. Pat. No. 6,924,264 and U.S. Pat. App. No. 20040053819).

The need exists, therefore, for methods to reduce body weight and in particular to reduce weight in subjects suffering from diabetes. Of particular interest are methods of reducing body weight that spare lean body mass. Described, herein are methods for meeting these needs.

SUMMARY

Provided in one embodiment, is a method for reducing body weight comprising administering to a subject in need of reducing body weight, or a subject who desires to reduce their body weight, a formulation comprising an amount of at least one exendin, exendin agonist or exendin analog agonist sufficient to maintain an average plasma concentration of the exendin, exendin agonist or exendin analog agonist of at least about 50 µg/ml for at least about 12 hours, at least about 1 day, at least about 2 days, at least about 3 days, at least about 1 week, at least about 2 weeks, at least about 3 weeks, at least about 1 month, at least about 3 months, or at least about 6 months. In other embodiments, the average plasma concentration of the exendin, exendin agonist, or exendin analog agonist is from about 25 pg/ml to about 600 pg/ml, from about 170 pg/ml to about 600 pg/ml or from about 170 pg/ml to about 350 pg/ml. In additional embodiments, the average plasma concentration is at least about 25 pg/ml, at least about 65 pg/ml, at least about 75 pg/ml, at least about 85 pg/ml, at least about 100 pg/ml, at least about 150 pg/ml, at least about 170 pg/ml, at least about 175 pg/ml, at least about 200 pg/ml, at least about 225 pg/ml at least about 250 pg/ml, at least about 300 pg/ml, at least about 350 pg/ml, at least about 400 pg/ml, at least about 450 pg/ml, at least about 500 pg/ml at least about 550 pg/ml, or at least about 600 pg/ml. In still other embodiments, the average plasma concentration of the exendin, exendin agonist or exendin analog agonist is greater than 40 pmoles/liter, greater than 50 pmoles/liter, greater than 60 pmoles/liter, greater than 70 pmoles/liter, greater than 80 pmoles/liter, greater than 90 pmoles/liter, greater than 100 pmoles/liter, greater than 110 pmoles/liter, greater than 120 pmoles/liter, greater than 130 pmoles/liter, greater than 140 pmoles/liter, or greater than 150 pmoles/liter. In still further embodiments, the average plasma concentration of the exendin, exendin agonist or exendin analog agonist is greater than 40 pmoles/liter but less than 150 pmoles/liter or greater than 40 pmoles/liter but less than 80 pmoles/liter. In one embodiment, the exendin, exendin agonist or exendin analog agonist is exendin-4. In other embodiments, the concentration of the exendin, exendin agonist or exendin analog agonist is the concentration of an exendin, exendin agonist or exendin analog agonist that results in a biological or therapeutic effect, e.g. weight reduction, equivalent to that observed with a given concentration of exendin-4. In further embodiments, the subject suffers from diabetes or impaired glucose tolerance.

Another embodiment provides a method for reducing body weight in a subject comprising administering to a subject in need of reducing body weight, or desirous of reducing body weight an amount of a formulation containing at least one exendin, exendin analog or exendin analog agonist, sufficient to maintain a minimum plasma concentration of the exendin, exendin agonist or exendin analog agonist of at least about 50 pg/ml for at least about 12 hours, at least about 1 day, at least about 2 days, at least about 3 days, at least about 1 week, at least about 2 weeks, at least about 3 weeks, at least about 1 month, at least about 3 months, or at least about 6 months. In additional embodiments, the plasma concentration of the at least one exendin, exendin agonist or exendin analog agonist is maintained at greater than or equal to about 25 pg/ml, greater than or equal to about 65 pg/ml, greater than or equal to about 75 pg/ml, greater than or equal to about 85 pg/ml, greater than or equal to about 100 pg/ml, greater than or equal to about 150 pg/ml, greater than or equal to about 170 pg/ml, greater than or equal to about 175 pg/ml, greater than or equal to about 200 pg/ml, greater than or equal to about 225 pg/ml, greater than or equal to about 250 pg/ml, greater than or equal to about 300 pg/ml, greater than or equal to about 350 pg/ml, greater than or equal to about 400 pg/ml, greater than or equal to about 450 pg/ml, greater than or equal to about 500 pg/ml, greater than or equal to about 550 pg/ml or greater than or equal to about 600 pg/ml. In other embodiments, the concentration of the exendin, exendin agonist or exendin analog agonist is between at least about 170 pg/ml and 600 pg/ml or between at least about 170 pg/ml and 350 pg/ml. In still other embodiments, the minimum plasma concentration of the exendin, exendin agonist or exendin analog agonist is greater than 40 pmoles/liter, greater than 50 pmoles/liter, greater than 60 pmoles/liter, greater than 70 pmoles/liter, greater than 80 pmoles/liter, greater than 90 pmoles/liter, greater than 100 pmoles/liter, greater than 110 pmoles/liter, greater than 120 pmoles/liter, greater than 130 pmoles/liter, greater than 140 pmoles/liter, or greater than 150 pmoles/liter. In still further embodiments, the minimum plasma concentration of the exendin, exendin agonist or exendin analog agoinsits is greater than 40 pmoles/liter, but less than 150 pmoles/liter or greater than 40 pmoles/liter but less than 80 pmoles/liter. In one embodiment, the exendin, exendin agonist or exendin analog agonist is exendin-4. In other embodiments, the concentration of the exendin, exendin agonist or exendin analog agonist is the concentration of an exendin, exendin agonist or exendin analog agonist that results in a biological or therapeutic effect, e.g. weight reduction, equivalent to that observed with a given concentration of exendin-4. In further embodiments, the subject suffers from diabetes or impaired glucose tolerance.

Further embodiments provide a method for altering body composition, for example reducing the ratio of body fat to lean tissue in an individual comprising administering to a subject in need of altering body composition, or desirous of altering body composition, an amount of a formulation containing at least one exendin, exendin analog or exendin analog agonist, sufficient to maintain either an average or a minimum plasma concentration of the exendin, exendin agonist or exendin analog agonist of at least about 50 pg/ml for at least about 12 hours, at least about 1 day, at least about 2 days, at least about 3 days, at least about 1 week, at least about 2 weeks, at least about 3 weeks, at least about 1 month, at least about 3 months, or at least about 6 months. In additional embodiments, the average or minimum plasma concentration of the at least one exendin, exendin agonist or exendin analog agonist is at least about 25 pg/ml, at least about 65 pg/ml, about 75 pg/ml, about 85 pg/ml, about 100 pg/ml, about 150 pg/ml, about 170 pg/ml, about 175 pg/ml, about 200 pg/ml, about 225 pg/ml, about 250 pg/ml, about 300 pg/ml, about 350 pg/ml, about 400 pg/ml, about 450 pg/ml, about 500 pg/ml, about 550 pg/ml, or about 600 pg/ml. In other embodiments, the average or minimum concentration of the exendin, exendin agonist or exendin analog agonist is between at least about 170 pg/ml and 600 pg/ml or between at least about 170 pg/ml and 350 pg/ml. In still other embodiments, the average or minimum plasma concentration of the exendin, exendin agonist or exendin analog agonist is greater than 40 pmoles/liter, greater than 50 pmoles/liter, greater than 60 pmoles/liter, greater than 70 pmoles/liter, greater than 80 pmoles/liter, greater than 90 pmoles/liter, greater than 100 pmoles/liter, greater than 110 pmoles/liter, greater than 120 pmoles/liter, greater than 130 pmoles/liter, greater than 140 pmoles/liter, or greater than 150 pmoles/liter. In still further embodiments, the average or minimum plasma concentration of the exendin, exendin agonist or exendin analog agonist is greater than 40 pmoles/liter but less than 150 pmoles/liter or greater than 40 pmoles/liter but less than 80 pmoles/liter. In one embodiment, the exendin, exendin agonist or exendin analog agonist is exendin-4. In other embodiments, the concentration of the exendin, exendin agonist or exendin analog agonist is the concentration of an exendin, exendin agonist or exendin analog agonist that results in a biological or therapeutic effect, e.g. alteration in body composition, equivalent to that observed with a given concentration of exendin-4. In further embodiments, the subject suffers from diabetes or impaired glucose tolerance.

Additional embodiments provide a method for treating diabetes, for example, type I, type II, or gestational diabetes, in a subject in need thereof, comprising administering to said subject an amount of a formulation containing at least one exendin, exendin analog or exendin analog agonist, sufficient to maintain either an average or minimum plasma concentration of the exendin, exendin agonist or exendin analog agonist of at least about 50 pg/ml for at least about 12 hours, at least about 1 day, at least about 2 days, at least about 3 days, at least about 1 week, at least about 2 weeks, at least about 3 weeks, at least about 1 month, at least about 3 months, or at least about 6 months. In one embodiment, the subject in need thereof is also obese or desirous or in need of reducing body weight. In additional embodiments, the average or minimum plasma concentration of the at least one exendin, exendin agonist or exendin analog agonist is at least about 25 pg/ml, at least about 65 pg/ml, about 75 pg/ml, about 85 pg/ml, about 100 pg/ml, about 150 pg/ml, 170 pg/ml, 175 pg/ml, about 200 pg/ml, about 225 pg/ml, about 250 pg/ml, about 300 pg/ml, about 350 pg/ml, about 400 pg/ml, about 450 pg/ml, about 500 pg/ml, about 550 pg/ml, or about 600 pg/ml. In other embodiments, the average or minimum concentration of the exendin, exendin agonist or exendin analog agonist is between at least about 170 pg/ml and 600 pg/ml or between at least about 170 pg/ml and 350 pg/ml. In still other embodiments, the average or minimum plasma concentration of the exendin, exendin agonist or exendin analog agonist is greater than 40 pmoles/liter, greater than 50 pmoles/liter, greater than 60 pmoles/liter, greater than 70 pmoles/liter, greater than 80 pmoles/liter, greater than 90 pmoles/liter, greater than 100 pmoles/liter, greater than 110 pmoles/liter, greater than 120 pmoles/liter, greater than 130 pmoles/liter, greater than 140 pmoles/liter, or greater than 150 pmoles/liter. In still further embodiments, the average or minimum plasma concentration of the exendin, exendin agonist or exendin analog agonist is greater than 40 pmoles/liter but less than 150 pmoles/liter or greater than 40 pmoles/liter but less than 80 pmoles/liter. In one embodiment, the exendin, exendin agonist or exendin analog agonist is exendin-4. In other embodiments, the concentration of the exendin, exendin agonist or exendin analog agonist is the concentration of an exendin, exendin agonist or exendin analog agonist that results in a biological or therapeutic effect, e.g. weight reduction, lowering fasting glucose, reducing postprandial glucose excursions, etc., equivalent to that observed with a given concentration of exendin-4.

Still another embodiment provides a method for reducing hemoglobin $A_{1C}$ ($HbA_{1C}$) in a subject in need thereof comprising administering to said subject an amount of a formulation containing at least one exendin, exendin analog or exendin analog agonist, sufficient to maintain either an average or a minimum plasma concentration of the exendin, exendin agonist or exendin analog agonist of at least about 50 pg/ml for at least about 12 hours, at least about 1 day, at least about 2 days, at least about 3 days, at least about 1 week, at least about 2 weeks, at least about 3 weeks, at least about 1 month, at least about 3 months, or at least about 6 months. In one embodiment, the subject in need thereof is also obese or desirous or need of reducing body weight. In additional embodiments, the average or sustained plasma concentration of the at least one exendin, exendin agonist or exendin analog agonist is at least about 25 pg/ml, at least about 65 pg/ml, about 75 pg/ml, about 85 pg/ml, about 100 pg/ml, about 150 pg/ml, about 170 pg/ml, about 175 pg/ml, about 200 pg/ml, about 225 pg/ml, about 250 pg/ml, about 300 pg/ml, about 350 pg/ml about 400 pg/ml, about 450 pg/ml, about 500 pg/ml, about 550 pg/ml or about 600 pg/ml. In other embodiments, the average or minimum concentration of the exendin, exendin agonist or exendin analog agonist is between at least about 170 pg/ml and 600 pg/ml or between at least about 170 pg/ml and 350 pg/ml. In still other embodiments, the average or minimum plasma concentration of the exendin, exendin agonist or exendin analog agonist is greater than 40 pmoles/liter, greater than 50 pmoles/liter, greater than 60 pmoles/liter, greater than 70 pmoles/liter, greater than 80 pmoles/liter, greater than 90 pmoles/liter, greater than 100 pmoles/liter, greater than 110 pmoles/liter, greater than 120 pmoles/liter, greater than 130 pmoles/liter, greater than 140 pmoles/liter, or greater than 150 pmoles/liter. In still further embodiments, the average or minimum plasma concentration of the exendin, exendin agonist or exendin analog agonist is greater than 40 pmoles/liter but less than 150 pmoles/liter or greater than 40 pmoles/liter but less than 80 pmoles/liter. In one embodiment, the exendin, exendin agonist or exendin analog agonist is exendin-4. In other embodiments, the concentration of the exendin, exendin agonist or exendin analog agonist is the concentration of an exendin, exendin agonist or exendin analog agonist that results in a biological or therapeutic effect, e.g. reducing $HbA_{1c}$, equivalent to that observed with a given concentration of exendin-4.

Yet another embodiment provides a means for reducing the increase in postprandial blood glucose as compared to preprandial or fasting blood glucose in subjects in need thereof, for example subjects with type I, type II or gestational diabetes, or as compared to subjects not receiving the methods, formulations or medicaments described herein, comprising administering to said subject an amount of a formulation or medicament containing at least one exendin, exendin analog or exendin analog agonist, sufficient to maintain either an average or a minimum plasma concentration of the exendin, exendin agonist or exendin analog agonist of at least about 50 pg/ml for at least about 12 hours, at least about 1 day, at least about 2 days, at least about 3 days, at least about 1 week, at least about 2 weeks, at least about 3 weeks, at least about 1 month, at least about 3 months, or at least about 6 months. In additional embodiments, the average or minimum plasma concentration of the at least one exendin, exendin agonist or exendin analog agonist is at least about 25 pg/ml, about 65 pg/ml, about 75 pg/ml, about 85 pg/ml, about 100 pg/ml, about 150 pg/ml, about 170 pg/ml, about 175 pg/ml, about 200 pg/ml, about 225 pg/ml, about 250 pg/ml, about 300 pg/ml, about 350 pg/ml, about 400 pg/ml, about 450 pg/ml, about 500 pg/ml, about 550 pg/ml, or about 600 pg/ml. In other embodiments, the average or minimum concentration of the exendin, exendin agonist or exendin analog agonist is between at least about 170 pg/ml and 600 pg/ml or between at least about 170 pg/ml and 350 pg/ml. In still other embodiments, the average or minimum plasma concentration of the exendin, exendin agonist or exendin analog agonist is greater than 40 pmoles/liter, greater than 50 pmoles/liter, greater than 60 pmoles/liter, greater than 70 pmoles/liter, greater than 80 pmoles/liter, greater than 90 pmoles/liter, greater than 100 pmoles/liter, greater than 110 pmoles/liter, greater than 120 pmoles/liter, greater than 130 pmoles/liter, greater than 140 pmoles/liter, or greater than 150 pmoles/liter. In still further embodiments, the average or minimum plasma concentration of the exendin, exendin agonist or exendin analog agonist is greater than 40 pmoles/liter but less than 150 pmoles/liter or greater than 40 pmoles/liter but less than 80 pmoles/liter. In one embodiment, the subject in need thereof is obese or is desirous or in need of reducing body weight. In one embodiment, the exendin, exendin agonist or exendin analog agonist is exendin-4. In other embodiments, the concentration of the exendin, exendin agonist or exendin analog agonist is the concentration of an exendin, exendin agonist or exendin analog agonist that results in a biological or therapeutic effect, e.g. reducing postprandial circulating glucose excursions, equivalent to that observed with a given concentration of exendin-4.

A further embodiment provides a method for reducing overall daily average blood glucose concentration in a subject in need thereof, for example a subject with type I, type II or gestational diabetes, comprising administering to said subject an amount of a formulation or medicament containing at least one exendin, exendin analog or exendin analog agonist, sufficient to maintain either an average or a minimum plasma concentration of the exendin, exendin agonist or exendin analog agonist of at least about 50 pg/ml for at least about 12 hours, at least about 1 day, at least about 2 days, at least about 3 days, at least about 1 week, at least about 2 weeks, at least about 3 weeks, at least about 1 month, at least about 3 months, or at least about 6 months. In additional embodiments, the average or minimum plasma concentration of the at least one exendin, exendin agonist or exendin analog agonist is at least about 25 pg/ml, at least about 65 pg/ml, at least about 75 pg/ml, at least about 85 pg/ml, at least about 100 pg/ml, at least about 150 pg/ml, at least about 170 pg/ml, at least about 175 pg/ml, at least about 200 pg/ml, at least about 225 pg/ml, at least about 250 pg/ml, at least about 300 pg/ml, at least about 350 pg/ml, at least about 400 pg/ml, at least about 450 pg/ml, at least about 500 pg/ml, at least about 550 pg/ml or at least about 600 pg/ml. In other embodiments, the average or minimum concentration of the exendin, exendin agonist or exendin analog agonist is between at least about 170 pg/ml and 600 pg/ml or between at least about 170 pg/ml and 350 pg/ml. In still other embodiments, the average or minimum plasma concentration of the exendin, exendin agonist or exendin analog agonist is greater than 40 pmoles/liter, greater than 50 pmoles/liter, greater than 60 pmoles/liter, greater than 70 pmoles/liter, greater than 80 pmoles/liter, greater than 90 pmoles/liter, greater than 100 pmoles/liter, greater than 110 pmoles/liter, greater than 120 pmoles/liter, greater than 130 pmoles/liter, greater than 140 pmoles/liter, or greater than 150 pmoles/liter. In still further embodiments, the average or minimum plasma concentration of the exendin, exendin agonist or exendin analog agonist is greater than 40 pmoles/liter but less than 150 pmoles/liter or greater than 40 pmoles/liter but less than 80 pmoles/liter. In one embodiment, the subject in need thereof is obese or is desirous or in need of reducing body weight. In one embodiment, the exendin, exendin agonist or exendin analog agonist is exendin-4. In other embodiments, the concentration of the exendin, exendin agonist or exendin analog agonist is the concentration of an exendin, exendin agonist or exendin analog agonist that results in a biological or therapeutic effect, e.g. reducing average daily blood glucose concentrations, equivalent to that observed with a given concentration of exendin-4.

In further embodiments, any of the above average or minimum plasma concentrations of at least one exendin, exendin agonist, or exendin analog agonist is maintained between about 12 hours, one day, one week or one month and about one year. In other embodiments, any of the above average or sustained plasma concentrations are maintained for at least about 3 days, at least about 5 days, at least about 1 week, at least about 2 weeks, at least about 3 weeks, at least about one month, at least about 2 months, at least about 3 months, at least about 4 months, at least about 5 months, at least about 6 months, at least about 7 months, at least about 8 months, at least about 9 months, at least about 10 months, at least about 11 months or at least about one year.

The formulations disclosed herein can be administered by any appropriate means known in the art, for example, intravenously, transmucosally, intranasally, orally, intramuscularly, subcutaneously, transdermally, by inhalation or by pulmonary administration. In one embodiment, the formulation is a sustained release or long acting formulation, that is, the formulation releases the at least one exendin, exendin agonist, or exendin analog agonist into the body over a given period of time, for example about 1 day, about 1 week or about 1 month. In further embodiments, the formulation is administered once a day, every other day, once a week, every other week, every third week, once a month, every other month, or every third month. In additional embodiments, the formulation further comprises a biocompatible polymer and sugar, for example sucrose. In one particular embodiment, the formulation is a long-acting formulation containing 5% (w/w) of at least one exendin, exendin agonist or exendin analog agonist, which is administered once a week at a dose of 2.0 mg. In another particular embodiment, the formulation long-acting formulation containing 5% (w/w) of at least one exendin, exendin agonist or exendin analog agonist, is administered once a week at a dose of 0.8 mg. Any formulation for sustained release of the exendin, exendin agonist or exendin analog agonist can be used, including, but not limited to, U.S. Pat. No. 6,828,303; U.S. Patent Application Publications 20060084604, 20060034923, 20060034889 and 20050171503; European Patent Application Publication EP 1512395 A1; and International Patent Application Publications WO2006041538, WO2006017852, WO2005041873, WO2005112633 and WO2005040195.

In further embodiments, any of the methods or medicaments disclosed herein result in the subject's body weight being reduced by at least 1%, at least 5%, at least 10%, at least 20%, at least 30%, at least 40% or at least 50%. In additional embodiments, any of the methods disclosed herein result in the subject's body weight being reduced by at least about 5 pounds or 2 kg, at least about 10 pounds or 5 kg, at least about 20 pounds or 10 kg, at least about 30 pounds or 15 kg, at least about 40 pounds or 20 kg, at least about 50 pounds or 25 kg, at least about 75 pounds or 35 kg, at least about 100 pounds or 50 kg, at least about 125 pounds or 55 kg, at least about 150 pounds or 75 kg, at least about 175 pounds or 80 kg, or at least about 200 pounds or 100 kg. In still further embodiments, practice of any of the methods disclosed herein results in weight reduction, wherein less than about 40%, less than about 20%, less than about 10%, less than about 5%, less than about 2%, less than about 1%, or 0% of the weight loss is due to loss of mean body mass.

In other embodiments, $HbA_{1c}$ is reduced by at least 0.5%, at least 1.0%, at least 1.5%, at least 2.0%, at least 2.5% or at least 3.0%. In further embodiments, $HbA_{1c}$ is reduced to less than 7.5%, less than 7.0%, less than 6.5%, less than 6.0%, less than 5.5%, less than 5.0%, less than 4.5% or less than 4.0%. In still another embodiment, average postprandial glucose levels do not exceed 175 mg/dl, 170 mg/dl, 165 mg/dl, 160 mg/dl, 155 mg/dl or 150 mg/dl. In another embodiment, overall average daily blood glucose concentration is less than 175 mg/dl, less than 165 mg/dl, less than 160 mg/dl, less than 155 mg/dl, less than 150 mg/dl, less than 145 mg/dl, less than 140 mg/dl, less than 135 mg/dl, less than 130 mg/dl, less than 125 mg/dl, less than 120 mg/dl, less than 110 mg/dl or less than 100 mg/dl. In yet another embodiment, fasting glucose levels are reduced to less than 200 mg/dl, less than 190 mg/dl, less than 180 mg/dl, less than 170 mg/dl, less than 160 mg/dl, less than 150 mg/dl, less than 140 mg/dl, less than 130 mg/dl, less than 120 mg/dl, less than 110 mg/dl, less than 100 mg/dl, less than 90 mg/dl, or less than 80 mg/dl.

Additional embodiments provide that the exendin, exendin analog or exendin analog agonist is one or more of exendin-3, exendin-4 or an exendin analog agonist. In some embodiments, the exendin, exendin analog or exendin analog agonist is not exendin-3 or exendin-4. In further embodiments, exendin analog agonists are those described by any one of SEQ ID NOs 3 to 22. In other embodiments, the subject is overweight or obese. In some embodiments, methods disclosed herein further provide that the exendin, exendin analog or exendin analog agonist is co-administered with one or more oral diabetic agents. Such agents include, but are not limited to metformin, a sulphonylurea (SU), a thiazolidinedione (TZD) or any combination thereof.

In additional embodiments a subject need of reducing body weight has a body mass index (BMI) of greater than or equal to about 25, while in other embodiments the subject has a BMI of greater than or equal to about 30. In other embodiments the subject in need of or desirous of reducing body weight suffers from diabetes, insulin resistance or impaired glucose tolerance, while in other embodiments the subject does not suffer from diabetes, insulin resistance or impaired glucose tolerance. In any of the embodiments disclosed herein, the subject may be a human or an animal, for example a mammal, and in particular a domestic animal. In other embodiments, the domestic animal is a companion animal, such as a dog, cat, etc., while in still other embodiments the domestic animal is a livestock species, such as sheep, cattle, swine, horses, buffalo, poultry, etc.

One particular embodiment provides a method for reducing body weight comprising administering by weekly subcutaneous injections to a subject in need of, or desirous of weight reduction, a long acting or sustained release formulation comprising an amount of at least one compound selected from the group consisting of an exendin, an exendin agonist, and an exendin analog agonist, sufficient to maintain an average plasma concentration of the exendin, exendin agonist, or exendin analog agonist of at least 50 pg/ml for at least about 12 hours, at least about 1 day, at least about 2 days, at least about 3 days, at least about 1 week, at least about 2 weeks, at least about 3 weeks, at least about 1 month, at least about 3 months, or at least about 6 months. In a further embodiment, the average plasma concentration is between about 25 pg/ml and about 600 pg/ml, between about 100 pg/ml and about 600 pg/ml, between about 170 pg/ml and about 600 pg/ml, between about 200 pg/ml and about 600 pg/ml, and between about 225 pg/ml and about 600 pg/ml. In additional embodiments, the average plasma concentration of the at least one exendin, exendin agonist or exendin analog agonist is at least about 25 pg/ml, about 65 pg/ml, about 75 pg/ml, about 85 pg/ml, about 100 pg/ml, about 150 pg/ml, about 170 pg/ml, about 175 pg/ml, about 200 pg/ml, about 225 pg/ml, about 250 pg/ml, about 300 pg/ml, about 350 pg/ml, about 400 pg/ml, about 450 pg/ml, about 500 pg/ml, about 550 pg/ml or about 600 pg/ml. In still other embodiments, the average plasma concentration of the exendin, exendin agonist or exendin analog agonist is greater than 40 pmoles/liter, greater than 50 pmoles/liter, greater than 60 pmoles/liter, greater than 70 pmoles/liter, greater than 80 pmoles/liter, greater than 90 pmoles/liter, greater than 100 pmoles/liter, greater than 110 pmoles/liter, greater than 120 pmoles/liter, greater than 130 pmoles/liter, greater than 140 pmoles/liter, or greater than 150 pmoles/liter. In still further embodiments, the average plasma concentration of the exendin, exendin agonist or exendin analog agonist is greater than 40 pmoles/liter but less than 150 pmoles/liter or greater than 40 pmoles/liter but less than 80 pmoles/liter. In one embodiment, the exendin, exendin agonist or exendin analog agonist is exendin-4. In other embodiments, the concentration of the exendin, exendin agonist or exendin analog agonist is the concentration of an exendin, exendin agonist or exendin analog agonist that results in a biological or therapeutic effect, e.g. weight reduction, equivalent to that observed with a given concentration of exendin-4.

Another particular embodiment provides, a method for reducing body weight comprising administering by weekly subcutaneous injections to a subject in need or, or desirous of weight reduction, a long acting or sustained release formulation comprising an amount of at least one compound selected from the group consisting of an exendin, an exendin agonist, and an exendin analog agonist, sufficient to maintain a minimum plasma concentration of the exendin, exendin agonist, or exendin analog agonist of at least 50 pg/ml for at least about 12 hours, at least about 1 day, at least about 2 days, at least about 3 days, at least about 1 week, at least about 2 weeks, at least about 3 weeks, at least about 1 month, at least about 3 months, or at least about 6 months. In a further embodiment, the minimum plasma concentration is between about 25 pg/ml and about 600 pg/ml, between about 100 pg/ml and about 600 pg/ml, between about 170 pg/ml and about 600 pg/ml, between about 200 pg/ml and about 600 pg/ml, and between about 225 pg/ml and about 600 pg/ml. In additional embodiments, the minimum plasma concentration of the at least one exendin, exendin agonist or exendin analog agonist is at least about 25 pg/ml, about 65 pg/ml, about 75 pg/ml, about 85 pg/ml, about 100 pg/ml, about 150 pg/ml, about 170 pg/ml, about 175 pg/ml, about 200 pg/ml, about 225 pg/ml, about 250 pg/ml, about 300 pg/ml, about 350 pg/ml, about 400 pg/ml, about 450 pg/ml, about 500 pg/ml, about 550 pg/ml or about 600 pg/ml. In still other embodiments, the minimum plasma concentration of the exendin, exendin agonist or exendin analog agonist is greater than 40 pmoles/liter, greater than 50 pmoles/liter, greater than 60 pmoles/liter, greater than 70 pmoles/liter, greater than 80 pmoles/liter, greater than 90 pmoles/liter, greater than 100 pmoles/liter, greater than 110 pmoles/liter, greater than 120 pmoles/liter, greater than 130 pmoles/liter, greater than 140 pmoles/liter, or greater than 150 pmoles/liter. In still further embodiments, the minimum plasma concentration of the exendin, exendin agonist or exendin analog agonist is greater than 40 pmoles/liter but less than 150 pmoles/liter or greater than 40 pmoles/ liter but less than 80 pmoles/liter. In one embodiment, the exendin, exendin agonist or exendin analog agonist is exendin-4. In other embodiments, the concentration of the exendin, exendin agonist or exendin analog agonist is the concentration of an exendin, exendin agonist or exendin analog agonist that results in a biological or therapeutic effect, e.g. weight reduction, equivalent to that observed with a given concentration of exendin-4. In further embodiments, the subject suffers from diabetes or impaired glucose tolerance.

Further provided herein is the use of a formulation comprising an amount of at least one exendin, exendin agonist or exendin analog agonist sufficient to mediate the effects or treat the diseases or disorders disclosed herein. Also provided is the use of at least one exendin, exendin agonist or exendin analog agonist to manufacture a medicament to mediate the effects or treat the diseases or disorders disclosed herein.

DETAILED DESCRIPTION

Figure 1:
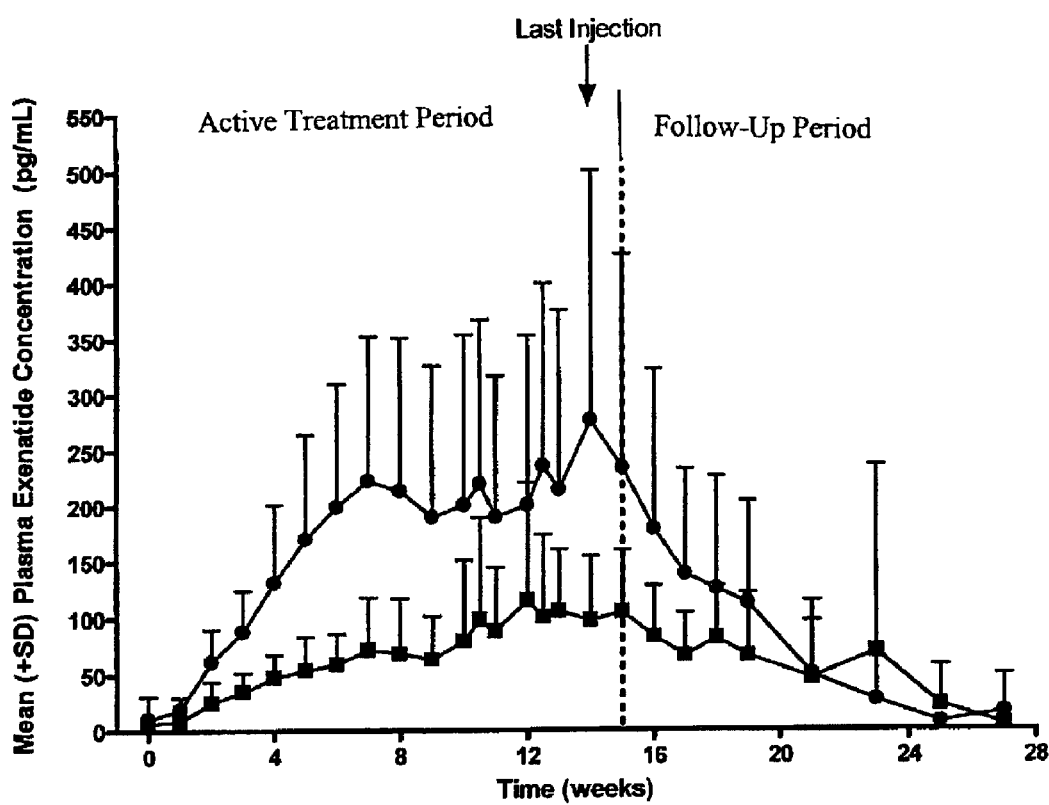
FIG. 1. Plasma exenatide concentrations (mean±SD) over time in subjects receiving exenatide LAR (N=31). Note that the last injection was administered at Week 14. Four patients had exenatide concentrations measured as much lower than the average, possibly due to assay interference. ■=0.8 mg exenatide LAR, N=16, ●=2.0 mg exenatide LAR, N=15.

The following detailed description is provided to aid those skilled in the art in practicing the present invention. Even so, this detailed description should not be construed to unduly limit the present invention as modifications and variations in the embodiments discussed herein can be made by those of ordinary skill in the art without departing from the scope of the present inventive discovery.

All publications, patents, patent applications, and other references cited in this application are hereby incorporated by reference in their entirety as if each individual publication, patent, patent application, or other reference was specifically and individually indicated to be incorporated by reference.

The present disclosure is directed to compositions, medicaments and methods for reducing body weight, maintaining body weight, reducing body weight gain, altering body composition, treating diabetes, lower fasting glucose, lowering $HbA_{1c}$, reducing average daily blood glucose, or lowering postprandial glucose in a subject in need or desirous thereof, by chronically administering an exendin an exendin agonist or an exendin analog agonist. The methods contemplate the chronic or sustained administration of an effective amount of an exendin, an exendin agonist or an exendin analog agonist to a subject to affect the desired results as described herein.

The administered exendin, exendin agonist, or exendin analog agonist may be in the form of a peptide, a pro-drug, or as a pharmaceutical salt or salts thereof. The term "prodrug" refers to a compound that is a drug precursor that, following administration, releases the drug in vivo via some chemical or physiological process, for example, proteolytic cleavage, or upon reaching an environment of a certain pH.

The methods disclosed can be used on any individual in need of such methods or individuals for whom practice of the methods is desired. These individuals may be any mammal including, but not limited to, humans, dogs, horses, cows, pigs, and other commercially valuable or companion animals.

In one embodiment, the present application provides methods for reducing weight in a subject desirous or in need thereof, where the method comprises the administration of an amount of an exendin, exendin agonist, or an exendin analog agonist effective to cause weight reduction in the subject. In another embodiment, the method comprises the chronic or sustained administration of an amount of an exendin, an exendin agonist, or an exendin analog agonist effective to cause weight reduction to the subject. In still another embodiment, the weight reduction is due to a reduction in body fat or adipose tissue without a corresponding reduction in lean body mass or muscle mass. In still another embodiment, the reduction in body weight due to loss of body fat is greater than the reduction in weight due to loss of lean body mass or muscle mass. In one embodiment the reduction in body fat as compared to lean tissue or muscle is based on an absolute weight basis while in another embodiment it is based a percent of weight lost basis. In one embodiment, the loss of visceral fat is greater than the loss of non-visceral fat. In another embodiment, the loss of non-visceral fat is greater than the loss of visceral fat. In yet another embodiment the application provides methods for altering body composition, for example by reducing the ratio of fat to lean tissue, reducing the percent body fat, or increasing the percent lean tissue in an individual.

As used herein, "weight reduction" refers to a decrease in a subject's body weight. In one embodiment, the decrease in body weight is a result of a preferential decrease in the body fat of the subject. In one embodiment, the loss of visceral fat is greater than the loss of non-visceral fat. In another embodiment, the loss of non-visceral fat is greater than the loss of visceral fat. While the invention does not depend on any particular reduction in the subject's weight, the methods described herein will, in various embodiments, reduce the subject's weight by at least about 1%, at least about 2%, at least about 3%, at least about 4%, at least about 5%, at least about 10%, at least about 15, at least about 20%, at least about 30%, at least about 40%, at least about 50%, at least about 60%, or at least about 70% compared to the subject's body weight prior to initiation of the methods disclosed herein. In various embodiments, the weight reduction occurs over a period of about 1 week, about 2 weeks, about 3 weeks, about 1 month, about 2 months, about 3 months, about 4 months, about 5 months, about 6 months, about 7 months, about 8 months, about 9 months, about 10 months, about 11 months, about 1 year or more. In other embodiments, the subject may lose about 5, about 6, about 7, about 8, about 9, about 10, about 15, about 20, about 25, about 30, about 35, about 40, about 45, about 50 about 100, about 125, about 150, about 175, about 200 or more pounds. A reduction in weight can be measured using any reproducible means of measurement. In one embodiment, weight reduction can be measured by calculating a subject's body mass index and comparing that subject's BMI over a period of time. Body mass index can be calculated using any method available, for example by using a nomogram or similar device.

In some embodiments, the exendin, exendin agonist or exendin analog agonists is given by chronic administration. As used herein, "chronic administration" refers to administration of the agent(s) in a continuous mode as opposed to an acute mode, so as to maintain the plasma concentration needed to obtain the desired therapeutic effect (activity) for an extended period of time. In one aspect, "chronic administration" refers to the administration of the exendin or exendin agonist in a continuous mode, so as to maintain a plasma concentration at or above the therapeutically effective or desired amount. In one embodiment, such chronic administration maintains an average plasma exendin, exendin agonist or exendin analog agonist concentration of at least about 25 pg/ml, at least about 50 pg/ml, at least about 65 pg/ml, at least about 75 pg/ml, at least about 85 pg/ml, at least about 100 pg/ml, at least about 150 pg/ml, at least about 170 pg/ml, at least about 175 pg/ml, at least about 200 pg/ml, at least about 225 pg/ml, at least about 250 pg/ml, at least about 300 pg/ml, at least about 350 pg/ml, at least about 400 pg/ml, at least about 450 pg/ml, at least about 500 pg/ml, at least about 550 pg/ml or at least about 600 pg/ml for an extended period of time. In other embodiments, the average concentration of the exendin, exendin agonist or exendin analog agonist is between at least about 170 pg/ml and 600 pg/ml or between at least about 170 pg/ml and 350 pg/ml. In still other embodiments, the average plasma concentration of the exendin, exendin agonist or exendin analog agonist is greater than 40 pmoles/liter, greater than 50 pmoles/liter, greater than 60 pmoles/liter, greater than 70 pmoles/liter, greater than 80 pmoles/liter, greater than 90 pmoles/liter, greater than 100 pmoles/liter, greater than 110 pmoles/liter, greater than 120 pmoles/liter, greater than 130 pmoles/liter, greater than 140 pmoles/liter, or greater than 150 pmoles/liter. In still further embodiments, the average plasma concentration of the exendin, exendin agonist or exendin analog agonist is greater than 40 pmoles/liter but less than 150 pmoles/liter or greater than 40 pmoles/liter but less than 80 pmoles/liter. In one embodiment, the exendin, exendin agonist or exendin analog agonist is exendin-4. In other embodiments, the concentration of the exendin, exendin agonist or exendin analog agonist is the concentration of an exendin, exendin agonist or exendin analog agonist that results in a biological or therapeutic effect, e.g. weight reduction, glucose lowering, alteration in body composition, etc., equivalent to that observed with a given concentration of exendin-4.

In another embodiment such chronic administration maintains a minimum plasma exendin, exendin agonist or exendin analog agonist concentration at or above about 25 pg/ml, at or above about 50 pg/ml, at or above about 65 pg/ml, at or above about 75 pg/ml, at or above about 85 pg/ml, at or above about 100 pg/ml, at or above about 150 pg/ml, at or above about 170 pg/ml, at or above about 175 pg/ml, at or above about 200 pg/ml, at or above about 225 pg/ml, at or above about 250 pg/ml, at or above about 300 pg/ml, at or above about 350 pg/ml, at or above about 400 pg/ml, at or above about 450 pg/ml, at or above about 500 pg/ml, at or above about 550 pg/ml or at or above about 600 pg/ml for an extended period of time. In other embodiments, the minimum concentration of the exendin, exendin agonist or exendin analog agonist is between at least about 170 pg/ml and 600 pg/ml or between at least about 170 pg/ml and 350 pg/ml. In still other embodiments, the minimum plasma concentration of the exendin, exendin agonist or exendin analog agonist is greater than 40 pmoles/liter, greater than 50 pmoles/liter, greater than 60 pmoles/liter, greater than 70 pmoles/liter, greater than 80 pmoles/liter, greater than 90 pmoles/liter, greater than 100 pmoles/liter, greater than 110 pmoles/liter, greater than 120 pmoles/liter, greater than 130 pmoles/liter, greater than 140 pmoles/liter, or greater than 150 pmoles/liter. In still further embodiments, the minimum plasma concentration of the exendin, exendin agonist or exendin analog agonist is greater than 40 pmoles/liter but less than 150 pmoles/liter or greater than 40 pmoles/liter but less than 80 pmoles/liter. In one embodiment, the exendin, exendin agonist or exendin analog agonist is exendin-4. In other embodiments, the concentration of the exendin, exendin agonist or exendin analog agonist is the concentration of an exendin, exendin agonist or exendin analog agonist that results in a biological or therapeutic effect, e.g. weight reduction, glucose lowering, alteration in body composition, etc., equivalent to that observed with a given concentration of exendin-4.

In still another embodiment, chronic administration maintains the plasma concentration, either average or minimum, of the exendin, exendin agonist or exendin analog agonist for a period of at least about 12 hours or at least about 1, at least about 2, at least about 3, at least about 4, at least about 5, at least about 6, or at least about 7 days. In another embodiment, chronic administration maintains the plasma concentration of the exendin, exendin agonist or exendin analog agonist for at least 1, at least about 2, at least about 3, or at least about 4 weeks or at least about 1, at least about 2, or at least about 3 months. In other embodiments, the exendin, exendin agonist or exendin analog agonist is administered by continuous mode. As used herein, "continuous mode" refers to the introduction of the exendin, exendin agonist or exendin analog agonist into the body, for example, the circulation, and not the means of administration. Thus chronic administration by a continuous mode can result from continuous infusion, either intravenously or subcutaneously; the use of a pump or metering system, either implanted or external, for continuous or intermittent delivery; or by the use of an extended release, slow release, sustained release or long acting formulation that is administered, for example, once daily, twice weekly, weekly, twice monthly, monthly, every other month or every third month. It should be recognized that the average or minimum plasma level need not be reached immediately upon administration of the formulation, but may take anywhere from hours to days to weeks to be reached. Once reached, the average or minimum plasma concentration is then maintained for the desired period of time to have its therapeutic effect.

As used herein in the context of weight reduction or altering body composition, a "subject in need thereof" is a subject who is overweight or obese. As used herein in the context of weight reduction or altering body composition, a "desirous" subject is a subject who wishes to reduce their body weight or alter their body composition, for example, by lessening their ratio of fat to lean tissue. In one embodiment, the subject is an obese or overweight subject. In exemplary embodiments, an "overweight subject" refers to a subject with a body mass index (BMI) greater than 25, or a BMI between 25 and 30. It should be recognized, however, that meaning of overweight is not limited to individuals with a BMI of greater than 25, but refers to any subject where weight loss is desirable or indicated for medical or cosmetic reasons. While "obesity" is generally defined as a body mass index over 30, for purposes of this disclosure, any subject, who needs or wishes to reduce body weight is included in the scope of "obese." In one embodiment, subjects who are insulin resistant, glucose intolerant, or have any form of diabetes mellitus (e.g., type 1, 2 or gestational diabetes) can benefit from this method. In another embodiment, a subject in need thereof is obese. It should be noted, however, that the method described herein may be applied to subjects who do not have and/or have not been diagnosed with impaired glucose tolerance, insulin resistance or diabetes mellitus.

As used herein in the context of treating diabetes, reducing $HbA_{1c}$, controlling postprandial blood glucose, lowering fasting glucose and reducing overall daily blood glucose concentration, a subject in need thereof may include subjects with diabetes, impaired glucose tolerance, insulin resistance, or subjects unable to auto-regulate blood glucose.

$HbA_{1c}$ or $A_{1c}$ or glycated hemoglobin or glycohemoglobin as commonly used in the art refers to glycosylated hemoglobin.

In one embodiment, methods for reducing body weight, reducing the ratio of fat to lean tissue or reducing BMI are provided wherein the method comprises chronically administering an amount of an exendin, an exendin agonist or an exendin analog agonist to a subject in need or desirous thereof. In one embodiment, the weight loss attributed to loss of fat or adipose tissue is greater than the weight loss due to lean tissue. In another embodiment, the percent of weight reduction due to loss of lean body mass is less than about 40%, less that about 30%, less than about 20%, less than about 10%, less than about 5%, less than about 2%, less than about 1%, or 0% of the total weight reduction. In one embodiment, the exendin, exendin agonist or exendin analog agonist is administered in an extended release, slow release, sustained release or long acting formulation. In one embodiment, the exendin or exendin agonist is administered in a polymer-based sustained release formulation. Such polymer-based sustained release formulations are described, for example, in U.S. patent application Ser. No. 09/942,631, filed Aug. 31, 2001 (now U.S. Pat. No. 6,824,822) and related application Ser. No. 11/312,371, filed Dec. 21, 2005; U.S. Provisional Application No. 60/419,388, filed Oct. 17, 2002 and related U.S. patent application Ser. Nos. 10/688,786 and 10/688,059 filed Oct. 17, 2003; U.S. Provisional Application No. 60/757, 258, filed Jan. 9, 2006; U.S. Provisional Application Ser. No. 60/563,245, filed Apr. 15, 2004 and related U.S. patent application Ser. No. 11/104,877, filed Apr. 13, 2005; and U.S. patent application Ser. No. 11/107,550, filed Apr. 15, 2005, the entireties of which are incorporated herein by reference.

The exendin, exendin agonist or exendin analog agonist can be administered by any method available. In one embodiment, the exendin or exendin agonist is administered subcutaneously.

Also provided are methods for reducing body weight comprising administering an amount of an exendin or exendin agonist sufficient to achieve an average or minimum circulating blood plasma level of an exendin, an exendin agonist, or an exendin analog agonist of at least about 50 pg/ml for a period of at least about 12 hours, 1 day, 2 days, 3 days, 1 week, 2 weeks, 3 weeks, 1 month, 3 months, or 6 months. In one embodiment, the methods comprise the administration of an exendin, an exendin agonist or an exendin analog agonist sufficient to achieve an average or minimum circulating blood plasma concentration of at least about 50 pg/ml, at least about 65 pg/ml, at least about 75 pg/ml, at least about 100 pg/ml, at least about 150 pg/ml, at least about 170 pg/ml, at least about 175 pg/ml, at least about 200 pg/ml, at least about 225 pg/ml, at least about 250 pg/ml, at least about 350 pg/ml, at least about 400 pg/ml, at least about 450 pg/ml, at least about 500 pg/ml, at least about 550 pg/ml or at least about 600 pg/ml of the exendin, exendin agonist or exendin analog agonist. In other embodiments, the average or minimum concentration of the exendin, exendin agonist or exendin analog agonist is between at least about 170 pg/ml and 600 pg/ml or between at least about 170 pg/ml and 350 pg/ml. In still other embodiments, the average or minimum plasma concentration of the exendin, exendin agonist or exendin analog agonist is greater than 40 pmoles/liter, greater than 50 pmoles/liter, greater than 60 pmoles/liter, greater than 70 pmoles/liter, greater than 80 pmoles/liter, greater than 90 pmoles/liter, greater than 100 pmoles/liter, greater than 110 pmoles/liter, greater than 120 pmoles/liter, greater than 130 pmoles/liter, greater than 140 pmoles/liter, or greater than 150 pmoles/liter. In still further embodiments, the average or minimum plasma concentration of the exendin, exendin agonist or exendin analog agonist is greater than 40 pmoles/liter but less than 150 pmoles/liter or greater than 40 pmoles/liter but less than 80 pmoles/liter. In one embodiment, the exendin, exendin agonist or exendin analog agonist is exendin-4. In other embodiments, the concentration of the exendin, exendin agonist or exendin analog agonist is the concentration of an exendin, exendin agonist or exendin analog agonist that results in a biological or therapeutic effect, e.g. weight reduction, equivalent to that observed with a given concentration of exendin-4. In one embodiment, the average or minimum circulating blood plasma concentrations are achieved for a period of about 2, about 3, about 4, about 5, about 6, or about 7 days. In a further embodiment, the average or minimum plasma concentrations are achieved for a period of about 1, about 2, about 3, about 4, about 5, about 6, about 7, about 8, about 9, about 10, about 11, about 12, about 13, about 14, about 15 or about 16 weeks. In still a further embodiment, the average or minimum plasma concentrations are achieved for a period of about 5, about 6, about 7, about 8, about 9, about 10, about 11, or about 12 months. Any method for determining circulating blood concentrations of exendin or exendin agonist may be employed with the claimed methods.

Also provided are methods for treating diabetes, for example, type I, type II or gestational diabetes, comprising administering an amount of an exendin or exendin agonist sufficient to achieve an average or minimum circulating blood plasma level of an exendin, an exendin agonist, or an exendin analog agonist of at least about 50 pg/ml for a period of at least about 12 hours, at least about 1 day, at least about 2 days, at least about 3 days, at least about 1 week, at least about 2 weeks, at least about 3 weeks, at least about 1 month, at least about 3 months, or at least about 6 months. In one embodiment, the methods comprise the administration of an exendin, an exendin agonist or an exendin analog agonist sufficient to achieve an average or minimum circulating blood plasma concentration of at least about 25 pg/ml, at least about 50 pg/ml, at least about 65 pg/ml, at least about 75 pg/ml, at least about 100 pg/ml, at least about 150 pg/ml, at least about 170 pg/ml, at least about 175 pg/ml, at least about 200 pg/ml, at least about 225 pg/ml, at least about 250 pg/ml, at least about 350 pg/ml, at least about 400 pg/ml, at least about 450 pg/ml, at least about 500 pg/ml, at least about 550 pg/ml or at least about 600 pg/ml of the exendin, exendin agonist or exendin analog agonist. In other embodiments, the average or minimum concentration of the exendin, exendin agonist or exendin analog agonist is between at least about 170 pg/ml and 600 pg/ml or between at least about 170 pg/ml and 350 pg/ml. In still other embodiments, the average or minimum plasma concentration of the exendin, exendin agonist or exendin analog agonist is greater than 40 pmoles/liter, greater than 50 pmoles/liter, greater than 60 pmoles/liter, greater than 70 pmoles/liter, greater than 80 pmoles/liter, greater than 90 pmoles/liter, greater than 100 pmoles/liter, greater than 110 pmoles/liter, greater than 120 pmoles/liter, greater than 130 pmoles/liter, greater than 140 pmoles/liter, or greater than 150 pmoles/liter. In still further embodiments, the average or minimum plasma concentration of the exendin, exendin agonist or exendin analog agonist is greater than 40 pmoles/liter but less than 150 pmoles/liter or greater than 40 pmoles/liter but less than 80 pmoles/liter. In one embodiment, the exendin, exendin agonist or exendin analog agonist is exendin-4. In other embodiments, the concentration of the exendin, exendin agonist or exendin analog agonist is the concentration of an exendin, exendin agonist or exendin analog agonist that results in a biological or therapeutic effect, e.g. lowering fasting glucose, reducing postprandial glucose excursion, reducing $HbA_{1c}$, etc., equivalent to that observed with a given concentration of exendin-4.

Another embodiment provides a method of reducing circulating glucose levels, and in particular fasting glucose, without inducing weight loss, reducing appetite, slowing gastric emptying, lowering postprandial glucose levels, or any combination thereof, by administering an exendin, exendin agonist or exendin analog agonist to maintain an average or minimum blood plasma level of the exendin, exendin agonist or exendin analog agonist of between about 25 pg/ml to about 100 pg/ml or between about 50 pg/ml and about 100 pg/ml. In one embodiment, the exendin, exendin agonist or exendin analog agonist is exendin-4. In other embodiments, the concentration of the exendin, exendin agonist or exendin analog agonist is the concentration of an exendin, exendin agonist or exendin analog agonist that results in a biological or therapeutic effect, e.g. glucose lowering, especially fasting glucose, equivalent to that observed with a given concentration of exendin-4. In one embodiment, the average or minimum circulating blood plasma concentrations are achieved for a period of about 2, about 3, about 4, about 5, about 6, or about 7 days. In a further embodiment, the average or minimum plasma concentrations are achieved for a period of about 1, about 2, about 3, about 4, about 5, about 6, about 7, about 8, about 9, about 10, about 11, about 12, about 13, about 14, about 15 or about 16 weeks. In still a further embodiment, the average or minimum plasma concentrations are achieved for a period of about 5, about 6, about 7, about 8, about 9, about 10, about 11, or about 12 months. In alternative embodiments, administration of the exendin, exendin agonist or exendin analog agonist as described herein results in a decrease in fasting glucose levels, postprandial glucose levels or both. Any method for determining circulating blood concentrations of exendin or exendin agonist may be employed with the claimed methods.

Additional embodiments provide methods for the reduction of $HbA_{1c}$, overall daily average blood glucose concentration, fasting blood glucose and/or postprandial blood glucose by administering, for example to a subject in need of a reduction in $HbA_{1c}$, daily average blood glucose, or fasting glucose, an amount of an exendin or exendin agonist sufficient to achieve an average or minimum circulating blood plasma level of an exendin, an exendin agonist, or an exendin analog agonist of at least about 50 pg/ml for a period of at least about 12 hours, at least about 1 day, at least about 2 days, at least about 3 days, at least about 1 week, at least about 2 weeks, at least about 3 weeks, at least about 1 month, at least about 3 months, or at least about 6 months. In one embodiment, the methods comprise the administration of an exendin, an exendin agonist or an exendin analog agonist sufficient to achieve an average or minimum circulating blood plasma concentration of at least about 25 pg/ml, at least about 65 pg/ml, at least about 75 pg/ml, at least about 100 pg/ml, at least about 150 pg/ml, at least about 170 pg/ml, at least about 175 pg/ml, at least about 200 pg/ml, at least about 225 pg/ml, at least about 250 pg/ml, at least about 350 pg/ml, at least about 400 pg/ml, at least about 450 pg/ml, at least about 500 pg/ml, at least about 550 pg/ml or at least about 600 pg/ml of the exendin, exendin agonist or exendin analog agonist. In other embodiments, the average or minimum concentration of the exendin, exendin agonist or exendin analog agonist is between at least about 170 pg/ml and 600 pg/ml or between at least about 170 pg/ml and 350 pg/ml. In still other embodiments, the average or minimum plasma concentration of the exendin, exendin agonist or exendin analog agonist is greater than 40 pmoles/liter, greater than 50 pmoles/liter, greater than 60 pmoles/liter, greater than 70 pmoles/liter, greater than 80 pmoles/liter, greater than 90 pmoles/liter, greater than 100 pmoles/liter, greater than 110 pmoles/liter, greater than 120 pmoles/liter, greater than 130 pmoles/liter, greater than 140 pmoles/liter, or greater than 150 pmoles/liter. In still further embodiments, the average or minimum plasma concentration of the exendin, exendin agonist or exendin analog agonist is greater than 40 pmoles/liter but less than 150 pmoles/liter or greater than 40 pmoles/liter but less than 80 pmoles/liter. In one embodiment, the exendin, exendin agonist or exendin analog agonist is exendin-4. In other embodiments, the concentration of the exendin, exendin agonist or exendin analog agonist is the concentration of an exendin, exendin agonist or exendin analog agonist that results in a biological or therapeutic effect, e.g. lowering $HbA_{1c}$, equivalent to that observed with a given concentration of exendin-4. In one embodiment, the average or minimum circulating blood plasma concentrations are achieved for a period of about 2, about 3, about 4, about 5, about 6, or about 7 days. In a further embodiment, the average or minimum plasma concentrations are achieved for a period of about 1, about 2, about 3, about 4, about 5, about 6, about 7, about 8, about 9, about 10, about 11, about 12, about 13, about 14, about 15 or about 16 weeks. In still a further embodiment, the average or minimum plasma concentrations are achieved for a period of about 5, about 6, about 7, about 8, about 9, about 10, about 11, or about 12 months. Any method for determining circulating blood concentrations of exendin or exendin agonist may be employed with the claimed methods. In further embodiments, the subject is in need of or desirous of a reduction in body weight.

Additionally is provided a method for reducing the increase in postprandial blood glucose concentration compared to preprandial blood glucose concentration, such that the difference between blood glucose concentration before and after a meal is reduced. This results in a lessening of the variation in blood glucose concentrations during the day as determined, for example, by 7 point self monitored blood glucose as described herein. This method comprises administering an amount of an exendin or exendin agonist sufficient to achieve an average or minimum circulating blood plasma level of an exendin, an exendin agonist, or an exendin analog agonist of at least about 50 pg/ml for a period of at least about 12 hours, at least about 1 day, at least about 2 days, at least about 3 days, at least about 1 week, at least about 2 weeks, at least about 3 weeks, at least about 1 month, at least about 3 months, or at least about 6 months. In one embodiment, the methods comprise the administration of an exendin, an exendin agonist or an exendin analog agonist sufficient to achieve an average or minimum circulating blood plasma concentration of at least about 25 pg/ml, at least about 65 pg/ml, at least about 75 pg/ml, at least about 100 pg/ml, at least about 150 pg/ml, at least about 170 pg/ml, at least about 175 pg/ml, at least about 200 pg/ml, at least about 225 pg/ml, at least about 250 pg/ml, at least about 350 pg/ml, at least about 400 pg/ml, at least about 450 pg/ml, at least about 500 pg/ml, at least about 550 pg/ml or at least about 600 pg/ml of the exendin, exendin agonist or exendin analog agonist. In other embodiments, the average or minimum concentration of the exendin, exendin agonist or exendin analog agonist is between at least about 170 pg/ml and 600 pg/ml or between at least about 170 pg/ml and 350 pg/ml. In still other embodiments, the average or minimum plasma concentration of the exendin, exendin agonist or exendin analog agonist is greater than 40 pmoles/liter, greater than 50 pmoles/liter, greater than 60 pmoles/liter, greater than 70 pmoles/liter, greater than 80 pmoles/liter, greater than 90 pmoles/liter, greater than 100 pmoles/liter, greater than 110 pmoles/liter, greater than 120 pmoles/liter, greater than 130 pmoles/liter, greater than 140 pmoles/liter, or greater than 150 pmoles/liter. In still further embodiments, the average or minimum plasma concentration of the exendin, exendin agonist or exendin analog agonist is greater than 40 pmoles/liter but less than 150 pmoles/liter or greater than 40 pmoles/liter but less than 80 pmoles/liter. In one embodiment, the exendin, exendin agonist or exendin analog agonist is exendin-4. In other embodiments, the concentration of the exendin, exendin agonist or exendin analog agonist is the concentration of an exendin, exendin agonist or exendin analog agonist that results in a biological or therapeutic effect, e.g. reducing postprandial blood glucose excurions, average daily blood glucose, etc., equivalent to that observed with a given concentration of exendin-4. In one embodiment, the average or minimum circulating blood plasma concentrations are achieved for a period of about 2, about 3, about 4, about 5, about 6, or about 7 days. In a further embodiment, the average or minimum plasma concentrations are achieved for a period of about 1, about 2, about 3, about 4, about 5, about 6, about 7, about 8, about 9, about 10, about 11, about 12, about 13, about 14, about 15 or about 16 weeks. In still a further embodiment, the average or minimum plasma concentrations are achieved for a period of about 5, about 6, about 7, about 8, about 9, about 10, about 11, or about 12 months. Any method for determining circulating blood concentrations of exendin or exendin agonist may be employed with the claimed methods.

In any one of the embodiments or methods disclosed herein, the circulating plasma exendin, exendin agonist or exendin analog agonist concentrations may be maintained at the average given plasma concentration or within about 10%, about 15%, about 20%, or about 25% of the average given plasma concentration. In other embodiments, the circulating plasma concentrations are maintained at the average given concentration or at about 98%, about 97%, about 96%, about 95%, about 90%, about 80%, about 70%, or about 60% of the average given concentration. Plasma concentrations of the exendin or exendin agonist can be measured using any method available to the skilled artisan.

In any one of the embodiments or methods described herein, the administration of the exendin, exendin agonist, or exendin analog agonist is effective to sustain a minimum circulating plasma exendin, exendin agonist or exendin analog agonist of at least about 50 pg/ml for at least about 12, about 24 or about 48 hours. In other embodiments, the methods comprise the administration of an exendin, an exendin agonist, or an exendin analog agonist sufficient to sustain a minimum circulating plasma concentration of at least about 25 pg/ml, at least about 65 pg/ml, at least about 75 pg/ml, at least about 100 pg/ml, at least about 150 pg/ml, at least about 170 pg/ml, at least about 175 pg/ml, at least about 200 pg/ml, at least about 225 pg/ml, at least about 250 pg/ml, at least about 350 pg/ml, at least about 400 pg/ml, at least about 450 pg/ml, at least about 500 pg/ml, at least about 550 pg/ml or at least about 600 pg/ml of the exendin, exendin agonist or exendin analog agonist. In other embodiments, the minimum concentration of the exendin, exendin agonist or exendin analog agonist is between at least about 170 pg/ml and 600 pg/ml or between at least about 170 pg/ml and 350 pg/ml. In still other embodiments, the minimum plasma concentration of the exendin, exendin agonist or exendin analog agonist is greater than 40 pmoles/liter, greater than 50 pmoles/liter, greater than 60 pmoles/liter, greater than 70 pmoles/liter, greater than 80 pmoles/liter, greater than 90 pmoles/liter, greater than 100 pmoles/liter, greater than 110 pmoles/liter, greater than 120 pmoles/liter, greater than 130 pmoles/liter, greater than 140 pmoles/liter, or greater than 150 pmoles/liter. In still further embodiments, the minimum plasma concentration of the exendin, exendin agonist or exendin analog agonist is greater than 40 pmoles/liter but less than 150 pmoles/liter or greater than 40 pmoles/liter but less than 80 pmoles/liter. In one embodiment, the exendin, exendin agonist or exendin analog agonist is exendin-4. In other embodiments, the concentration of the exendin, exendin agonist or exendin analog agonist is the concentration of an exendin, exendin agonist or exendin analog agonist that results in a biological or therapeutic effect, e.g. weight reduction, glucose lowering, alteration in body composition, etc., equivalent to that observed with a given concentration of exendin-4. In certain embodiments the minimum concentration of the exendin, exendin agonist or exendin analog agonist is sustained for a period of at least about 2, at least about 3, at least about 4, at least about 5, at least about 6, or at least about 7 days. In various embodiments, minimum circulating plasma concentrations are sustained for at least about 2, at least about 3, at least about 4, at least about 5, at least about 6, at least about 7, at least about 8, at least about 9, at least about 10, at least about 11, at least about 12, at least about 13, at least about 14, at least about 15 or at least about 16 weeks. In further embodiments, the minimum circulating plasma levels are sustained for at least about 5, at least about 6, at least about 7, at least about 8, at least about 9, at least about 10, at least about 11 or at least about 12 months. Plasma concentrations of the exendin, exendin agonist or exendin analog agonist can be measured using any method available to the skilled artisan.

In any one of the embodiments or methods described herein, the administration the exendin, exendin agonist, or exendin analog agonist is effective to maintain an average plasma exendin, exendin agonist or exendin analog agonist concentrations of at least about 50 pg/ml for at least about 12, at least about 24 or at least about 48 hours. In other embodiments, the methods comprise the administration of an exendin, an exendin agonist, or an exendin analog agonist sufficient to sustain an average circulating plasma concentration of at least about 25 pg/ml, at least about 65 pg/ml, at least about 75 pg/ml, at least about 100 pg/ml, at least about 150 pg/ml, at least about 170 pg/ml, at least about 175 pg/ml, at least about 200 pg/ml, at least about 225 pg/ml, at least about 250 pg/ml, at least about 350 pg/ml, at least about 400 pg/ml, at least about 450 pg/ml, at least about 500 pg/ml, at least about 550 pg/ml or at least about 600 pg/ml. pg/ml of the exendin, exendin agonist or exendin analog agonist. In other embodiments, the average concentration of the exendin, exendin agonist or exendin analog agonist is between at least about 170 pg/ml and 600 pg/ml or between at least about 170 pg/ml and 350 pg/ml. In still other embodiments, the average plasma concentration of the exendin, exendin agonist or exendin analog agonist is greater than 40 pmoles/liter, greater than 50 pmoles/liter, greater than 60 pmoles/liter, greater than 70 pmoles/liter, greater than 80 pmoles/liter, greater than 90 pmoles/liter, greater than 100 pmoles/liter, greater than 110 pmoles/liter, greater than 120 pmoles/liter, greater than 130 pmoles/liter, greater than 140 pmoles/liter, or greater than 150 pmoles/liter. In still further embodiments, the average plasma concentration of the exendin, exendin agonist or exendin analog agonist is greater than 40 pmoles/liter but less than 150 pmoles/liter or greater than 40 pmoles/liter but less than 80 pmoles/liter. In one embodiment, the exendin, exendin agonist or exendin analog agonist is exendin-4. In other embodiments, the concentration of the exendin, exendin agonist or exendin analog agonist is the concentration of an exendin, exendin agonist or exendin analog agonist that results in a biological or therapeutic effect, e.g. weight reduction, glucose lowering, alteration in body composition, etc., equivalent to that observed with a given concentration of exendin-4. In certain embodiments the average concentration of the exendin, exendin agonist or exendin analog agonist is sustained for a period of at least about 2, at least about 3, at least about 4, at least about 5, at least about 6, or at least about 7 days. In various embodiments, average circulating plasma concentrations are sustained for at least about 2, at least about 3, at least about 4, at least about 5, at least about 6, at least about 7, at least about 8, at least about 9, at least about 10, at least about 11, at least about 12, at least about 13, at least about 14, at least about 15 or at least about 16 weeks. In further embodiments, the average circulating plasma levels are sustained for at least about 5, at least about 6, at least about 7, at least about 8, at least about 9, at least about 10, at least about 11 or at least about 12 months. Plasma concentrations of the exendin, exendin agonist or exendin analog agonist can be measured using any method available to the skilled artisan.

It is also contemplated that the methods disclosed herein are useful in maintaining levels of an exendin, exendin agonist, or exendin analog that control fasting blood glucose with limited effects on, no detectable effects on or without inducing weight loss, reducing appetite, slowing gastric emptying, or exerting postprandial glucose level control. In particular, the methods disclosed herein are useful in controlling fasting blood glucose levels without inducing weight loss. Patient populations benefiting from controlled fasting blood glucose levels without accompanying weight loss include, but are not limited to, elderly patients, patients with human immunodeficiency virus (HIV) infections, or other patients where weight loss is contraindicated. In one embodiment, the methods disclosed herein are useful in maintaining an exendin, exendin agonist, or exendin analog at levels, either average or minimum, of between 10 pg/ml and 150 pg/ml, between 10 pg/ml and 100 pg/ml, between 50 pg/ml and 100 pg/ml, or between 50 pg/ml and 150 pg/ml to control fasting blood glucose without inducing weight loss. In one embodiment, the methods disclosed herein are useful in maintaining an exendin, exendin agonist, or exendin analog at levels, either average or minimum, of between 10 pg/ml and 150 pg/ml, between 10 pg/ml and 100 pg/ml, between 50 pg/ml and 100 pg/ml, or between 50 pg/ml and 150 pg/ml to control fasting blood glucose with no detectable effects on or without inducing weight loss, reducing appetite, slowing gastric emptying, and/or exerting postprandial glucose level control. In one embodiment, the exendin, exendin agonist or exendin analog agonist is exendin-4. In other embodiments, the concentration of the exendin, exendin agonist or exendin analog agonist is the concentration of an exendin, exendin agonist or exendin analog agonist that results in a biological or therapeutic effect, e.g. glucose lowering, and in particular fasting glucose, equivalent to that observed with a given concentration of exendin-4.

In one embodiment, the exendin, exendin agonist or exendin analog agonist is continuously administered. In another embodiment, the exendin, exendin agonist, or exendin analog agonist is administered in a slow release, extended release, sustained release or long acting formulation. In any of the preceding embodiments, the exendin, exendin agonist or exendin analog agonist can be administered once per day, every other day, three times per week, twice per week, once per week, twice a month, monthly, every other month or every three months. In addition, the length of the total time of administration of the exendin, exendin agonist, or exendin agonist analog can be determined by the amount of weight reduction desired. Thus, the exendin, exendin agonist, or exendin analog agonist can be administered according to the methods disclosed herein for a period sufficient to achieve a given target weight, BMI or body composition after which administration can be terminated. Alternatively following achievement of the target weight, BMI or body composition, the dose of the exendin, exendin agonist, or exendin analog agonist can be decreased to a level to maintain the desired target. In addition, if after the target weight is achieved, the subject regains weight, the amount of exendin, exendin agonist, or exendin analog agonist can be increased or, if previously terminated, the administration can be reinitiated.

Likewise in the area of glycemic control, the exendin, exendin agonist or exendin analog agonist can be administered according to the methods disclosed herein for a period sufficient to achieve a target $HbA_{1c}$, a target fasting glucose level, a target overall daily blood glucose concentration, etc. after which the plasma concentration of the exendin, exendin agonist or exendin analog agonist may be reduced to a maintenance level or discontinued. If discontinued, the administration can be resumed later if necessary. In one embodiment, the exendin, exendin agonist or exendin analog agonist is administered according to methods disclosed herein for a period sufficient to lower or stabilize fasting glucose levels, reducing or eliminating high or higher than desired fasting glucose levels.

In some embodiments, methods disclosed herein further provide that the exendin, exendin analog or exendin analog agonist is co-administered with one or more oral diabetic agents. Such agents include, but are not limited to metformin, a sulphonylurea (SU), a thiazolidinedinoe (TZD) or any combination thereof. Exemplary agents include pioglitazone, rosiglitazone, glibenclamide, gliclazide, glimepiride, glipizide, gliquidone, chlorpropamide, and tolbutamide. The exendin, exendin agonist or exendin analog agonist can also be con-administered with insulin. Co-administration can be achieved by any suitable means or dosing regimen.

In one embodiment, methods are provided for the decrease in the frequency and/or severity of gastrointestinal effects associated with exendin, exendin agonist, or exendin analog agonist administration comprising chronically administering an exendin, exendin agonist or exendin analog agonist by any of the methods described herein. Sometimes chronic administration beginning with low or lower doses can induce a tolerance to the administered exendin, exendin agonist, or exendin analog agonist such that high doses that typically elicit unacceptable frequency and/or severity of gastrointestinal effects can be administered to the subject with reduced or absent gastrointestinal effects. Thus, it is contemplated that chronic administration can be initiated with suboptimal dosing of the exendin, exendin agonist or exendin analog agonist using, for example, a formulation that releases the administered exendin, exendin agonist or exendin analog agonist over a period of time where the formulation is administered weekly. Over a period of weeks, the plasma levels of the administered exendin, exendin agonist or exendin analog will increase and eventually achieve a plateau concentration. In some embodiments, this plateau is at a concentration that could not be tolerated due to adverse gastrointestinal effects if administered in a single or initiating dose. Any suitable extended-release formulation and administration regimen can be used to achieve the plateau effect.

Accordingly, in one embodiment multiple sustained release doses are provided such that each successive dose increases the concentration of the agent or agents in the patient, wherein a therapeutically effective concentration of agent or agents is achieved in the patient. In one further embodiment each successive sustained release dose is administered such that its sustained phase overlaps with the sustained phase of the previous dose.

The term "exendin" includes naturally occurring exendin peptides that are found in the salivary secretions of the Gila monster. Exendins of particular interest include exendin-3 [SEQ ID NO:2], which is present in the salivary secretions of Heloderma horridum, and exendin-4 [SEQ ID NO:1], a 39 amino acid peptide which is naturally present in the salivary secretions of Heloderma suspectum (Eng, J., et al., *J. Biol. Chem.,* 265:20259-62, 1990; Eng., J., et al., *J. Biol. Chem.,* 267:7402-05, 1992). Animal testing of exendin-4 has shown that its ability to lower blood glucose persists for several hours. Exendin-4, as it occurs in the salivary secretions of the Gila monster, is an amidated peptide. It should be appreciated, however, that the exendins, exendin agonists and exendin analog agonists for use in the methods described herein are not limited to the amidated forms, but include that acid form or any other physiologically active form of the molecule.

Exendin-4 was first thought to be a component of the venom. It now appears that exendin-4 is devoid of toxicity, and that it instead is made in salivary glands in the Gila monster. The exendins have some amino acid sequence similarity to several members of the glucagon-like peptide family, with the highest amino acid identity, 53%, being to GLP-1[7-36]NH$_2$ (Goke, et al., *J. Biol. Chem.,* 268:19650-55, 1993).

Exendin "agonist activity" as used herein means having the biological activity of an exendin, but it is understood that the activity of the agonist can be either less potent or more potent than the native exendin. Other exendin agonists include, e.g., chemical compounds specifically designed to activate that receptor or receptors at which an exendin exerts its affect on body weight, body composition, blood glucose, etc.

As used herein, the term "exendin analog agonist" refers to an exendin analog having agonist activity.

The term "insulinotropic" as used herein, refers to an ability to stimulate the release of insulin into the circulation.

The term "insulin resistance" as used herein, describes a subnormal biological response to a given concentration of insulin (i.e., decreased glucose transport across the cell membrane in response to insulin).

The term "pharmaceutically acceptable carrier or adjuvant" as used herein, refers to a non-toxic carrier or adjuvant that may be administered to a patient together with a compound of the invention, and which does not destroy the pharmacological activity thereof.

The terms "therapeutically or pharmaceutically effective" or "therapeutically or pharmaceutically effective amount or concentration" refers to an amount of the compound described herein required to reduce body weight, treat obesity, alter body composition, treat diabetes, treat impaired glucose tolerance, reduce fasting glucose, reduce postprandial glucose levels, lower HbA$_{1c}$ or reduce average daily blood glucose in a subject.

As is recognized herein and in the art, exendin agonists and exendin analog agonists may have a biological activity greater or lesser than a reference exendin such as exendin-4. Thus, in certain embodiments, the concentration of the exendin, exendin agonist or exendin agonist analog is relative to a reference exendin. That is, the concentration is that of the reference exendin or a concentration of the exendin agonist or exendin analog agonist necessary to achieve a biological or therapueutic effect equivalent to the reference exendin. In certain embodiments, the reference exendin is exendin-4. In certain embodiments, the concentration of the exendin, exendin agonist or exendin analog agonist is the amount of the exendin, exendin agonists or exendin analog necessary to achieve a given effect, such as weight loss, alteration of body composition, or reduction of blood glucose or HbA$_{1c}$ that is achieved by a given dose of exendin-4.

The terms "pharmaceutically" or "pharmacologically acceptable" refer to molecular entities and compositions that do not produce adverse, allergic, or other untoward reactions when administered to an animal or a human. As used herein, "pharmaceutically acceptable carrier" includes any and all such solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in therapeutic compositions is contemplated. Supplementary active ingredients also can be incorporated into the compositions.

The term "type-2 diabetes mellitus" as used herein, refers to a disease, also known as non-insulin-dependent diabetes mellitus (NIDDM) or adult-onset diabetes mellitus (AODM), in which a patient has elevated concentrations of blood sugar levels.

Certain exendin sequences are compared to the sequence of GLP-1 in Table 1.

TABLE 1

```
a. H A E G T F T S D V S S Y L E G Q A A K E F I A W L V K G R(NH₂)

b. H S D G T F T S D L S K Q M E E E A V R L F I E W L K N G G P S S G A P P P S(NH₂)

c. D L S K Q M E E E A V R L F I E W L K N G G P S S G A P P P S(NH₂)

d. H G E G T F T S D L S K Q M E E E A V R L F I E W L K N G G P S S G A P P P S(NH₂)

e. H S D A T F T A E Y S K L L A K L A L Q K Y L E S I L G S S T S P R P P S S f. H S D A T F T A E Y S K L L A K L A L Q K Y L E S I L G S S T S P R P P S
```

TABLE 1-continued

```
g. H S D A I F T E E Y S K L L A K L A L Q K Y L A S I L G S R T S P P P(NH₂)

h. H S D A I F T Q Q Y S K L L A K L A L Q K Y L A S I L G S R T S P P P(NH₂)
``` a = GLP-1(7-36) (NH₂) [SEQ ID NO: 3].
b = exendin 3 (NH₂) [SEQ ID NO: 2].
c = exendin 4 (9-39)(NH₂) [SEQ ID NO: 4].
d = exendin 4 (NH₂) [SEQ ID NO: 1].
e = helospectin I [SEQ ID NO: 5].
f = helospectin II [SEQ ID NO: 6].
g = helodermin (NH₂) [SEQ ID NO: 7].
h = Q⁸, Q⁹ helodermin (NH₂) [SEQ ID NO: 8].

As used in this specification, by "exendin agonist" is meant a compound which elicits a biological activity of a exendin reference peptide, preferably having a potency better than the exendin reference peptide, or within five orders of magnitude (plus or minus) of potency compared to the exendin reference peptide, for example, 4, 3, 2, or 1 order of magnitude, when evaluated by art-known measures such as receptor binding/competition studies. In one embodiment, the term refers to a compound which elicits a biological effect similar to that of the exendin reference peptide, for example a compound (1) having activity in glucose lowering and/or weight loss assays similar to the exendin reference peptide, and (2) which optionally binds specifically in a reference receptor assay or in a competitive binding assay with labeled exendin reference peptide. Preferably, the agonists will bind in such assays with an affinity of less than 1 µM, and more preferably with an affinity of less than 1-5 nM. Such agonists may comprise a polypeptide comprising an active fragment of a reference peptide or a small chemical molecule. In one embodiment, the exendin agonist is a peptide. In another embodiment, exendin agonists do not include GLP-1 and variants, analogs and derivatives thereof. In another embodiment, the reference peptide is exendin-4.

The structure activity relationship (SAR) of exendin was investigated for structures that may relate to the activity of exendin, for its stability to metabolism, and for improvement of its physical characteristics, especially as it pertains to peptide stability and to amenability to alternative delivery systems, and various exendin analog agonist peptide compounds have been invented. Exendin analog agonists include exendin analogs with agonist activity in which one or more naturally occurring amino acids are inserted, eliminated or replaced with another amino acid(s). Exemplary exendin analogs are peptide analogs of exendin-4. In one aspect, the methods of reducing body weight, reducing BMI, altering body composition, treating diabetes, reducing fasting glucose, or reducing postprandial glucose comprise the chronic administration of an exendin analog, preferably an analog having agonist activity, to a subject in need thereof.

Exendin analogs include peptides that are encoded by polynucleotides that express biologically active exendin analogs with agonist activity, as defined herein. For instance, exendin analogs may be peptides containing one or more amino acid substitutions, additions or deletions, compared with reference exendin, for example, exendin-4. In one embodiment, the number of substitutions, deletions, or additions is 30 amino acids or less, 25 amino acids or less, 20 amino acids or less, 15 amino acids or less, 10 amino acids or less, 5 amino acids or less or any integer between 30 and 1, inclusive. In one aspect of the invention, the substitutions include one or more conservative substitutions. A "conservative" substitution denotes the replacement of an amino acid residue by another, biologically active, similar residue. Examples of conservative substitutions include the substitution of one hydrophobic residue, such as isoleucine, valine, leucine, or methionine for another, or the substitution of one polar residue for another, such as the substitution of arginine for lysine, glutamic for aspartic acids, or glutamine for asparagine, and the like. The following table lists illustrative, but non-limiting, conservative amino acid substitutions.

TABLE 2

| ORIGINAL RESIDUE | EXEMPLARY SUBSTITUTIONS |
|---|---|
| ALA | SER, THR |
| ARG | LYS |
| ASN | HIS, SER |
| ASP | GLU, ASN |
| CYS | SER |
| GLN | ASN, HIS |
| GLU | ASP |
| GLY | ALA, SER |
| HIS | ASN, GLN |
| ILE | LEU, VAL, THR |
| LEU | ILE, VAL |
| LYS | ARG, GLN, GLU, THR |
| MET | LEU, ILE, VAL |
| PHE | LEU, TYR |
| SER | THR, ALA, ASN |
| THR | SER, ALA |
| TRP | ARG, SER |
| TYR | PHE |
| VAL | ILE, LEU, ALA |
| PRO | ALA |

It is further understood that exendin analogs include the peptides described herein which have been chemically derivatized or altered, for example, peptides with non-natural amino acid residues (e.g., taurine, β- and γ-amino acid residues and D-amino acid residues), C-terminal functional group modifications, such as amides, esters, and C-terminal ketone modifications and N-terminal functional group modifications, such as acylated amines, Schiff bases, or cyclization, as found, for example, in the amino acid pyroglutamic acid.

Such derivativatized peptides include exendins, exendin agonists and exendin analog agonists conjugated to one or more polymer molecules, such as polyethylene glycol ("PEG") or fatty acid chains of various lengths (e.g., stearyl, palmitoyl, octanoyl, etc.), or by the addition of polyamino acids, such as poly-his, poly-arg, poly-lys, and poly-ala. Modifications to the exendins, exendin agonists and exendin analog agonists can also include small molecule substituents, such as short alkyls and constrained alkyls (e.g., branched, cyclic, fused, adamantyl), and aromatic groups. The polymer molecules will typically have a molecular weight ranging from about 500 to about 20,000 Daltons.

Such polymer-conjugations and small molecule substituent modifications may occur singularly at the N- or C-terminus or at the side chains of amino acid residues within the sequence of the polypeptides. Alternatively, there may be multiple sites of derivatization along the hybrid polypeptide. Substitution of one or more amino acids with lysine, aspartic acid, glutamic acid, or cysteine may provide additional sites for derivatization. See, e.g., U.S. Pat. Nos. 5,824,784 and 5,824,778. In one embodiment, the polypeptides may be conjugated to one, two, or three polymer molecules.

The polymer molecules may be linked to an amino, carboxyl, or thiol group, and may be linked by N or C terminus, or at the side chains of lysine, aspartic acid, glutamic acid, or cysteine. Alternatively, the polymer molecules may be linked with diamine and dicarboxylic groups. In one embodiment, the polypeptides are conjugated to one, two, or three PEG molecules through an epsilon amino group on a lysine amino acid.

Also included in the present invention are exendin analog sequences having greater than 50% sequence identity, greater than 60% sequence identity, greater than 70% sequence identity, greater than 80% sequence identity, greater than 90% sequence identity, greater than 95% sequence identity, greater than 97% sequence identity or any percent identity between 50% and 97%, to a reference exendin peptide, for example, (1) SEQ ID NOS: 1 and 2; and (2) to truncated sequences thereof, wherein said truncated sequences containing at least 10 amino acids, at least 20 amino acids, at least 25 amino acids, at least 30 amino acids, at least 35 amino acids, at least 38 amino acids or N−1 amino acids where N equals the number of amino acids in the full length or reference peptide or protein. As used herein, sequence identity refers to a comparison made between two molecules using standard algorithms well known in the art. In one embodiment, the algorithm for calculating sequence identity for the present invention is the Smith-Waterman algorithm, where an exendin, for example SEQ ID NO:1 [i.e., exendin-4], is used as the reference sequence to define the percentage identity of a comparison peptide over its length. The choice of parameter values for matches, mismatches, and insertions or deletions is discretionary, although some parameter values have been found to yield more biologically realistic results than others. In one embodiment, the set of parameter values for the Smith-Waterman algorithm is set forth in the "maximum similarity segments" approach, which uses values of 1 for a matched residue and −⅓ for a mismatched residue (a residue being either a single nucleotide or single amino acid). Waterman, *Bull. Math. Biol.* 46; 473 (1984). Insertions and deletions (indels), x, are weighted as $x_k = \frac{1}{3} k$, where k is the number of residues in a given insertion or deletion. Id.

Novel exendin analogs with agonist activity include those described in commonly owned PCT Application Serial No. PCT/US98/16387 filed Aug. 6, 1998, entitled "Novel Exendin Agonist Compounds," U.S. patent application Ser. No. 10/181,102, which claims the benefit of U.S. Patent Application Ser. No. 60/055,404, filed Aug. 8, 1997, which are herein incorporated by reference.

Other novel exendin analogs with agonist activity include those described in commonly owned PCT Application Serial No. PCT/US98/24210, filed Nov. 13, 1998, entitled "Novel Exendin Agonist Compounds," U.S. patent application Ser. No. 09/554,533, which claims the benefit of U.S. Provisional Application No. 60/065,442 filed Nov. 14, 1997, which are herein incorporated by reference.

Still other novel exendin analogs with agonist activity include those described in commonly owned PCT Application Serial No. PCT/US98/24273, filed Nov. 13, 1998, entitled "Novel Exendin Agonist Compounds," U.S. patent application Ser. No. 09/554,531, which claims the benefit of U.S. Provisional Application No. 60/066,029 filed Nov. 14, 1997, which are herein incorporated by reference.

Still other exendin analogs with agonist activity include those described in commonly owned PCT Application Serial No. PCT/US97/14199, filed Aug. 8, 1997, entitled "Methods for Regulating Gastrointestinal Activity," U.S. patent application Ser. No. 08/908,867, which is a continuation-in-part of U.S. patent application Ser. No. 08/694,954 filed Aug. 8, 1996, which are hereby incorporated by reference.

Still other exendin analogs with agonist activity include those described in commonly owned PCT Application Serial No. PCT/US98/00449, filed Jan. 7, 1998, entitled "Use of Exendins and Agonists Thereof for the Reduction of Food Intake," U.S. patent application Ser. No. 09/003,869, which claims priority to U.S. Provisional Application No. 60/034,90 filed Jan. 7, 1997, which are hereby incorporated by reference.

Still other exendin analogs with agonist activity include those described in commonly owned PCT Application Serial No. PCT/US01/00719, filed Jan. 9, 2001, entitled "Use of Exendins and Agonists Thereof for Modulation of Triglyceride Levels and Treatment of Dyslipidemia," U.S. patent application Ser. No. 09/756,690, which claims priority to U.S. Provisional Application No. 60/175,365 filed Jan. 10, 2000, which are hereby incorporated by reference.

Still other exendin analogs with agonist activity include those described in commonly owned PCT Application Serial No. PCT/US00/00902, filed Jan. 14, 2000, entitled "Novel Exendin Agonist Formulations and Methods of Administration Thereof," U.S. patent application Ser. No. 09/889,330, which claims priority to U.S. Provisional Application No. 60/116,380 filed Jan. 14, 1999, which are hereby incorporated by reference.

Still other exendin analogs with agonist activity include those described in commonly owned PCT Application Serial No. PCT/US03/16699, filed May 28, 2003, entitled "Novel Exendin Agonist Formulations and Methods of Administration Thereof," U.S. patent application Ser. No. 10/522,103, which claims priority to U.S. application Ser. No. 10/157,224 filed May 28, 2002, which are hereby incorporated by reference.

Still other exendin analogs with agonist activity include those described in commonly owned PCT Application Serial No. PCT/US00/00942, filed Jan. 14, 2000, entitled "Methods of Glucagon Suppression," U.S. patent application Ser. No. 09/889,331, which claims priority to U.S. Provisional Application No. 60/132,017 filed Apr. 30, 1999, which are hereby incorporated by reference.

Still other exendin analogs with agonist activity include those described in commonly owned PCT Application Serial No. PCT/US00/14231, filed May 23, 2000, entitled "Use of Exendins and Agonists Thereof for the Treatment of Gestational Diabetes Mellitus," which claims priority to U.S. application Ser. No. 09/323,867 filed Jun. 1, 1999, which are hereby incorporated by reference.

Still other exendin analogs with agonist activity include those described in commonly owned PCT Application Serial No. PCT/US99/02554, filed Feb. 5, 1999, entitled "Inotropic and Diuretic Effects of Exendin and GLP-1," U.S. patent application Ser. No. 09/622,105, which claims priority to U.S. Provisional Application No. 60/075,122 filed Feb. 13, 1998, which are hereby incorporated by reference.

Still other exendin analogs with agonist activity include those described in commonly owned PCT Application Serial No. PCT/US05/04178 filed Feb. 11, 2005, entitled "Hybrid Polypeptides with Selectable Properties," U.S. patent application Ser. No. 11/055,093 which are hereby incorporated by reference.

Activity of exendin agonists and exendin analog agonist can be indicated, for example, by activity in the assays described herein. Effects of exendins or exendin agonists on body weight and body composition can be identified, evaluated, or screened for, using the methods described herein, or other art-known or equivalent methods for determining effect on body weight BMI, body composition blood glucose, $HbA_{1c}$, etc.

Certain exemplary exendin analogs with agonist activity include: exendin-4 (1-30) [SEQ ID NO:9: His Gly Glu Gly Thr Phe Thr Ser Asp Leu Ser Lys Gln Met Glu Glu Glu Ala Val Arg Leu Phe Ile Glu Trp Leu Lys Asn Gly Gly]; exendin-4 (1-30) amide [SEQ ID NO:10: His Gly Glu Gly Thr Phe Thr Ser Asp Leu Ser Lys Gln Met Glu Glu Glu Ala Val Arg Leu Phe Ile Glu Tip Leu Lys Asn Gly Gly-$NH_2$]; exendin-4 (1-28) amide [SEQ ID NO:11: His Gly Glu Gly Thr Phe Thr Ser Asp Leu Ser Lys Gln Met Glu Glu Glu Ala Val Arg Leu Phe Ile Glu Trp Leu Lys Asn-$NH_2$]; $^{14}$Leu,$^{25}$Phe exendin-4 amide [SEQ ID NO:12: His Gly Glu Gly Thr Phe Thr Ser Asp Leu Ser Lys Gln Leu Glu Glu Glu Ala Val Arg Leu Phe Ile Glu Phe Leu Lys Asn Gly Gly Pro Ser Ser Gly Ala Pro Pro Pro Ser-$NH_2$]; $^{14}$Leu,$^{25}$Phe exendin-4 (1-28) amide [SEQ ID NO:13: His Gly Glu Gly Thr Phe Thr Ser Asp Leu Ser Lys Gln Leu Glu Glu Glu Ala Val Arg Leu Phe Ile Glu Phe Leu Lys Asn-$NH_2$]; and $^{14}$Leu,$^{22}$Ala,$^{25}$Phe exendin-4 (1-28) amide [SEQ ID NO:14: His Gly Glu Gly Thr Phe Thr Ser Asp Leu Ser Lys Gln Leu Glu Glu Glu Ala Val Arg Leu Ala Ile Glu Phe Leu Lys Asn-$NH_2$].

Also included within the scope of the present invention are pharmaceutically acceptable salts of the compounds of formulae I-VIII and pharmaceutical compositions including said compounds and salts thereof.

Formula I

Exendin analogs with agonist activity also include those described in U.S. Provisional Application No. 60/065,442, now U.S. patent application Ser. No. 09/554,533, including compounds of the formula (I) [SEQ ID NO:15]:

```
Xaa1 Xaa2 Xaa3 Gly Xaa5 Xaa6 Xaa7 Xaa8 Xaa9

Xaa10 Xaa11 Xaa12 Xaa13 Xaa14 Xaa15 Xaa16 Xaa17

Ala Xaa19 Xaa20 Xaa21 Xaa22 Xaa23 Xaa24 Xaa25

Xaa26 Xaa27 Xaa28-Z1;
``` wherein
$Xaa_1$ is His, Arg or Tyr;
$Xaa_2$ is Ser, Gly, Ala or Thr;
$Xaa_3$ is Ala, Asp or Glu;
$Xaa_5$ is Ala or Thr;
$Xaa_6$ is Ala, Phe, Tyr or naphthylalanine;
$Xaa_7$ is Thr or Ser;
$Xaa_8$ is Ala, Ser or Thr;
$Xaa_9$ is Asp or Glu;
$Xaa_{10}$ is Ala, Leu, Ile, Val, pentylglycine or Met;
$Xaa_{11}$ is Ala or Ser;
$Xaa_{12}$ is Ala or Lys;
$Xaa_{13}$ is Ala or Gln;
$Xaa_{14}$ is Ala, Leu, Ile, pentylglycine, Val or Met;
$Xaa_{15}$ is Ala or Glu;
$Xaa_{16}$ is Ala or Glu;
$Xaa_{17}$ is Ala or Glu;
$Xaa_{19}$ is Ala or Val;
$Xaa_{20}$ is Ala or Arg;
$Xaa_{21}$ is Ala or Leu;
$Xaa_{22}$ is Ala, Phe, Tyr or naphthylalanine;
$Xaa_{23}$ is Ile, Val, Leu, pentylglycine, tert-butylglycine or Met;
$Xaa_{24}$ is Ala, Glu or Asp;
$Xaa_{25}$ is Ala, Trp, Phe, Tyr or naphthylalanine;
$Xaa_{26}$ is Ala or Leu;
$Xaa_{27}$ is Ala or Lys;
$Xaa_{28}$ is Ala or Asn;
$Z_1$ is —OH,

—$NH_2$

Gly-$Z_2$,

Gly Gly-$Z_2$,

Gly Gly $Xaa_{31}$-$Z_2$,

Gly Gly $Xaa_{31}$ Ser-$Z_2$,

Gly Gly $Xaa_{31}$ Ser Ser-$Z_2$,

Gly Gly $Xaa_{31}$ Ser Ser Gly-$Z_2$,

Gly Gly $Xaa_{31}$ Ser Ser Gly Ala-$Z_2$,

Gly Gly $Xaa_{31}$ Ser Ser Gly Ala $Xaa_{36}$-$Z_2$,

Gly Gly $Xaa_{31}$ Ser Ser Gly Ala $Xaa_{36}$ $Xaa_{37}$-$Z_2$ or

Gly Gly $Xaa_{31}$ Ser Ser Gly Ala $Xaa_{36}$ $Xaa_{37}$ $Xaa_{38}$-$Z_2$;

$Xaa_{31}$, $Xaa_{36}$, $Xaa_{37}$ and $Xaa_{38}$ are independently Pro, homoproline, 3Hyp, 4Hyp, thioproline, N-alkylglycine, N-alkylpentylglycine or N-alkylalanine; and $Z_2$ is —OH or —$NH_2$;

provided that no more than three of $Xaa_3$, $Xaa_5$, $Xaa_6$, $Xaa_8$, $Xaa_{10}$, $Xaa_{11}$, $Xaa_{12}$, $Xaa_{13}$, $Xaa_{14}$, $Xaa_{15}$, $Xaa_{16}$, $Xaa_{17}$, $Xaa_{19}$, $Xaa_{20}$, $Xaa_{21}$, $Xaa_{24}$, $Xaa_{25}$, $Xaa_{26}$, $Xaa_{27}$ and $Xaa_{28}$ are Ala.

Exemplary N-alkyl groups for N-alkylglycine, N-alkylpentylglycine and N-alkylalanine include lower alkyl groups, for example, of 1 to about 6 carbon atoms, or of 1 to 4 carbon atoms.

Exemplary exendin analogs include those wherein $Xaa_1$ is His or Tyr. More preferably $Xaa_1$ is His.

Provided are those compounds wherein $Xaa_2$ is Gly.

Provided are those compounds wherein $Xaa_{14}$ is Leu, pentylglycine or Met.

Exemplary compounds are those wherein $Xaa_{25}$ is Trp or Phe.

Exemplary compounds are those where $Xaa_6$ is Phe or naphthylalanine; $Xaa_{22}$ is Phe or naphthylalanine and $Xaa_{23}$ is Ile or Val.

Provided are compounds wherein $Xaa_{31}$, $Xaa_{36}$, $Xaa_{37}$ and $Xaa_{38}$ are independently selected from Pro, homoproline, thioproline and N-alkylalanine.

Preferably $Z_1$ is —$NH_2$.
Preferably $Z_2$ is —$NH_2$.

According to one embodiment, provided are compounds of formula (I) wherein $Xaa_1$ is His or Tyr, more preferably His; $Xaa_2$ is Gly; $Xaa_6$ is Phe or naphthylalanine; $Xaa_{14}$ is Leu, pentylglycine or Met; $Xaa_{22}$ is Phe or naphthylalanine; $Xaa_{23}$ is Ile or Val; $Xaa_{31}$, $Xaa_{36}$, $Xaa_{37}$ and $Xaa_{38}$ are independently selected from Pro, homoproline, thioproline or N-alkylalanine. More preferably $Z_1$ is —$NH_2$.

According to one embodiment, exemplary compounds include those of formula (I) wherein: $Xaa_1$ is His or Arg; $Xaa_2$ is Gly or Ala; $Xaa_3$ is Asp or Glu; $Xaa_5$ is Ala or Thr; $Xaa_6$ is Ala, Phe or nephthylalaine; $Xaa_7$ is Thr or Ser; $Xaa_8$ is Ala, Ser or Thr; $Xaa_9$ is Asp or Glu; $Xaa_{10}$ is Ala, Leu or pentylglycine; $Xaa_{11}$ is Ala or Ser; $Xaa_{12}$ is Ala or Lys; $Xaa_{13}$ is Ala or Gln; $Xaa_{14}$ is Ala, Leu or pentylglycine; $Xaa_{15}$ is Ala or Glu; $Xaa_{16}$ is Ala or Glu; $Xaa_{17}$ is Ala or Glu; $Xaa_{19}$ is Ala or Val; $Xaa_{20}$ is Ala or Arg; $Xaa_{21}$ is Ala or Leu; $Xaa_{22}$ is Phe or naphthylalanine; $Xaa_{23}$ is Ile, Val or tert-butylglycine; $Xaa_{24}$ is Ala, Glu or Asp; $Xaa_{25}$ is Ala, Trp or Phe; $Xaa_{26}$ is Ala or Leu; $Xaa_{27}$ is Ala or Lys; $Xaa_{28}$ is Ala or Asn; $Z_1$ is —OH, —NH$_2$, Gly-$Z_2$, Gly Gly-$Z_2$, Gly Gly $Xaa_{31}$-$Z_2$, Gly Gly $Xaa_{31}$ Ser-$Z_2$, Gly Gly $Xaa_{31}$ Ser Ser-$Z_2$, Gly Gly $Xaa_{31}$ Ser Ser Gly-$Z_2$, Gly Gly $Xaa_{31}$ Ser Ser Gly Ala-$Z_2$, Gly Gly $Xaa_{31}$ Ser Ser Gly Ala $Xaa_{36}$-$Z_2$, Gly Gly $Xaa_{31}$ Ser Ser Gly Ala $Xaa_{36}$ $Xaa_{37}$-$Z_2$, Gly Gly $Xaa_{31}$ Ser Ser Gly Ala $Xaa_{36}$ $Xaa_{37}$ $Xaa_{38}$-$Z_2$; $Xaa_{31}$, $Xaa_{36}$, $Xaa_{37}$ and $Xaa_{38}$ being independently Pro homoproline, thioproline or N-methylalanine; and $Z_2$ being —OH or —NH$_2$; provided that no more than three of $Xaa_3$, $Xaa_5$, $Xaa_6$, $Xaa_8$, $Xaa_{10}$, $Xaa_{11}$, $Xaa_{12}$, $Xaa_{13}$, $Xaa_{14}$, $Xaa_{15}$, $Xaa_{16}$, $Xaa_{17}$, $Xaa_{19}$, $Xaa_{20}$, $Xaa_{21}$, $Xaa_{24}$, $Xaa_{25}$, $Xaa_{26}$, $Xaa_{27}$ and $Xaa_{28}$ are Ala. Other exemplary compounds include those set forth in PCT application Serial No. PCT/US98/24210, filed Nov. 13, 1998, entitled "Novel Exendin Agonist Compounds" identified therein as compounds 2-23.

According to another embodiment, provided are compounds where $Xaa_{14}$ is Leu, Ile, Val or pentylglycine, more preferably Leu or pentylglycine, and $Xaa_{25}$ is Phe, Tyr or naphthylalanine, more preferably Phe or naphthylalanine. These compounds will be less susceptive to oxidative degradation, both in vitro and in vivo, as well as during synthesis of the compound.

Formula II

Exendin analogs with agonist activity also include those described in U.S. Provisional Application No. 60/066,029, now U.S. patent application Ser. No. 09/554,531, including compounds of the formula (II)[SEQ ID NO:16]:

$Xaa_1$ $Xaa_2$ $Xaa_3$ $Xaa_4$ $Xaa_5$ $Xaa_6$ $Xaa_7$ $Xaa_8$ $Xaa_9$ $Xaa_{10}$ $Xaa_{11}$ $Xaa_{12}$ $Xaa_{13}$ $Xaa_{14}$ $Xaa_{15}$ $Xaa_{16}$ $Xaa_{17}$

Ala $Xaa_{19}$ $Xaa_{20}$ $Xaa_{21}$ $Xaa_{22}$ $Xaa_{23}$ $Xaa_{24}$ $Xaa_{25}$ $Xaa_{26}$ $Xaa_{27}$ $Xaa_{28}$-$Z_1$;

wherein:
$Xaa_1$ is His, Arg, Tyr, Ala, Norval, Val or Norleu;
$Xaa_2$ is Ser, Gly, Ala or Thr;
$Xaa_3$ is Ala, Asp or Glu;
$Xaa_4$ is Ala, Norval, Val, Norleu or Gly;
$Xaa_5$ is Ala or Thr;
$Xaa_6$ is Ala, Phe, Tyr or naphthylalanine;
$Xaa_7$ is Thr or Ser;
$Xaa_8$ is Ala, Ser or Thr;
$Xaa_9$ is Ala, Norval, Val, Norleu, Asp or Glu;
$Xaa_{10}$ is Ala, Leu, Ile, Val, pentylglycine or Met;
$Xaa_{11}$ is Ala or Ser;
$Xaa_{12}$ is Ala or Lys;
$Xaa_{13}$ is Ala or Gln;
$Xaa_{14}$ is Ala, Leu, Ile, pentylglycine, Val or Met;
$Xaa_{15}$ is Ala or Glu;
$Xaa_{16}$ is Ala or Glu;
$Xaa_{17}$ is Ala or Glu;
$Xaa_{19}$ is Ala or Val;
$Xaa_{20}$ is Ala or Arg;
$Xaa_{21}$ is Ala or Leu;
$Xaa_{22}$ is Phe, Tyr or naphthylalanine;
$Xaa_{23}$ is Ile, Val, Leu, pentylglycine, tert-butylglycine or Met;
$Xaa_{24}$ is Ala, Glu or Asp;
$Xaa_{25}$ is Ala, Trp, Phe, Tyr or naphthylalanine;
$Xaa_{26}$ is Ala or Leu;
$Xaa_{27}$ is Ala or Lys;
$Xaa_{28}$ is Ala or Asn;
$Z_1$ is —OH,

—NH$_2$,

Gly-$Z_2$,

Gly Gly-$Z_2$,

Gly Gly $Xaa_{31}$-$Z_2$,

Gly Gly $Xaa_{31}$ Ser-$Z_2$,

Gly Gly $Xaa_{31}$ Ser Ser-$Z_2$,

Gly Gly $Xaa_{31}$ Ser Ser Gly-$Z_2$,

Gly Gly $Xaa_{31}$ Ser Ser Gly Ala-$Z_2$,

Gly Gly $Xaa_{31}$ Ser Ser Gly Ala $Xaa_{36}$-$Z_2$,

Gly Gly $Xaa_{31}$ Ser Ser Gly Ala $Xaa_{36}$ $Xaa_{37}$-$Z_2$,

Gly Gly $Xaa_{31}$ Ser Ser Gly Ala $Xaa_{36}$ $Xaa_{37}$ $Xaa_{38}$-$Z_2$ or

Gly Gly $Xaa_{31}$ Ser Ser Gly Ala $Xaa_{36}$ $Xaa_{37}$ $Xaa_{38}$ $Xaa_{39}$-$Z_2$;

$Xaa_{31}$, $Xaa_{36}$, $Xaa_{37}$ and $Xaa_{38}$ are independently Pro, homoproline, 3Hyp, 4Hyp, thioproline, N-alkylglycine, N-alkylpentylglycine or N-alkylalanine;

$Xaa_{39}$ is Ser or Tyr; and $Z_2$ is —OH or —NH$_2$;

provided that no more than three of $Xaa_3$, $Xaa_4$, $Xaa_5$, $Xaa_6$, $Xaa_8$, $Xaa_9$, $Xaa_{10}$, $Xaa_{11}$, $Xaa_{12}$, $Xaa_{13}$, $Xaa_{14}$, $Xaa_{15}$, $Xaa_{16}$, $Xaa_{17}$, $Xaa_{19}$, $Xaa_{20}$, $Xaa_{21}$, $Xaa_{24}$, $Xaa_{25}$, $Xaa_{26}$, $Xaa_{27}$ and $Xaa_{28}$ are Ala; and provided also that, if $Xaa_1$ is His, Arg or Tyr, then at least one of $Xaa_3$, $Xaa_4$ and $Xaa_9$ is Ala.

Exemplary N-alkyl groups for N-alkylglycine, N-alkylpentylglycine and N-alkylalanine include lower alkyl groups, for example, of 1 to about 6 carbon atoms, or of 1 to 4 carbon atoms. Suitable compounds of formula (II) include those described in application Serial No. PCT/US98/24273, filed Nov. 13, 1998, entitled "Novel Exendin Agonist Compounds," U.S. patent application Ser. No. 09/554,531.

In one embodiment, such exendin analogs include those wherein $Xaa_1$ is His, Ala or Norval. More preferably $Xaa_1$ is His or Ala. Most preferably $Xaa_1$ is His.

Provided are those compounds of formula (II) wherein $Xaa_2$ is Gly.

Provided are those compounds of formula (II) wherein $Xaa_3$ is Ala.

Provided are those compounds of formula (II) wherein $Xaa_4$ is Ala.

Provided are those compounds of formula (II) wherein $Xaa_9$ is Ala.

Provided are those compounds of formula (II) wherein $Xaa_{14}$ is Leu, pentylglycine or Met.

Exemplary compounds of formula (II) are those wherein $Xaa_{25}$ is Trp or Phe.

Exemplary compounds of formula (II) are those where $Xaa_6$ is Ala, Phe or naphthylalanine; $Xaa_{22}$ is Phe or naphthylalanine; and $Xaa_{23}$ is Ile or Val.

Provided are compounds of formula (II) wherein $Xaa_{31}$, $Xaa_{36}$, $Xaa_{37}$ and $Xaa_{38}$ are independently selected from Pro, homoproline, thioproline and N-alkylalanine.

Preferably $Z_1$ is —NH$_2$.

Preferably $Z_2$ is —NH$_2$.

According to one embodiment, provided are compounds of formula (II) wherein $Xaa_1$ is Ala, His or Tyr, more preferably Ala or His; $Xaa_2$ is Ala or Gly; $Xaa_6$ is Phe or naphthylalanine; $Xaa_{14}$ is Ala, Leu, pentylglycine or Met; $Xaa_{22}$ is Phe or naphthylalanine; $Xaa_{23}$ is Ile or Val; $Xaa_{31}$, $Xaa_{36}$, $Xaa_{37}$ and $Xaa_{38}$ are independently selected from Pro, homoproline, thioproline or N-alkylalanine; and $Xaa_{39}$ is Ser or Tyr, more preferably Ser. More preferably $Z_1$ is —$NH_2$.

According to another embodiment, exemplary compounds include those of formula (II) wherein: $Xaa_1$ is His or Ala; $Xaa_2$ is Gly or Ala; $Xaa_3$ is Ala, Asp or Glu; $Xaa_4$ is Ala or Gly; $Xaa_5$ is Ala or Thr; $Xaa_6$ is Phe or naphthylalanine; $Xaa_7$ is Thr or Ser; $Xaa_8$ is Ala, Ser or Thr; $Xaa_9$ is Ala, Asp or Glu; $Xaa_{10}$ is Ala, Leu or pentylglycine; $Xaa_{11}$ is Ala or Ser; $Xaa_{12}$ is Ala or Lys; $Xaa_{13}$ is Ala or Gln; $Xaa_{14}$ is Ala, Leu, Met or pentylglycine; $Xaa_{15}$ is Ala or Glu; $Xaa_{16}$ is Ala or Glu; $Xaa_{17}$ is Ala or Glu; $Xaa_{19}$ is Ala or Val; $Xaa_{20}$ is Ala or Arg; $Xaa_{21}$ is Ala or Leu; $Xaa_{22}$ is Phe or naphthylalanine; $Xaa_{23}$ is Ile, Val or tert-butylglycine; $Xaa_{24}$ is Ala, Glu or Asp; $Xaa_{25}$ is Ala, Trp or Phe; $Xaa_{26}$ is Ala or Leu; $Xaa_{27}$ is Ala or Lys; $Xaa_{28}$ is Ala or Asn; $Z_1$ is —OH, —$NH_2$, Gly-$Z_2$, Gly Gly-$Z_2$, Gly Gly $Xaa_{31}$-$Z_2$, Gly Gly $Xaa_{31}$ Ser-$Z_2$, Gly Gly $Xaa_{31}$ Ser Ser-$Z_2$, Gly Gly $Xaa_{31}$ Ser Ser Gly-$Z_2$, Gly Gly $Xaa_{31}$ Ser Ser Gly Ala-$Z_2$, Gly Gly $Xaa_{31}$ Ser Ser Gly Ala $Xaa_{36}$-$Z_2$, Gly Gly $Xaa_{31}$ Ser Ser Gly Ala $Xaa_{36}$ $Xaa_{37}$-$Z_2$, Gly Gly $Xaa_{31}$ Ser Ser Gly Ala $Xaa_{36}$ $Xaa_{37}$ $Xaa_{38}$-$Z_2$ or Gly Gly $Xaa_{31}$ Ser Ser Gly Ala $Xaa_{36}$ $Xaa_{37}$ $Xaa_{38}$ $Xaa_{39}$-$Z_2$; $Xaa_{31}$, $Xaa_{36}$, $Xaa_{37}$ and $Xaa_{38}$ being independently Pro homoproline, thioproline or N-methylalanine; and $Z_2$ being —OH or —$NH_2$; provided that no more than three of $Xaa_3$, $Xaa_5$, $Xaa_6$, $Xaa_8$, $Xaa_{10}$, $Xaa_{11}$, $Xaa_{12}$, $Xaa_{13}$, $Xaa_{14}$, $Xaa_{15}$, $Xaa_{16}$, $Xaa_{17}$, $Xaa_{19}$, $Xaa_{20}$, $Xaa_{21}$, $Xaa_{24}$, $Xaa_{25}$, $Xaa_{26}$, $Xaa_{27}$ and $Xaa_{28}$ are Ala; and provided also that, if $Xaa_1$ is His, Arg or Tyr, then at least one of $Xaa_3$, $Xaa_4$ and $Xaa_9$ is Ala. Exemplary compounds of formula (II) include those described in application Serial No. PCT/US98/24273, filed Nov. 13, 1998, entitled "Novel Exendin Agonist Compounds" as having the amino acid sequence of SEQ ID NOS:5-93 therein which are hereby incorporated by reference.

According to still another embodiment, provided are compounds of formula (II) where $Xaa_{14}$ is Ala, Leu, Ile, Val or pentylglycine, more preferably Leu or pentylglycine, and $Xaa_{25}$ is Ala, Phe, Tyr or naphthylalanine, more preferably Phe or naphthylalanine. These compounds will be less susceptible to oxidative degration, both in vitro and in vivo, as well as during synthesis of the compound.

Formula III

Additionally, the present invention includes narrower genera of compounds described in PCT Application Serial No. PCT/US98/24210, filed Nov. 13, 1998, entitled "Novel Exendin Agonist Compounds," U.S. patent application Ser. No. 09/554,533, and having particular amino acid sequences, for example, compounds of the formula (III) [SEQ ID NO:17]:

$Xaa_1$ $Xaa_2$ $Xaa_3$ Gly $Xaa_5$ $Xaa_6$ $Xaa_7$ $Xaa_8$ $Xaa_9$ $Xaa_{10}$ $Xaa_{11}$ $Xaa_{12}$ $Xaa_{13}$ $Xaa_{14}$ $Xaa_{15}$ $Xaa_{16}$ $Xaa_{17}$

Ala $Xaa_{19}$ $Xaa_{20}$ $Xaa_{21}$ $Xaa_{22}$ $Xaa_{23}$ $Xaa_{24}$ $Xaa_{25}$ $Xaa_{26}$ $Xaa_{27}$ $Xaa_{28}$-$Z_1$;

wherein:
$Xaa_1$ is His or Arg;
$Xaa_2$ is Gly or Ala;
$Xaa_3$ is Ala, Asp or Glu;
$Xaa_5$ is Ala or Thr;
$Xaa_6$ is Ala, Phe or naphthylalanine;
$Xaa_7$ is Thr or Ser;
$Xaa_8$ is Ala, Ser or Thr;
$Xaa_9$ is Asp or Glu;
$Xaa_{10}$ is Ala, Leu or pentylglycine;
$Xaa_{11}$ is Ala or Ser;
$Xaa_{12}$ is Ala or Lys;
$Xaa_{13}$ is Ala or Gln;
$Xaa_{14}$ is Ala, Leu or pentylglycine;
$Xaa_{15}$ is Ala or Glu;
$Xaa_{16}$ is Ala or Glu;
$Xaa_{17}$ is Ala or Glu;
$Xaa_{19}$ is Ala or Val;
$Xaa_{20}$ is Ala or Arg;
$Xaa_{21}$ is Ala or Leu;
$Xaa_{22}$ is Phe or naphthylalanine;
$Xaa_{23}$ is Ile, Val or tert-butylglycine;
$Xaa_{24}$ is Ala, Glu or Asp;
$Xaa_{25}$ is Ala, Trp, or Phe;
$Xaa_{26}$ is Ala or Leu;
$Xaa_{27}$ is Ala or Lys;
$Xaa_{28}$ is Ala or Asn;
$Z_1$ is —OH,

—$NH_2$,

Gly-$Z_2$,

Gly Gly-$Z_2$,

Gly Gly $Xaa_{31}$-$Z_2$,

Gly Gly $Xaa_{31}$ Ser-$Z_2$,

Gly Gly $Xaa_{31}$ Ser Ser-$Z_2$,

Gly Gly Xaa31 Ser Ser Gly-$Z_2$,

Gly Gly $Xaa_{31}$ Ser Ser Gly Ala-$Z_2$,

Gly Gly $Xaa_{31}$ Ser Ser Gly Ala $Xaa_{36}$-$Z_2$,

Gly Gly $Xaa_{31}$ Ser Ser Gly Ala $Xaa_{36}$ $Xaa_{37}$-$Z_2$
or

Gly Gly $Xaa_{31}$ Ser Ser Gly Ala $Xaa_{36}$ $Xaa_{37}$ $Xaa_{38}$-$Z_2$;

$Xaa_{31}$, $Xaa_{36}$, $Xaa_{37}$ and $Xaa_{38}$ are independently selected from the group consisting of Pro, homoproline, thioproline and N-methylalanine; and $Z_2$ is —OH or —$NH_2$;

provided that no more than three of $Xaa_3$, $Xaa_5$, $Xaa_6$, $Xaa_8$, $Xaa_{10}$, $Xaa_{11}$, $Xaa_{12}$, $Xaa_{13}$, $Xaa_{14}$, $Xaa_{15}$, $Xaa_{16}$, $Xaa_{17}$, $Xaa_{19}$, $Xaa_{20}$, $Xaa_{21}$, $Xaa_{24}$, $Xaa_{25}$, $Xaa_{26}$, $Xaa_{27}$ and $Xaa_{28}$ are Ala; and pharmaceutically acceptable salts thereof.

Formula IV

Additionally, the present invention includes narrower genera of peptide compounds described in PCT Application Serial No. PCT/US98/24273, filed Nov. 13, 1998, entitled "Novel Exendin Agonist Compounds," U.S. patent application Ser. No. 09/554,531, as having particular amino acid sequences, for example, compounds of the formula [IV] [SEQ ID NO:18]:

$Xaa_1$ $Xaa_2$ $Xaa_3$ $Xaa_5$ $Xaa_5$ $Xaa_6$ $Xaa_7$ $Xaa_8$ $Xaa_9$ $Xaa_{10}$ $Xaa_{11}$ $Xaa_{12}$ $Xaa_{13}$ $Xaa_{14}$ $Xaa_{15}$ $Xaa_{16}$ $Xaa_{17}$

Ala $Xaa_{19}$ $Xaa_{20}$ $Xaa_{21}$ $Xaa_{22}$ $Xaa_{23}$ $Xaa_{24}$ $Xaa_{25}$ $Xaa_{26}$ $Xaa_{27}$ $Xaa_{28}$-$Z_1$;

wherein:
Xaa$_1$ is His or Ala;
Xaa$_2$ is Gly or Ala;
Xaa$_3$ is Ala, Asp or Glu;
Xaa$_4$ is Ala or Gly;
Xaa$_5$ is Ala or Thr;
Xaa$_6$ is Ala, Phe or naphthylalanine;
Xaa$_7$ is Thr or Ser;
Xaa$_8$ is Ala, Ser or Thr;
Xaa$_9$ is Ala, Asp or Glu;
Xaa$_{10}$ is Ala, Leu or pentylglycine;
Xaa$_{11}$ is Ala or Ser;
Xaa$_{12}$ is Ala or Lys;
Xaa$_{13}$ is Ala or Gln;
Xaa$_{14}$ is Ala, Leu, Met or pentylglycine;
Xaa$_{15}$ is Ala or Glu;
Xaa$_{16}$ is Ala or Glu;
Xaa$_{17}$ is Ala or Glu;
Xaa$_{19}$ is Ala or Val;
Xaa$_{20}$ is Ala or Arg;
Xaa$_{21}$ is Ala or Leu;
Xaa$_{22}$ is Phe or naphthylalanine;
Xaa$_{23}$ is Ile, Val or tert-butylglycine;
Xaa$_{24}$ is Ala, Glu or Asp;
Xaa$_{25}$ is Ala, Trp or Phe;
Xaa$_{26}$ is Ala or Leu;
Xaa$_{27}$ is Ala or Lys;
Xaa$_{28}$ is Ala or Asn;
Z$_1$ is —OH,

—NH$_2$,

Gly-Z$_2$,

Gly Gly-Z$_2$

Gly Gly Xaa$_{31}$-Z$_2$,

Gly Gly Xaa$_{31}$ Ser-Z$_2$,

Gly Gly Xaa$_{31}$ Ser Ser-Z$_2$,

Gly Gly Xaa$_{31}$ Ser Ser Gly-Z$_2$,

Gly Gly Xaa$_{31}$ Ser Ser Gly Ala-Z$_2$,

Gly Gly Xaa$_{31}$ Ser Ser Gly Ala Xaa$_{36}$-Z$_2$,

Gly Gly Xaa$_{31}$ Ser Ser Gly Ala Xaa$_{36}$ Xaa$_{37}$-Z$_2$

Gly Gly Xaa$_{31}$ Ser Ser Gly Ala Xaa$_{36}$ Xaa$_{37}$ Xaa$_{38}$-Z$_2$

Gly Gly Xaa$_{31}$ Ser Ser Gly Ala Xaa$_{36}$ Xaa$_{37}$ Xaa$_{38}$ Ser-Z$_2$;

Xaa$_{31}$, Xaa$_{36}$, Xaa$_{37}$ and Xaa$_{38}$ are independently Pro, homoproline, thioproline, or N-methylalanine; and
Z$_2$ is —OH or —NH$_2$;
provided that no more than three of Xaa$_3$, Xaa$_5$, Xaa$_6$, Xaa$_8$, Xaa$_{10}$, Xaa$_{11}$, Xaa$_{12}$, Xaa$_{13}$, Xaa$_{14}$, Xaa$_{15}$, Xaa$_{16}$, Xaa$_{17}$, Xaa$_{19}$, Xaa$_{20}$, Xaa$_{21}$, Xaa$_{24}$, Xaa$_{25}$, Xaa$_{26}$, Xaa$_{27}$, and Xaa$_{28}$ are Ala; and provided that, if Xaa$_1$ is His, Arg or Tyr, then at least one of Xaa$_3$, Xaa$_4$ and Xaa$_9$ is Ala; and pharmaceutically acceptable salts thereof.

Exemplary compounds of formula (IV) include those wherein Xaa$_1$ is His or Ala. Preferably, Xaa$_1$ is His.

Exemplary compounds of formula (IV) include those wherein Xaa$_2$ is Gly.

Exemplary compounds of formula (IV) include those wherein Xaa$_4$ is Ala.

Exemplary compounds of formula (IV) include those wherein Xaa$_9$ is Ala.

Exemplary compounds of formula (IV) include those wherein Xaa$_{14}$ is Leu, pentylglycine or Met.

Exemplary compounds of formula (IV) include those wherein Xaa$_{25}$ is Trp or Phe.

Exemplary compounds of formula (IV) include those wherein Xaa$_6$ is Ala, Phe or naphthylalanine; Xaa$_{22}$ is Phe or naphthylalanine; and Xaa$_{23}$ is Ile or Val.

Exemplary compounds of formula (IV) include those wherein Z$_1$ is —NH$_2$.

Exemplary compounds of formula (IV) include those wherein Xaa$_{31}$, Xaa$_{36}$, Xaa$_{37}$ and Xaa$_{38}$ are independently selected from the group consisting of Pro, homoproline, thioproline and N-alkylalanine.

Exemplary compounds of formula (IV) include those wherein Z$_2$ is —NH$_2$.

Exemplary compounds of formula (IV) include those wherein Z$_1$ is —NH$_2$.

Formula V

Also provided are compounds described in PCT application PCT/US98/24210, filed Nov. 13, 1998, entitled "Novel Exendin Agonist Compounds", U.S. patent application Ser. No. 09/554,533, including compounds of the formula (V) [SEQ ID NO:19]:

Xaa$_1$ Xaa$_2$ Xaa$_3$ Gly Xaa$_5$ Xaa$_6$ Xaa$_7$ Xaa$_8$ Xaa$_9$

Xaa$_{10}$ Xaa$_{11}$ Xaa$_{12}$ Xaa$_{13}$ Xaa$_{14}$ Xaa$_{15}$ Xaa$_{16}$ Xaa$_{17}$

Ala Xaa$_{19}$ Xaa$_{20}$ Xaa$_{21}$ Xaa$_{22}$ Xaa$_{23}$ Xaa$_{24}$ Xaa$_{25}$

Xaa$_{26}$ Xaa$_{27}$ Xaa$_{28}$-Z$_1$;

wherein
Xaa$_1$ is His, Arg or Tyr or 4-imidazopropionyl;
Xaa$_2$ is Ser, Gly, Ala or Thr;
Xaa$_3$ is Ala, Asp or Glu;
Xaa$_5$ is Ala or Thr;
Xaa$_6$ is Ala, Phe, Tyr or naphthylalanine;
Xaa$_7$ is Thr or Ser;
Xaa$_8$ is Ala, Ser or Thr;
Xaa$_9$ is Asp or Glu;
Xaa$_{10}$ is Ala, Leu, Ile, Val, pentylglycine or Met;
Xaa$_{11}$ is Ala or Ser;
Xaa$_{12}$ is Ala or Lys;
Xaa$_{13}$ is Ala or Gln;
Xaa$_{14}$ is Ala, Leu, Ile, pentylglycine, Val or Met;
Xaa$_{15}$ is Ala or Glu;
Xaa$_{16}$ is Ala or Glu;
Xaa$_{17}$ is Ala or Glu;
Xaa$_{19}$ is Ala or Val;
Xaa$_{20}$ is Ala or Arg;
Xaa$_{21}$ is Ala, Leu or Lys-NH$^\epsilon$-R where R is Lys, Arg, $C_1$-$C_{10}$ straight chain or branched alkanoyl or cycloalkylalkanoyl;
Xaa$_{22}$ is Phe, Tyr or naphthylalanine;
Xaa$_{23}$ is Ile, Val, Leu, pentylglycine, tert-butylglycine or Met;
Xaa$_{24}$ is Ala, Glu or Asp;
Xaa$_{25}$ is Ala, Trp, Phe, Tyr or naphthylalanine;
Xaa$_{26}$ is Ala or Leu;
Xaa$_{27}$ is Lys, Asn, Ala or Lys-NH$^\epsilon$-R where R is Lys, Arg, $C_1$-$C_{10}$ straight chain or branched alkanoyl or cycloalkylalkanoyl;
X$_{28}$ is Lys, Asn, Ala or Lys-NH$^\epsilon$-R where R is Lys, Arg, $C_1$-$C_{10}$ straight chain or branched alkanoyl or cycloalkylalkanoyl;

Z₁ is —OH,

—NH₂,

Gly-Z₂,

Gly Gly-Z₂,

Gly Gly Xaa₃₁-Z₂,

Gly Gly Xaa₃₁ Ser-Z₂,

Gly Gly Xaa₃₁ Ser Ser-Z₂,

Gly Gly Xaa₃₁ Ser Ser Gly-Z₂,

Gly Gly Xaa₃₁ Ser Ser Gly Ala-Z₂,

Gly Gly Xaa₃₁ Ser Ser Gly Ala Xaa₃₆-Z₂,

Gly Gly Xaa₃₁ Ser Ser Gly Ala Xaa₃₆ Xaa₃₇-Z₂ or

Gly Gly Xaa₃₁ Ser Ser Gly Ala Xaa₃₆ Xaa₃₇ Xaa₃₈-Z₂;

Xaa₃₁, Xaa₃₆, Xaa₃₇ and Xaa₃₈ are independently selected from the group consisting of Pro, homoproline, 3Hyp, 4Hyp, thioproline, N-alkylglycine, N-alkylpentylglycine and N-alkylalanine; and Z₂ is —OH or —NH₂;

provided that no more than three of Xaa₃, Xaa₅, Xaa₆, Xaa₈, Xaa₁₀, Xaa₁₁, Xaa₁₂, Xaa₁₃, Xaa₁₄, Xaa₁₅, Xaa₁₆, Xaa₁₇, Xaa₁₉, Xaa₂₀, Xaa₂₁, Xaa₂₄, Xaa₂₅, and Xaa₂₆ are Ala. Also within the scope of the present invention are pharmaceutically acceptable salts of the compound of formula (V) and pharmaceutical compositions including said compounds and salts thereof.

Exemplary exendin analogs of formula (V) include those wherein Xaa₁ is His, Tyr or 4-imidazopropionyl. More preferably Xaa₁ is His.

Provided are those compounds of formula (V) wherein Xaa₁ is 4-imidazopropionyl.

Provided are those compounds of formula (V) wherein Xaa₂ is Gly.

Exemplary compounds of formula (V) are those wherein Xaa₁₄ is Leu, pentylglycine or Met.

Exemplary compounds of formula (V) are those wherein Xaa₂₅ is Trp or Phe.

According to one embodiment, provided are compounds of formula (V) wherein Xaa₆ is Phe or naphthylalanine; and Xaa₂₂ is Phe or naphthylalanine; and Xaa₂₃ is Ile or Val. More preferably, Z₁ is —NH₂. According to one embodiment, provided are compounds of formula (V) wherein Xaa₃₁, Xaa₃₆, Xaa₃₇ and Xaa₃₈ are independently selected from the group consisting of Pro, homoproline, thioproline and N-alkylalanine. Preferably, Z₂ is —NH₂.

Exemplary compounds of formula (V) include those wherein X₂₇ is Lys or Lys-NHᵋ-R where R is Lys, Arg, C₁-C₁₀ straight chain or branched alkanoyl and Xaa₂₈ is Asn or Ala. Preferred compounds of formula (V) include compounds described in PCT application Serial No. PCT/US98/24210, filed Nov. 13, 1998, entitled "Novel Exendin Agonist Compounds," U.S. patent application Ser. No. 09/554,533, and identified therein as Compound Nos. 62-69.

Provided exendin analogs include those wherein Xaa₁ is His.

Provided are those compounds of formula (V) wherein Xaa₂ is Gly.

Provided are those compounds of formula (V) wherein Xaa₃ is Ala.

Provided are those compounds of formula (V) wherein Xaa₁₄ is Leu, pentylglycine or Met.

Provided compounds of formula (V) are those wherein Xaa₂₅ is Trp or Phe.

Exemplary compounds of formula (V) are those where Xaa₆ is Ala, Phe or naphthylalanine; Xaa₂₂ is Phe or naphthylalanine; and Xaa₂₃ is Ile or Val.

Provided are compounds of formula (V) wherein Xaa₃₁, Xaa₃₆, Xaa₃₇ and Xaa₃₈ are independently selected from Pro, homoproline, thioproline and N-alkylalanine.

Preferably Z₁ is —NH₂.

Preferably Z₂ is —NH₂.

According to one embodiment, provided are compounds of formula (V) wherein Xaa₁ is His or Tyr, more preferably His; Xaa₂ is Ala or Gly; Xaa₆ is Phe or naphthylalanine; Xaa₁₄ is Ala, Leu, pentylglycine or Met; Xaa₂₂ is Phe or naphthylalanine; Xaa₂₃ is Ile or Val; Xaa₃₁, Xaa₃₆, Xaa₃₇ and Xaa₃₈ are independently selected from Pro, homoproline, thioproline or N-alkylalanine; and Xaa₃₉ is Ser or Tyr, more preferably Ser. More preferably Z₁ is —NH₂.

According to one embodiment, provided compounds include those of formula (V) wherein: Xaa₁ is His; Xaa₂ is Gly or Ala; Xaa₃ is Ala, Asp or Glu; Xaa₄ is Gly; Xaa₅ is Ala or Thr; Xaa₆ is Phe or naphthylalanine; Xaa₁₂ is Thr or Ser; Xaa₈ is Ala, Ser or Thr; Xaa₉ is Asp or Glu; Xaa₁₀ is Ala, Leu or pentylglycine; Xaa₁₁ is Ala or Ser; Xaa₁₂ is Ala or Lys; Xaa₁₃ is Ala or Gln; Xaa₁₄ is Ala, Leu, Met or pentylglycine; Xaa₁₅ is Ala or Glu; Xaa₁₆ is Ala or Glu; Xaa₁₇ is Ala or Glu; Xaa₁₉ is Ala or Val; Xaa₂₀ is Ala or Arg; Xaa₂₁ is Ala or Leu; Xaa₂₂ is Phe or naphthylalanine; Xaa₂₃ is Ile, Val or tert-butylglycine; Xaa₂₄ is Ala, Glu or Asp; Xaa₂₅ is Ala, Trp or Phe; Xaa₂₆ is Ala or Leu; Xaa₂₇ is Ala or Lys; Xaa₂₈ is Ala or Asn; Z₁ is —OH, —NH₂, Gly-Z₂, Gly Gly-Z₂, Gly Gly Xaa₃'-Z₂, Gly Gly Xaa₃₁ Ser-Z₂, Gly Gly Xaa₃₁ Ser Ser-Z₂, Gly Gly Xaa₃₁ Ser Ser Gly-Z₂, Gly Gly Xaa₃₁ Ser Ser Gly Ala-Z₂, Gly Gly Xaa₃₁ Ser Ser Gly Ala Xaa₃₆-Z₂, Gly Gly Xaa₃₁ Ser Ser Gly Ala Xaa₃₆ Xaa₃₇-Z₂, Gly Gly Xaa₃₁ Ser Ser Gly Ala Xaa₃₆ Xaa₃₇ Xaa₃₈-Z₂ or Gly Gly Xaa₃₁ Ser Ser Gly Ala Xaa₃₆ Xaa₃₇ Xaa₃₈ Xaa₃₉-Z₂; Xaa₃₁, Xaa₃₆, Xaa₃₇ and Xaa₃₈ being independently Pro homoproline, thioproline or N-methylalanine; and Z₂ being —OH or —NH₂; provided that no more than three of Xaa₃, Xaa₅, Xaa₆, Xaa₈, Xaa₁₀, Xaa₁₁, Xaa₁₂, Xaa₁₃, Xaa₁₄, Xaa₁₅, Xaa₁₆, Xaa₁₇, Xaa₁₉, Xaa₂₀, Xaa₂₁, Xaa₂₄, Xaa₂₅, Xaa₂₆, Xaa₂₇ and Xaa₂₈ are Ala; and provided also that, if Xaa₁ is His, Arg or Tyr, then at least one of Xaa₃ and Xaa₄ is Ala. Particular compounds of formula (V) include those described in PCT application Serial No. PCT/US98/24210, filed Nov. 13, 1998, entitled "Novel Exendin Agonist Compounds" and having the amino acid sequences identified therein as SEQ ID NOS:5-65 and 67-74, herein SEQ ID NOS: 23-91.

According to one embodiment, provided are compounds of formula (V) where Xaa₁₄ is Ala, Leu, Ile, Val or pentylglycine, more preferably Leu or pentylglycine, and Xaa₂₅ is Ala, Phe, Tyr or naphthylalanine, more preferably Phe or naphthylalanine. These compounds will be less susceptible to oxidative degration, both in vitro and in vivo, as well as during synthesis of the compound.

Formula VI

Also provided are peptide compounds described in PCT Application Serial No. PCT/US98/24273, filed Nov. 13, 1998, entitled "Novel Exendin Agonist Compounds", U.S. patent application Ser. No. 09/554,531, including compounds of the formula (VI) [SEQ ID NO:20]:

Xaa₁ Xaa₂ Xaa₃ Xaa₄ Xaa₅ Xaa₆ Xaa₇ Xaa₈ Xaa₉

Xaa₁₀ Xaa₁₁ Xaa₁₂ Xaa₁₃ Xaa₁₄ Xaa₁₅ Xaa₁₆ Xaa₁₇

Ala Xaa₁₉ Xaa₂₀ Xaa₂₁ Xaa₂₂ Xaa₂₃ Xaa₂₄ Xaa₂₅

Xaa₂₆ Xaa₂₇ Xaa₂₈-Z₁;

wherein
  Xaa₁ is His, Arg, Tyr, Ala, Norval, Val, Norleu or 4-imidazopropionyl;
  Xaa₂ is Ser, Gly, Ala or Thr;
  Xaa₃ is Ala, Asp or Glu;
  Xaa₄ is Ala, Norval, Val, Norleu or Gly;
  Xaa₅ is Ala or Thr;
  Xaa₆ is Ala, Phe, Tyr or naphthylalanine;
  Xaa₇ is Thr or Ser;
  Xaa₈ is Ala, Ser or Thr;
  Xaa₉ is Ala, Norval, Val, Norleu, Asp or Glu;
  Xaa₁₀ is Ala, Leu, Ile, Val, pentylglycine or Met;
  Xaa₁₁ is Ala or Ser;
  Xaa₁₂ is Ala or Lys;
  Xaa₁₃ is Ala or Gln;
  Xaa₁₄ is Ala, Leu, Ile, pentylglycine, Val or Met;
  Xaa₁₅ is Ala or Glu;
  Xaa₁₆ is Ala or Glu;
  Xaa₁₇ is Ala or Glu;
  Xaa₁₉ is Ala or Val;
  Xaa₂₀ is Ala or Arg;
  Xaa₂₁ is Ala, Leu or Lys-NH$^\epsilon$-R where R is Lys, Arg, $C_{1-10}$ straight chain or branched alkanoyl or cycloalkyl-alkanoyl;
  Xaa₂₂ is Phe, Tyr or naphthylalanine;
  Xaa₂₃ is Ile, Val, Leu, pentylglycine, tert-butylglycine or Met;
  Xaa₂₄ is Ala, Glu or Asp;
  Xaa₂₅ is Ala, Trp, Phe, Tyr or naphthylalanine;
  Xaa₂₆ is Ala or Leu;
  Xaa₂₇ is Lys, Asn, Lys-NH$^\epsilon$—R or Ala where R is Lys, Arg, $C_1$-$C_{10}$ straight chain or branched alkanoyl or cycloalkylalkanoyl;
  Xaa₂₈ is Lys, Asn, Lys-NH$^\epsilon$-R or Ala where R is Lys, Arg, $C_1$-$C_{10}$ straight chain or branched alkanoyl or cycloalkylalkanoyl;
  Z₁ is —OH,

—NH₂,

Gly-Z₂,

Gly Gly-Z₂,

Gly Gly Xaa₃₁-Z₂,

Gly Gly Xaa₃₁ Ser-Z₂,

Gly Gly Xaa₃₁ Ser Ser-Z₂,

Gly Gly Xaa₃₁ Ser Ser Gly-Z₂,

Gly Gly Xaa₃₁ Ser Ser Gly Ala-Z₂,

Gly Gly Xaa₃₁ Ser Ser Gly Ala Xaa₃₆-Z₂,

Gly Gly Xaa₃₁ Ser Ser Gly Ala Xaa₃₆ Xaa₃₇-Z₂,

Gly Gly Xaa₃₁ Ser Ser Gly Ala Xaa₃₆ Xaa₃₇ Xaa₃₈-Z₂ or

Gly Gly Xaa₃₁ Ser Ser Gly Ala Xaa₃₆ Xaa₃₇ Xaa₃₈ Xaa₃₉-Z₂;

Xaa₃₁, Xaa₃₆, Xaa₃₇ and Xaa₃₈ are independently selected from the group consisting of Pro, homoproline, 3Hyp, 4Hyp, thioproline, N-alkylglycine, N-alkylpentylglycine and N-alkylalanine;
  Xaa₃₉ is Ser or Tyr; and
  Z₂ is —OH or —NH₂;
  provided that no more than three of Xaa₃, Xaa₄, Xaa₅, Xaa₆, Xaa₈, Xaa₉, Xaa₁₀, Xaa₁₁, Xaa₁₂, Xaa₁₃, Xaa₁₄, Xaa₁₅, Xaa₁₆, Xaa₁₇, Xaa₁₉, Xaa₂₀, Xaa₂₁, Xaa₂₄, Xaa₂₅, Xaa₂₆, are Ala; and provided also that, if Xaa₁ is His, Arg, Tyr, or 4-imidazopropionyl then at least one of Xaa₃, Xaa₄ and Xaa₉ is Ala.

Exemplary compounds of formula (VI) include those wherein Xaa₁ is His, Ala, Norval or 4-imidazopropionyl. Preferably, Xaa₁ is His, or 4-imidazopropionyl or Ala, more preferably His or 4-imidazopropionyl.

Exemplary compounds of formula (VI) include those wherein Xaa₂ is Gly.

Exemplary compounds of formula (VI) include those wherein Xaa₄ is Ala.

Exemplary compounds of formula (VI) include those wherein Xaa₉ is Ala.

Exemplary compounds of formula (VI) include those wherein Xaa₁₄ is Leu, pentylglycine or Met.

Exemplary compounds of formula (VI) include those wherein Xaa₂₅ is Trp or Phe.

Exemplary compounds of formula (VI) include those wherein Xaa₆ is Ala, Phe or naphthylalanine; Xaa₂₂ is Phe or naphthylalanine; and Xaa₂₃ is Ile or Val.

Exemplary compounds of formula (VI) include those wherein Z₁ is —NH₂.

Exemplary compounds of formula (VI) include those wherein Xaa₃₁, Xaa₃₆, Xaa₃₇ and Xaa₃₈ are independently selected from the group consisting of Pro, homoproline, thioproline and N-alkylalanine.

Exemplary compounds of formula (VI) include those wherein Xaa₃₉ is Ser.

Exemplary compounds of formula (VI) include those wherein Z₂ is NH₂.

Exemplary compounds of formula (VI) include those 42 wherein Z₁ is —NH₂.

Exemplary compounds of formula (VI) include those wherein Xaa₂₁ is Lys-NH$^\epsilon$—R where R is Lys, Arg, $C_1$-$C_{10}$ straight chain or branched alkanoyl.

Exemplary compounds of formula (VI) include those wherein $X_{27}$ is Lys or Lys-NH$^\epsilon$—R, where R is Lys, Arg, $C_1$-$C_{10}$ straight chain or branched alkanoyl and $X_{28}$ is Asn or Ala.

Other compounds of formula (VI) include those described in PCT Application Serial No. PCT/US98/24273, filed Nov. 13, 1998, entitled "Novel Exendin Agonist Compounds" as having an amino acid sequence selected from those identified therein as SEQ ID NOS: 95-110, and herein identified as SEQ ID NOS: 92-107.

Formula VII

Compounds particularly useful according to the present invention are exendin analogs with agonist activity described in U.S. patent application Ser. No. 09/003,869, filed Jan. 7, 1998, entitled "Use of Exendins And Agonists Thereof For The Reduction of Food Intake", U.S. patent application Ser. No. 09/554,531, including compounds of the formula (VII) [SEQ ID NO:21]:

Xaa₁ Xaa₂ Xaa₃ Gly Thr Xaa₆ Xaa₇ Xaa₈ Xaa₉

Xaa₁₀ Ser Lys Gln Xaa₁₄ Glu Glu Glu Ala Val

-continued

```
Arg Leu Xaa22 Xaa23 Xaa24 Xaa25 Leu Lys Asn

Gly Gly Xaa31 Ser Ser Gly Ala Xaa36 Xaa37

Xaa38 Xaa39-Z
``` wherein:
  $Xaa_1$ is His, Arg or Tyr;
  $Xaa_2$ is Ser, Gly, Ala or Thr;
  $Xaa_3$ is Asp or Glu;
  $Xaa_6$ is Phe, Tyr or naphthylalanine;
  $Xaa_7$ is Thr or Ser;
  $Xaa_8$ is Ser or Thr;
  $Xaa_9$ is Asp or Glu;
  $Xaa_{10}$ is Leu, Ile, Val, pentylglycine or Met;
  $Xaa_{14}$ is Leu, Ile, pentylglycine, Val or Met;
  $Xaa_{22}$ is Phe, Tyr or naphthylalanine;
  $Xaa_{23}$ is Ile, Val, Leu, pentylglycine, tert-butylglycine or Met;
  $Xaa_{24}$ is Glu or Asp;
  $Xaa_{25}$ is Trp, Phe, Tyr, or naphthylalanine;
  $Xaa_{31}$, $Xaa_{36}$, $Xaa_{37}$ and $Xaa_{38}$ are independently Pro, homoproline, 3Hyp, 4Hyp, thioproline, N-alkylglycine, N-alkylpentylglycine or N-alkylalanine;
  $Xaa_{39}$ is Ser, Thr or Tyr; and Z is —OH or —NH$_2$;
with the proviso that the compound does not have the formula of either SEQ ID NOS:1 or 2. Preferred N-alkyl groups for N-alkylglycine, N-alkylpentylglycine and N-alkylalanine include lower alkyl groups preferably of 1 to about 6 carbon atoms, more preferably of 1 to 4 carbon atoms. Also useful in the present invention are pharmaceutically acceptable salts of the compounds of formula (VII).

Exemplary exendin analogs include those wherein $Xaa_1$ is His or Tyr. More preferably $Xaa_1$ is His.

Provided are those compounds wherein $Xaa_2$ is Gly.

Provided are those compounds wherein $Xaa_{14}$ is Leu, pentylglycine or Met.

Exemplary compounds include those wherein $Xaa_{25}$ is Trp or Phe.

Also provided are compounds where $Xaa_6$ is Phe or naphthylalanine; $Xaa_{23}$ is Ile or Val and $Xaa_{31}$, $Xaa_{36}$, $Xaa_{37}$ and $Xaa_{38}$ are independently selected from Pro, homoproline, thioproline or N-alkylalanine. Preferably N-alkylalanine has a N-alkyl group of 1 to about 6 carbon atoms.

According to one embodiment, $Xaa_{36}$, $Xaa_{37}$ and $Xaa_{38}$ are the same amino acid reside.

Provided are compounds wherein $Xaa_{39}$ is Ser or Tyr, more preferably Ser.

Preferably Z is —NH$_2$.

According to one embodiment, provided are compounds of formula (VII) wherein $Xaa_1$ is His or Tyr, preferably His; $Xaa_2$ is Gly; $Xaa_6$ is Phe or naphthylalanine; $Xaa_{14}$ is Leu, pentylglycine or Met; $Xaa_{22}$ is Phe or naphthylalanine; $Xaa_{23}$ is Ile or Val; $Xaa_{31}$, $Xaa_{36}$, $Xaa_{37}$ and $Xaa_{38}$ are independently selected from Pro, homoproline, thioproline or N-alkylalanine; and $Xaa_{39}$ is Ser or Tyr, more preferably Ser. More preferably Z is —NH$_2$.

According to another embodiment, exemplary compounds include those of formula (VII) wherein: $Xaa_1$ is His or Arg; $Xaa_2$ is Gly; $Xaa_3$ is Asp or Glu; $Xaa_6$ is Phe or napthylalanine; $Xaa_7$ is Thr or Ser; $Xaa_8$ is Ser or Thr; $Xaa_9$ is Asp or Glu; $Xaa_{10}$ is Leu or pentylglycine; $Xaa_{14}$ is Leu or pentylglycine; $Xaa_{22}$ is Phe or naphthylalanine; $Xaa_{23}$ is Ile, Val or t-butyltylglycine; $Xaa_{24}$ is Glu or Asp; $Xaa_{25}$ is Trp or Phe; $Xaa_{31}$, $Xaa_{36}$, $Xaa_{37}$, and $Xaa_{38}$ are independently Pro, homoproline, thioproline, or N-methylalanine; $Xaa_{39}$ is Ser or Tyr: and Z is —OH or —NH$_2$; with the proviso that the compound does not have the formula of either SEQ ID NOS:1 or 2. More preferably Z is —NH$_2$.

According to another embodiment, provided are compounds where $Xaa_{14}$ is Leu, Ile, Val or pentylglycine, more preferably Leu or pentylglycine, and $Xaa_{25}$ is Phe, Tyr or naphthylalanine, more preferably Phe or naphthylalanine. These compounds are believed to exhibit advantageous duration of action and to be less subject to oxidative degradation, both in vitro and in vivo, as well as during synthesis of the compound.

Formula VIII

Also provided are compounds described in PCT Application Serial No. PCT/US98/16387, filed Aug. 6, 1998, entitled "Novel Exendin Agonist Compounds", U.S. patent application Ser. No. 10/181,102, including compounds of the formula (VIII) [SEQ ID NO:22]:

```
Xaa1 Xaa2 Xaa3 Gly Thr Xaa6 Xaa7 Xaa8 Xaa9

Xaa10 Ser Lys Gln Xaa14 Glu Glu Glu Ala Val

Arg Leu Xaa22 Xaa23 Xaa24 Xaa25 Leu Xaa27 Xaa28

Gly Gly Xaa31 Ser Ser Gly Ala Xaa36 Xaa37

Xaa38 Xaa39-Z
``` wherein:
  $Xaa_1$ is His, Arg, Tyr or 4-imidazopropionyl;
  $Xaa_2$ is Ser, Gly, Ala or Thr;
  $Xaa_3$ is Asp or Glu;
  $Xaa_6$ is Phe, Tyr or naphthylalanine;
  $Xaa_7$ is Thr or Ser;
  $Xaa_8$ is Ser or Thr;
  $Xaa_9$ is Asp or Glu;
  $Xaa_{10}$ is Leu, Ile, Val, pentylglycine or Met;
  $Xaa_{14}$ is Leu, Ile, pentylglycine, Val or Met;
  $Xaa_{22}$ is Phe, Tyr or naphthylalanine;
  $Xaa_{23}$ is Ile, Val, Leu, pentylglycine, tert-butylglycine or Met;
  $Xaa_{24}$ is Glu or Asp;
  $Xaa_{25}$ is Trp, Phe, Tyr, or naphthylalanine;
  $Xaa_{27}$ is Lys, Asn, or Lys-NH$^\epsilon$—R where R is Lys, Arg, $C_1$-$C_{10}$ straight chain or branched alkanoyl or cycloalkylalkanoyl;
  $Xaa_{28}$ is Lys, Asn, or Lys-NH$^\epsilon$—R where R is Lys, Arg, $C_1$-$C_{10}$ straight chain or branched alkanoyl or cycloalkylalkanoyl;
  $Xaa_{31}$, $Xaa_{36}$, $Xaa_{37}$ and $Xaa_{38}$ are independently Pro, homoproline, 3Hyp, 4Hyp, thioproline, N-alkylglycine, N-alkylpentylglycine or N-alkylalanine;
  $Xaa_{39}$ is Ser, Thr or Tyr; and
  Z is —OH or —NH$_2$;
with the proviso that the compound does not have the formula of either SEQ ID NOS: 1 or 2. Suitable compounds of formula (VIII) include compounds described in PCT Application Serial No. PCT/US98/16387, filed Aug. 6, 1998, entitled "Novel Exendin Agonist Compounds," U.S. patent application Ser. No. 10/181,102, having the amino acid sequences of SEQ ID NOS: 5-39 therein, herein identified as SEQ ID NOS: 108-142.

Exemplary exendin analogs of formula (VIII) include those wherein $Xaa_1$ is His, Tyr or 4-imidazopropionyl. More preferably, $Xaa_1$ is His or 4-imidazopropionyl.

Provided are those compounds of formula (VIII) wherein $Xaa_2$ is Gly.

Provided are those compounds of formula (VIII) wherein $Xaa_{14}$ is Leu, pentylglycine or Met.

Provided are those compounds of formula (VIII) wherein $Xaa_{25}$ is Trp or Phe.

Provided are those compounds of formula (VIII) wherein $Xaa_{27}$ is Lys or Lys-NH$^\varepsilon$—R where R is Lys, Arg, $C_1$-$C_{10}$ straight chain or branched alkanoyl and $Xaa_{28}$ is Asn.

Also provided are compounds of formula (VIII) wherein $Xaa_6$ is Phe or naphthylalanine; $Xaa_{22}$ is Phe or naphthylalanine; $Xaa_{23}$ is Ile or Val and $Xaa_{31}$, $Xaa_{36}$, $Xaa_{37}$ and $Xaa_{38}$ are independently selected from Pro, homoproline, thioproline or N-alkylalanine. According to one embodiment, $Xaa_{39}$ is Ser or Tyr. Provide are compounds wherein $Xaa_{39}$ is Ser. Preferably, Z is —NH$_2$.

According to one embodiment, provided are compounds of formula (VIII) wherein $Xaa_6$ is Phe or naphthylalanine; $Xaa_{22}$ is Phe or naphthylalanine; $Xaa_{23}$ is Ile or Val; $Xaa_{27}$ is Lys or Lys-NH$^\varepsilon$—R where R is Lys, Arg, $C_1$-$C_{10}$ straight chain or branched alkanoyl, and $Xaa_{28}$ is Asn; and $Xaa_{31}$, $Xaa_{36}$, $Xaa_{37}$ and $Xaa_{38}$ are independently selected from Pro, homoproline, thioproline or N-alkylalanine.

In another embodiment, exendins and exendin analogs of the invention do not include the peptides of SEQ ID NOS:3-14. In one embodiment, exendin analogs include the analogs of Formulas (I-VIII), with the proviso that the analogs do not include the peptides of SEQ ID NOs:1-2.

Also useful within the scope of the present invention are narrower genera of compounds of the disclosed formulae, for example formulae I through VIII, having peptides of various lengths, for example genera of compounds that do not include peptides having a length of greater than 27, 28, 29, 30, 31, 32, 33, 34, 35, 36, 37 or 38 amino acid residues.

Exendins, exendin analog agonists and exendin agonists that are peptides, described herein may be prepared through peptide purification as described in, for example, Eng, et al., *J. Biol. Chem.* 265:20259-62, 1990; and Eng, et al., *J. Biol. Chem.* 267:7402-05, 1992, which are incorporated by reference herein. Alternatively, exendins, exendin peptide agonists and exendin analog agonists may be prepared by methods known to those skilled in the art, for example, as described in Raufman, et al., *J. Biol. Chem.* 267:21432-37, 1992), which is incorporated by reference herein, using standard solid-phase peptide synthesis techniques, for example, using an automated or semiautomated peptide synthesizer. Typically, using such techniques, an α-N-carbamoyl protected amino acid and an amino acid attached to the growing peptide chain on a resin are coupled at room temperature in an inert solvent such as dimethylformamide, N-methylpyrrolidinone or methylene chloride in the presence of coupling agents such as dicyclohexylcarbodiimide and 1-hydroxybenzotriazole in the presence of a base such as diisopropylethylamine. The α-N-carbamoyl protecting group is removed from the resulting peptide-resin using a reagent such as trifluoroacetic acid or piperidine, and the coupling reaction repeated with the next desired N-protected amino acid to be added to the peptide chain. Suitable N-protecting groups are well known in the art, with, for example, t-butyloxycarbonyl (tBoc) and fluorenylmethoxycarbonyl (Fmoc).

The solvents, amino acid derivatives and 4-methylbenzhydryl-amine resin used in the peptide synthesizer may be purchased from Applied Biosystems Inc. (Foster City, Calif.). The following side-chain protected amino acids may be purchased from Applied Biosystems, Inc.: BSD-112344.1-Arg (Pmc), Boc-Thr(Bzl), Fmoc-Thr(t-Bu), Boc-Ser(Bzl), Fmoc-Ser(t-Bu), Boc-Tyr(BrZ), Fmoc-Tyr(t-Bu), Boc-Lys(Cl—Z), Fmoc-Lys(Boc), Boc-Glu(Bzl), Fmoc-Glu(t-Bu), Fmoc-His (Trt), Fmoc-Asn(Trt), and Fmoc-Gln(Trt). Boc-His(BOM) may be purchased from Applied Biosystems, Inc. or Bachem Inc. (Torrance, Calif.). Anisole, dimethylsulfide, phenol, ethanedithiol, and thioanisole may be obtained from Aldrich Chemical Company (Milwaukee, Wis.). Air Products and Chemicals (Allentown, Pa.) supplies HF. Ethyl ether, acetic acid and methanol may be purchased from Fisher Scientific (Pittsburgh, Pa.).

Solid phase peptide synthesis may be carried out with an automatic peptide synthesizer (Model 430A, Applied Biosystems Inc., Foster City, Calif.) using the NMP/HOBt (Option 1) system and tBoc or Fmoc chemistry (see, Applied Biosystems User's Manual for the ABI 430A Peptide Synthesizer, Version 1.3B Jul. 1, 1988, section 6, pp. 49-70, Applied Biosystems, Inc., Foster City, Calif.) with capping. Boc-peptide-resins may be cleaved with HF (−50° C. to 0° C., 1 hour). The peptide may be extracted from the resin with alternating water and acetic acid, and the filtrates lyophilized. The Fmoc-peptide resins may be cleaved according to standard methods (Introduction to Cleavage Techniques, Applied Biosystems, Inc., 1990, pp. 6-12). Peptides may also be assembled using an Advanced Chem Tech Synthesizer (Model MPS 350, Louisville, Ky.).

Peptides may be purified by RP-HPLC (preparative and analytical) using a Waters Delta Prep 3000 system. A C4, C8 or C18 preparative column (10μ, 2.2×25 cm; Vydac, Hesperia, Calif.) may be used to isolate peptides, and purity may be determined using a C4, C8 or C18 analytical column (5 0.46× 25 cm; Vydac). Solvents (A=0.1% TFA/water and B=0.1% TFA/CH$_3$CN) may be delivered to the analytical column at a flowrate of 1.0 ml/min and to the preparative column at 15 ml/min. Amino acid analyses may be performed on the Waters Pico Tag system and processed using the Maxima program. Peptides may be hydrolyzed by vapor-phase acid hydrolysis (115° C., 20-24 h). Hydrolysates may be derivatized and analyzed by standard methods (Cohen, et al., The Pico Tag Method: A Manual of Advanced Techniques for Amino Acid Analysis, pp. 11-52, Millipore Corporation, Milford, Mass. (1989)). Fast atom bombardment analysis may be carried out by M-Scan, Incorporated (West Chester, Pa.). Mass calibration may be performed using cesium iodide or cesium iodide/glycerol. Plasma desorption ionization analysis using time of flight detection may be carried out on an Applied Biosystems Bio-Ion 20 mass spectrometer. Electrospray mass spectroscopy may be carried and on a VG-Trio machine.

Exendins, exendin analog agonists and exendin agonists that are peptides may also be prepared using recombinant DNA techniques, using methods now known in the art. See, e.g., Sambrook et al., Molecular CLONING: A LABORATORY MANUAL, 2d Ed., Cold Spring Harbor (1989). Alternatively, such compounds may be prepared by homogeneous phase peptide synthesis methods. Non-peptide compounds useful in the present invention may be prepared by art-known methods. For example, phosphate-containing amino acids and peptides containing such amino acids, may be prepared using methods known in the art. See, e.g., Bartlett and Landen, *Biorg. Chem.* 14:356-377 (1986).

Exendins, exendin agonists or exendin analog agonists may be formulated into pharmaceutical compositions for administration to subjects, including humans. These pharmaceutical compositions preferably include an amount of an exendin, an exendin agonist or exendin analog agonist effective to reduce body weight in the subject, reduce BMI, alter body composition, treat diabetes, lower fasting blood glucose, or reduce postprandial blood glucose and a pharmaceutically acceptable carrier.

Pharmaceutically acceptable carriers useful in these pharmaceutical compositions include, e.g., ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions disclosed herein may be administered parenterally, orally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. In one embodiment, the compositions are administered by an infusion pump or subcutaneous injection of a slow release, extended release, sustained release or long acting formulation. In one embodiment, subcutaneous injections are administered once a day; once every two, three, four, five, or six days; once per week; twice per month; once a month; every other month or every third month.

Any of the exendins, exendin agonists or exendin analog agonists may be administered in the acid or amide form. Additionally, any of the exendins, exendin agonists or exendin analog agonists may form salts with various inorganic and organic acids and bases. Such salts include, without limitation, salts prepared with organic and inorganic acids, for example, HCl, HBr, $H_2SO_4$, $H_3PO_4$, trifluoroacetic acid, acetic acid, formic acid, methanesulfonic acid, toluenesulfonic acid, maleic acid, fumaric acid and camphorsulfonic acid. Salts prepared with bases include, without limititation, ammonium salts, alkali metal salts, e.g., sodium and potassium salts, and alkali earth salts, e.g., calcium and magnesium salts. Acetate, hydrochloride, and trifluoroacetate salts are particular examples. The salts may be formed by conventional means, as by reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

In a one embodiment, the route of administration results in an average plasma exendin, exendin agonist or exendin analog agonist concentration of greater than or equal to about 50 pg/ml for a period of at least about 12 hours, or least about 1, least about 2, least about 3, least about 4, least about 5, least about 6, or least about 7 days; at least about 1, least about 2, least about 3, least about 4, least about 5, least about 6, least about 7, least about 8, least about 9, least about 10, least about 11, least about 12, least about 13, least about 14, least about 15, or least about 16 weeks; or at least about 5, least about 6, least about 7, least about 8, least about 9, least about 10, least about 11, or least about 12 months. In another embodiment, the route of administration results in a minimum plasma exendin, exendin agonist or exendin analog agonist concentration of greater than or equal to about 50 pg/ml for a period of at least about 12 hours, or least about 1, least about 2, least about 3, least about 4, least about 5, least about 6, or least about 7 days; at least about 1, least about 2, least about 3, least about 4, least about 5, least about 6, least about 7, least about 8, least about 9, least about 10, least about 11, least about 12, least about 13, least about 14, least about 15, or least about 16 weeks; or at least about 5, least about 6, least about 7, least about 8, least about 9, least about 10, least about 11, or least about 12 months. Any route of administration can be used in the present methods so long as the administration results in an average plasma exendin, exendin agonist or exendin analog agonist concentration of at least about 65 pg/ml, about 75 pg/ml, about 85 pg/ml, about 100 pg/ml, about 150 pg/ml, about 170 pg/ml, about 175 pg/ml, about 200 pg/ml, about 225 pg/ml, about 250 pg/ml, about 300 pg/ml, about 350 pg/ml, about 400 pg/ml, about 450 pg/ml, about 500 pg/ml, about 550 pg/ml, or about 600 pg/ml. In other embodiments, the average concentration of the exendin, exendin agonist or exendin analog agonist is between at least about 170 pg/ml and 600 pg/ml or between at least about 170 pg/ml and 350 pg/ml. In still other embodiments, the average plasma concentration of the exendin, exendin agonist or exendin analog agonist is greater than 40 pmoles/liter, greater than 50 pmoles/liter, greater than 60 pmoles/liter, greater than 70 pmoles/liter, greater than 80 pmoles/liter, greater than 90 pmoles/liter, greater than 100 pmoles/liter, greater than 110 pmoles/liter, greater than 120 pmoles/liter, greater than 130 pmoles/liter, greater than 140 pmoles/liter, or greater than 150 pmoles/liter. In still further embodiments, the average plasma concentration of the exendin, exendin agonist or exendin analog agonist is greater than 40 pmoles/liter but less than 150 pmoles/liter or greater than 40 pmoles/liter but less than 80 pmoles/liter. In one embodiment, the exendin, exendin agonist or exendin analog agonist is exendin-4. In other embodiments, the concentration of the exendin, exendin agonist or exendin analog agonist is the concentration of the exendin, exendin agonist or exendin analog agonist that results in a biological or therapeutic effect, e.g. weight reduction, glucose lowering, alteration in body composition, etc., equivalent to that observed with a given concentration of exendin-4. These average concentrations are maintained for a period of at least about 12 hours, or least about 1, least about 2, least about 3, least about 4, least about 5, least about 6, or least about 7 days; at least about 1, least about 2, least about 3, least about 4, least about 5, least about 6, least about 7, least about 8, least about 9, least about 10, least about 11, least about 12, least about 13, least about 14, least about 15, or least about 16 weeks; or at least about 5, least about 6, least about 7, least about 8, least about 9, least about 10, least about 11, or least about 12 months. In still another embodiment, the route of administration results in a sustained minimum plasma exendin, exendin agonist or exendin analog agonist concentration of greater than or equal to about 65 pg/ml, greater than or equal to about 75 pg/ml, greater than or equal to about 85 pg/ml, about 100 pg/ml, greater than or equal to about 150 pg/ml, greater than or equal to about 170 pg/ml, greater than or equal to about 175 pg/ml, greater than or equal to about 200 pg/ml, greater than or equal to about 225 pg/ml, greater than or equal to about 250 pg/ml, greater than or equal to about 300 pg/ml, greater than or equal to about 350 pg/ml, greater than or equal to about 400 pg/ml, greater than or equal to about 450 pg/ml, greater than or equal to about 500 pg/ml, greater than or equal to about 550 pg/ml, or greater than or equal to about 600 pg/ml. In other embodiments, the minimum concentration of the exendin, exendin agonist or exendin analog agonist is between at least about 170 pg/ml and 600 pg/ml or between at least about 170 pg/ml and 350 pg/ml. In still other embodiments, minimum plasma concentration of the exendin, exendin agonist or exendin analog agonist is greater than 40 pmoles/liter, greater than 50 pmoles/liter, greater than 60 pmoles/liter, greater than 70 pmoles/liter, greater than 80 pmoles/liter, greater than 90 pmoles/liter, greater than 100 pmoles/liter, greater than 110 pmoles/liter, greater than 120 pmoles/liter, greater than 130 pmoles/liter, greater than 140 pmoles/liter, or greater than 150 pmoles/liter. In still further embodiments, the minimum plasma concentration of the exendin, exendin agonist or exendin analog agonist is greater than 40 pmoles/liter but less than 150 pmoles/liter or greater than 40 pmoles/liter but less than 80 pmoles/liter. In one embodiment, the exendin, exendin agonist or exendin analog agonist is exendin-4. In other embodiments, the concentration of the exendin, exendin agonist or exendin analog agonist is the concentration of the exendin, exendin agonist or exendin analog agonist that results in a biological or therapeutic effect, e.g. weight reduction, glucose lowering, alteration in body composition, etc., equivalent to that observed with a given concentration of exendin-4. These minimum concentrations are sustained for a period of at least about 12 hours, or at least about 1, at least about 2, at least about 3, at least about 4, at least about 5, at least about 6, or at least about 7 days; at least about 1, at least about 2, at least about 3, at least about 4, at least about 5, at least about 6, at least about 7, at least about 8, at least about 9, at least about 10, at least about 11, at least about 12, at least about 13, at least about 14, at least about 15, or at least about 16 weeks; or at least about 5, at least about 6, at least about 7, at least about 8, at least about 9, at least about 10, at least about 11, or at least about 12 months. Plasma exendin, exendin agonist or exendin agonist analog concentrations can be measured using any method available.

Average concentrations can be determined over the entire time period of interest, or alternatively, within a subunit of the time period of interest. For example, and without limitation, the average daily concentration of an exendin, exendin agonist or exendin analog agonist over a period of one week, one month, three months, six months or a year; the average weekly concentration over a period of one month, three months, six months, nine months or a year; or the average monthly concentration over six months, nine months or one year; etc. It should be recognized that the average (mean) concentrations will encompass individual measurements that are above or below the mean. Thus, at any given measurement of concentration may be below the desired minimum average so long as the average value over the desired time period is at or above the required minimum value. As used herein in reference to concentration, the term "average or minimum" refers to the alternative and should be read as the either the average concentration or the minimum concentration.

Sterile injectable forms of the compositions of this invention may be aqueous or oleaginous suspension. These suspensions may be formulated according to techniques known in the art, using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms, including emulsions and suspensions. Other commonly used surfactants, such as TWEENs, Spans and other emulsifying agents or bioavailability enhancers which are commonly used in the manufacture of pharmaceutically acceptable solid, liquid, or other dosage forms may also be used for the purposes of formulation.

Parenteral formulations may be a single bolus dose, an infusion, or a loading bolus dose followed with a maintenance dose. These compositions may be administered according to any dosage schedule described herein.

The pharmaceutical compositions of this invention may be orally administered in any orally acceptable dosage form including, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically. Topical application can be effected in a rectal suppository formulation (see above) or in a suitable enema formulation. Topical transdermal patches may also be used.

For topical applications, the pharmaceutical compositions may be formulated in a suitable ointment containing the active component suspended or dissolved in one or more carriers. Carriers for topical administration of the compounds of this invention include, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol, and water.

For ophthalmic use, the pharmaceutical compositions may be formulated as micronized suspensions in isotonic, pH-adjusted sterile saline, or, preferably, as solutions in isotonic, pH-adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of exendin, exendin agonist or exendin analog agonist that may be combined with the carrier materials to produce a single dosage form will vary depending upon the host treated and the particular mode of administration. The compositions can be formulated so that a dosage of between 0.1-1000 pmoles/kg body weight/minute (when administered by infusion) of exendin, exendin agonists or exendin analog agonist is administered to a patient receiving these compositions. In some embodiments of the invention, the dosage is 1-10 pmoles/kg body weight/minute (when administered by infusion). In one embodiment the dosage is 0.5-2.0 pmoles/kg/min when administered by intravenous infusion. The composition may be administered as a single dose, multiple doses, or over an established period of time. In one embodiment, the dosage is about 0.8 mg of a long acting formulation containing about 5% of an exendin, exendin agonist, or exendin analog agonist, for example, exendin-4. In another embodiment, the dosage is about 2.0 mg of a long acting formulation containing about 5% of an exendin, exendin agonist, or exendin analog agonist for example, exendin-4. In additional embodiments, the dosage is about 1.0, about 1.25, about 1.5, about 1.75, about 2.25, about 2.5, about 2.75, about 3.0, about 3.25, about 3.5, about 3.75, about 4.0, about 4.25, about 4.5, about 4.75, or about 5.0 mg of a long acting formulation containing about 5% of an exendin, exendin agonist, or exendin analog agonist for example, exendin-4. It will be recognized that the exact dosage will vary with the percent exendin and the amount of carriers and/or excipients in a particular formulation. It is well within the skill of those of ordinary skill in the art to make such adjustments in order to obtain the desired plasma concentrations of an exendin, exendin agonist or exendin analog agonist described herein. It should be noted that any combination of doses and means of administration may be utilized as long as the dose in combination with the means of administration as long as the desired therapeutically effective level of the exendin, exendin agonist, or exendin agonist analog is achieved.

In one embodiment exendin or exendin agonists or analogs thereof are administered to patients identified as overweight, obese, diabetic or a combination thereof. In another embodiment, the exendin or exendin agonists or analogs thereof is administered by injection at least once a day, once a week, or by continuous infusion via pump. In yet another embodiment, the exendin or exendin agonists or exendin analog agonists are formulated for administration from a subcutaneous depot over a period of days, weeks or months.

In another embodiment, the exendins exendin agonists or exendin analog agonists are formulated in a sustained release or long acting formulation. In one embodiment, the sustained release formulation comprises a biocompatible polymer, an exendin, or exendin analog agonist, and a sugar. Exemplary formulations are disclosed in U.S. patent application Ser. No. 09/942,631, filed Aug. 31, 2001 (now U.S. Pat. No. 6,824,822) and related application Ser. No. 11/312,371, filed Dec. 21, 2005; U.S. Provisional Application No. 60/419,388, filed Oct. 17, 2002 and related U.S. patent application Ser. Nos. 10/688,786 and 10/688,059 filed Oct. 17, 2003; U.S. Provisional Application No. 60/757,258, filed Jan. 9, 2006; U.S. Provisional Application Ser. No. 60/563,245, filed Apr. 15, 2004 and related U.S. patent application Ser. No. 11/104,877, filed Apr. 13, 2005; and U.S. application Ser. No. 11/107,550, filed Apr. 15, 2005, the entireties of which are incorporated herein by reference. Such formulations can be administered, for example by subcutaneous injection, once per day, every 2 days, 3 days, 4 days, 5 days, or 6 days; once per week, once every 2 weeks, or once every three weeks; or once per month, once every other month or once every 3 months.

Sustained release compositions can be prepared by a phase separation process. The general process for producing a sustained release or long acting formulation comprising microparticles containing an exendin, exendin agonist or exendin analog agonist and sucrose for a 1 kg batch size is described below.

A water-in-oil emulsion is created with the aid of a homogenizer. Suitable homogenizers include an in-line Megatron homogenizer MT-V 3-65 F/FF/FF, Kinematica AG, Switzerland. The water phase of the emulsion can be prepared by dissolving an exendin, exendin agonist or exendin analog agonist, for example, exendin-4, and excipients such as sucrose in water. The concentration of exendin in the resulting solution can be from about 50 mg/g to about 100 mg/g. For example, when the drug is exendin-4, the concentration of drug in solution can be from about 30 g to about 60 g per 600 g of water. In a particular embodiment, 50 g exendin-4 and 20 g sucrose are dissolved in 600 g water for irrigation (WFI). The specified amounts listed above represent a nominal load without adjustment to compensate for peptide content strength specific to the lot of exendin-4 used. The oil phase of the emulsion is prepared by dissolving PLGA polymer (e.g., 930 g of purified 50:50 DL4A PLGA (Alkermes, Inc.) in methylene chloride (14.6 kg or 6% w/w)).

The water phase is then added to the oil phase to form a coarse emulsion with an overhead mixer for about three minutes. Then, the coarse emulsion is homogenized at approximately 21300 rpm at ambient temperature for three discrete periods. This should result in an inner emulsion droplet size of less than 1 micron. It is understood that inner emulsion formation can be achieved using any suitable means. Suitable means of emulsion formation include, but are not limited to, homogenization as described above and sonication.

A coacervation step is then performed by adding silicone oil (21.8 kg of Dimethicone, NF, 350 cs) over a time period of less than or equal to about 5 minutes to the inner emulsion. This is equivalent to a ratio of 1.5:1, silicone oil to methylene chloride. The methylene chloride from the polymer solution partitions into the silicone oil and begins to precipitate the polymer around the water phase containing the exendin, leading to microencapsulation. The embryonic microspheres thus formed are soft and require hardening. Frequently, the embryonic microspheres are permitted to stand for a short period of time, for example, less than 1 minute or from about 1 minute to about 5 minutes prior to proceeding to the microsphere hardening step.

The embryonic microspheres are immediately transferred into a heptane/ethanol solvent mixture. The volume of heptane/ethanol mixture needed can be determined based on the microsphere batch size, typically a 16:1 ratio of heptane/ethanol solvent to methylene chloride. For example, about 210 kg heptane and 23 kg ethanol in a 3° C. cooled, stirred tank can be used. This solvent mixture hardens the microspheres by extracting additional methylene chloride from the microspheres. This hardening step can also be referred to as quenching. After being quenched for 1 hour at 3° C., the solvent mixture is either decanted and fresh heptane (13 Kg) is added at 3° C. and held for 1 hour to rinse off residual silicone oil, ethanol and methylene chloride on the microsphere surface or pumped directly to the collection step.

At the end of the quench or decant/wash step, the microspheres are transferred and collected, for example, on a 12" Sweco Pharmasep Filter/Dryer Model PH12Y6. In this example, the filter/dryer uses a 25 micron multilayered collection screen and is connected to a motor that vibrates the screen during collection and drying. A final rinse with heptane (6 Kg at 3° C.) can be performed to ensure maximum line transfer and to remove any excess silicone oil. The microspheres can then be dried under vacuum with or without a constant purge of nitrogen gas at controlled rate, for example:

3 to 10 hours (e.g. 6 hours) at 3° C.; 3 to 10 hours ramping to 41° C. (e.g. 6 hours); and maintaining for a long period (e.g. 80-90 hours) at 41° C.

After the completion of drying, the microspheres are discharged into a collection vessel, sieved through a 150 μm sieve, and stored at about −20° C. until filling.

An alternative general process for producing a sustained release or long acting formulation comprising microparticles containing an exendin, exendin agonist or exendin analog agonist and sucrose is as follows:

A water-in-oil emulsion is created with the aid of a sonicator. Suitable sonicators include Vibracell VCX 750 with model CV33 probe head, Sonics and Materials Inc., Newtown, Conn. The water phase of the emulsion is prepared by dissolving an exendin, for example, exendin-4, and excipients such as sucrose in water. The concentration of drug in the resulting solution can be from about 50 mg/ml to about 100 mg/ml. For example, when the drug is exendin-4, the concentration of drug in solution can be from about 3.28 g to about 6.55 g per 65.5 g of water. In a particular embodiment, 5.46 g exendin-4 and 2.18 g sucrose are dissolved in 65.5 g water for irrigation or WFI. The specified amounts listed above represent a 4% overage to target load in order to compensate for losses upon filter sterilization of the components. The oil phase of the emulsion is prepared by dissolving PLGA polymer (e.g., 97.7 g of purified 50:50 DL4A PLGA (Alkermes, Inc.)) in methylene chloride (1539 g or 6% w/v).

The water phase is then added to the oil phase over about a three-minute period while sonicating at 100% amplitude at ambient temperature. The water phase containing the sucrose/exendin-4 is charged to the coacervation reactor. Reactor is then stirred at 1400 to 1600 rpm, with additional sonication at 100% amplitude for 2 minutes, followed by a 30 second hold, and then 1 minute more of sonication. This results in an inner emulsion droplet size of less than 0.5 microns. It is understood that inner emulsion formation can be achieved using any suitable means. Suitable means of emulsion formation include, but are not limited to, sonication as described above and homogenization.

A coacervation step is then performed by adding silicone oil (2294 gr of Dimethicone, NF, 350 cs) over time period of less than five minutes to the inner emulsion. This is equivalent to a ratio of 1.5:1, silicone oil to methylene chloride. The methylene chloride from the polymer solution partitions into the silicone oil and begins to precipitate the polymer around the water phase containing exendin, leading to microencapsulation. The embryonic microspheres thus formed are soft and require hardening. Frequently, the embryonic microspheres are permitted to stand for a short period of time, for example, of less than 1 minute or from about 1 minute to about 5 minutes prior to proceeding to the microsphere hardening step.

The embryonic microspheres are then immediately transferred into a heptane/ethanol solvent mixture. The volume of heptane/ethanol mixture needed can be determined based on the microsphere batch size. In the present example, about 22 kg heptane and 2448 g ethanol in a 3° C. cooled, stirred tank (350 to 450 rpm) are used. This solvent mixture hardens the microspheres by extracting additional methylene chloride from the microspheres. This hardening step can also be referred to as quenching. After being quenched for 1 hour at 3° C., the solvent mixture is decanted and fresh heptane (13 Kg) is added at 3° C. and held for 1 hour to rinse off residual silicone oil, ethanol and methylene chloride on the microsphere surface.

At the end of the rinse step, the microspheres are transferred and collected, for example, on a 6" diameter, 20 micron multilayered screen inside the cone shaped drying chamber which acts as a dead-end filter. A final rinse with heptane (6 Kg at 4° C.) is performed to ensure maximum line transfer. The microspheres are then dried with a constant purge of nitrogen gas at a controlled rate, for example, according to the following schedule: 18 hours at 3° C.; 24 hours at 25° C.; 6 hours at 35° C.; and 42 hours at 38° C.

After the completion of drying, the microspheres are discharged into a teflon/stainless steel sterilized collection vessel attached to the drying cone. The collection vessel is sealed, removed from the drying cone and stored at −20±5° C. until filling. Material remaining in the cone upon disassembly for cleaning is taken for drug content analysis.

Non-limiting examples of specific PLG polymers suitable for use in the general methods described above are listed below. The listed polymers can be obtained from Lakeshore Biomaterials of Birmingham, Ala., or Boehringer Ingelheim Pharma GmbH & Co. KG, Germany, although other sources may be available, and can be described as follows:

Polymer 2A: Poly(lactide-co-glycolide); 50:50 lactide:glycolide ratio; 12.3 kD Mol. Wt.; IV=0.15 (dL/g).

Polymer 4A: Poly(lactide-co-glycolide); 50:50 lactide:glycolide ratio; Mol. Wt. 45-64 kD; IV=0.45-0.47 (dL/g).

It is known in the art (See, for example, Peptide Acylation by Poly($\alpha$-Hydroxy Esters) by Lucke et al., Pharmaceutical Research, Vol. 19, No. 2, p. 175-181, February 2002) that proteins and peptides which are incorporated in PLG matrices can be undesirably altered (e.g., degraded or chemically modified) as a result of interaction with degradation products of the PLG or impurities remaining after preparation of the polymer. As such, the PLG polymers used in the preparation of microparticle formulations described herein can be purified prior to preparation of the sustained release compositions using art recognized purification methods.

A specific dosage and treatment regimen for any particular patient will depend upon a variety of factors, including the particular exendin or exendin agonists or analogs thereof the patient's age, body weight, general health, gender, and diet, and the time of administration, rate of excretion, drug combination, and the severity of the particular disease being treated. Judgment of such factors by medical caregivers is within ordinary skill in the art. The amount of exendin or exendin agonists or analogs thereof will also depend on the individual patient to be treated, the route of administration, the type of formulation, the characteristics of the compound used, the severity of the disease, and the desired effect. The amounts of exendin or exendin agonists or analogs thereof can be determined by pharmacological and pharmacokinetic principles well-known in the art.

In order that the invention described herein may be more fully understood, the following examples are set forth. It should be understood that these examples are for illustrative purposes only and are not to be construed as limiting this invention in any manner.

EXAMPLES

The pharmacokinetics of a long-acting release (LAR) formulation of exenatide was evaluated in a randomized, double-blind, placebo controlled, multicenter study in subjects with Type 2 diabetes. The study population consisted of 45 individuals with type 2 diabetes treated with a stable regimen of metformin or managed with diet modification and exercise for at least 3 months prior to screening. Subjects, male or female, were 18 to 75 years of age with a body mass index (BMI) of 25 kg/m$^2$ to 45 kg/m$^2$, inclusive, at screening, and HbA$_{1c}$ of 7.1% to 11.0%, inclusive, at screening. The study compared multiple doses of a long-acting release formulation of exenatide administered once weekly for 15 weeks by subcutaneous (SC) injection. The study was also conducted to examine the effects of such administration on the subjects' body weight and fasting and postprandial glucose concentrations. Subjects were randomly assigned to the respective treatment groups in a 1:1:2:2 proportion ($A_1$:$A_2$:B; C [Table 3]) prior to the lead-in period. During the 3-day, double-blind lead-in period, subjects self-administered exenatide 5 µg (groups B and C) or an equivalent volume of placebo (groups $A_1$ and $A_2$) SC, BID, within 15 minutes prior to meals in the morning and evening. This 3-day lead-in period was designed to expose subjects to exenatide prior to administration of exenatide LAR to determine if a subject may exhibit an acute sensitivity to exenatide.

TABLE 3

| Group | Lead-In Period 3-Day Double-Blind | | | Treatment Period 15-Week Double-Blind | | |
|---|---|---|---|---|---|---|
| | Lead-In Medication | Dose (µg)* | Dose Volume (ml) | Study Medication | Dose (mg)** | Dose Vol*** |
| $A_1$ | Placebo BID | — | 0.02 | Placebo LAR QW | — | X |
| $A_2$ | Placebo BID | — | 0.02 | Placebo LAR QW | — | Y |
| B | Exenatide BID | 5 | 0.02 | Exenatide LAR QW | 0.8 | X |
| C | Exenatide BID | 5 | 0.02 | Exenatide LAR QW | 2.0 | Y |

BID is two times per day
QW is once a week
*Dose of exenatide (exendin 4)
**Dose of LAR formulation containing 5% exenatide (exendin-4)
***Groups with the same letter were given equal volumes of medication During the three-day lead-in period subjects were instructed to fast (no food or beverage, except water) for at least 8 hours beginning the evening prior to each visit. Lead-in medication (exenatide [exendin-4] 5 µg or placebo) was administered SC, BID, within 15 minutes prior to meals in the morning and evening. If a meal was skipped, the lead-in medication was administered and followed by a snack 15 minutes later. Administrations were given no sooner than 6 hours apart. Subjects received either exenatide 5 ug administered subcutaneously, or an equivalent dose volume of placebo, two times per day (BID). Exenatide injection (Exenatide BID) used in this study was a clear, colorless, sterile preserved solution for SC injection containing exenatide (exendin-4) in sodium acetate buffer, pH 4.5, 4.3% mannitol as an iso-osmolality modifier and 0.22% metacresol as a preservative. The strength of exenatide injection is 0.25 mg/mL of exendin-4. The placebo injection is the same as the active formulation of exenatide injection except that the active ingredient (exendin-4) is omitted.

During the 15-week treatment period, subjects received weekly subcutaneous injections of exenatide LAR, at either 0.8 mg or 2.0 mg per dose, or an equivalent dose volume of placebo LAR. Subjects were also monitored for 12 weeks after the treatment period for safety and pharmacokinetic assessment.

Exenatide LAR is a sustained-release formulation of exenatide (exendin-4) designed to provide exenatide release over a period ranging from 7 to 91 days. Exenatide LAR used in this study contained, on a w/w basis, 5% exenatide, 2% sucrose, and 93% MEDISORB® 50:50 poly D,L-lactic co-glycolic acid. The vial containing the white to off-white dry powder (2.8 mg of exenatide LAR microspheres) was stored frozen in a freezer with a recorded temperature at $\leq$−20±5° C. at the study site. The placebo LAR was the same as the active formulation of exenatide LAR except that the active ingredient (exenatide) was replaced with 0.5% ammonium sulfate.

Subjects were monitored weekly for body weight, vital signs (including blood pressure, heart rate, respiratory rate, and temperature), urinalysis, and adverse events. In addition, blood was drawn to assess plasma concentrations of exendin and glucose. $HbA_{1c}$ was determined every three weeks. Body mass index was calculated using a nomogram.

Seven-point self monitored blood glucose (SMBG) measurements were performed during 3 days between Day −7 and Day −3, and between Week 14 and Week 15. An individual 7-point SMBG profile encompassed one day, with three glucose measurements obtained preprandial (within 15 minutes prior to the meal) and three glucose measurements obtained postprandial (1.5 to 2 hours after the meal) for the three main meals of the day. The seventh measurement was taken at 0300 h.

Plasma exenatide was quantified by a validated Enzyme-Linked Immunosorbent Assay (ELISA) (Fineman et al., *Diabetes Care*, 26:2370-2377, 2003) at LINCO Diagnostic Services, Inc (St. Charles, Mo.). Glycosylated hemoglobin was quantitated by Quintiles Laboratories (Smyrna, Ga.) using high-performance liquid chromatography (Davis et al., *Diabetes*, 27:102-107, 1978; Cole et al., *Metabolism*, 27:289-301, 1978). Anti-exenatide antibodies were measured in a similar fashion to that described previously (Fineman et al., *Diabetes Care*, 26:2370-2377, 2003) at LINCO Diagnostic Services.

A sample size of 36 subjects was estimated to provide 95% confidence intervals of approximately 65 to 115 pg/mL and 170 to 290 pg/mL for the mean exenatide concentrations at steady state for 0.8 and 2.0 mg exenatide LAR, respectively. The intent-to-treat (ITT) population comprised all randomized subjects who received at least one injection of lead-in medication, while the evaluable population consisted of subjects who completed the study procedures through Week 15 in compliance with the protocol. Descriptive statistics on demographics, safety, glycemic endpoints and weight were provided for the ITT population. Descriptive statistics for percentage of subjects achieving glycosylated hemoglobin $\leq$7.0% and self-monitored blood glucose measurements were performed for the evaluable population. Plasma exenatide concentrations by treatment and time were provided for those subjects who received exenatide LAR and completed the study. Exenatide pharmacokinetics were analyzed by noncompartmental methods and summarized descriptively. The 95% confidence intervals for the differences for baseline to Week 15 changes for the 0.8 mg and 2.0 mg exenatide LAR groups, as compared to the placebo LAR group, were calculated for glycosylated hemoglobin, fasting plasma glucose, and body weight. Differences for which the 95% confidence intervals did not include zero were considered significant.

Mean steady-state exenatide concentrations (0.8 mg: 111 pg/mL, 2.0 mg: 232 pg/mL) were reached between Weeks 6 and 7 and were sustained within the targeted range throughout the treatment period (Week 15). After completion of the treatment phase at Week 15, exenatide concentrations decreased steadily. (FIG. 1)

Figure 2A:
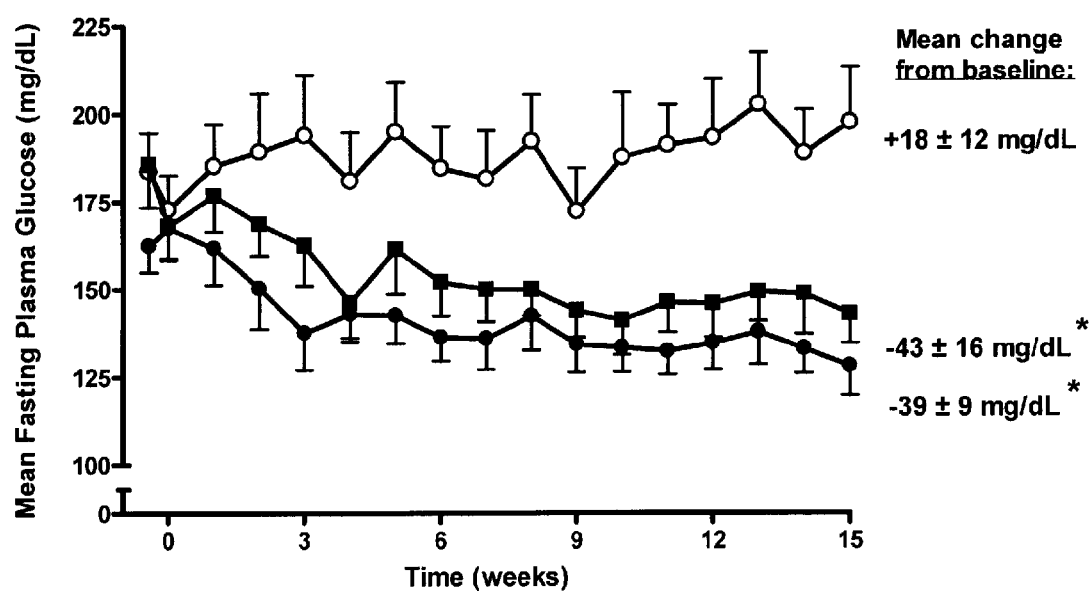
FIGS. 2A-D. Glycemic parameters. (2A) Fasting plasma glucose concentrations from baseline over time (ITT, N=45; mean±SE). ○=placebo LAR, N=14, baseline 184 mg/dL, ■=0.8 mg exenatide LAR, N=16, baseline 186 mg/dL, ●=2.0 mg exenatide LAR, N=15, baseline 167 mg/dL. (2B) Self-monitored blood glucose concentration profiles at baseline and Week 15 (evaluable, N=43; mean±SE). Preprandial glucose was measured 15 minutes before each meal, postprandial glucose 1.5 to 2 hours after each meal, and an additional glucose measurement was taken at 0300 h. Measurements were recorded on three separate days for both baseline and Week 15. ○=placebo LAR, N=12, ■=0.8 mg exenatide LAR, N=16, ●=2.0 mg exenatide LAR, N=15. (2C) Glycosylated hemoglobin (%) over time (ITT, N=45; mean±SE). ○=placebo LAR, N=14, baseline 8.6%, ■=0.8 mg exenatide LAR, N=16, baseline 8.6%, ●2.0 mg exenatide LAR, N=15, baseline 8.3%. (2D) Proportion of evaluable subjects with a Week 15 glycosylated hemoglobin measurement with baseline glycosylated hemoglobin >7% (N=41) achieving glycosylated hemoglobin ≦57% at Week 15. * indicates statistically significant results (compared to placebo).

Fasting plasma glucose was reduced at the first measurement after exenatide LAR administration (Week 1), with significant changes from baseline to Week 15 of −43±16 mg/dL (mean±SE) and −39±9 mg/dL for the 0.8 and 2.0 mg exenatide LAR groups, respectively, compared to +18±12 mg/dL for the placebo LAR group. After 15 weeks of exenatide LAR treatment, mean fasting plasma glucose values were 143 mg/dL and 128 mg/dL in the 0.8 and 2.0 mg exenatide LAR groups, compared to 198 mg/dL for the placebo LAR group (FIG. 2A).

Figure 2B:
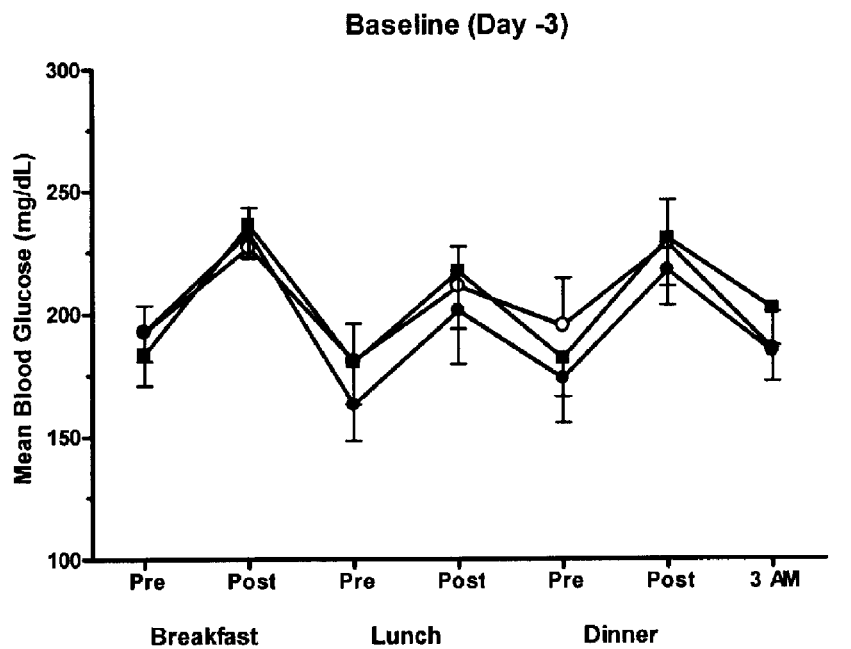
Figure 2B:
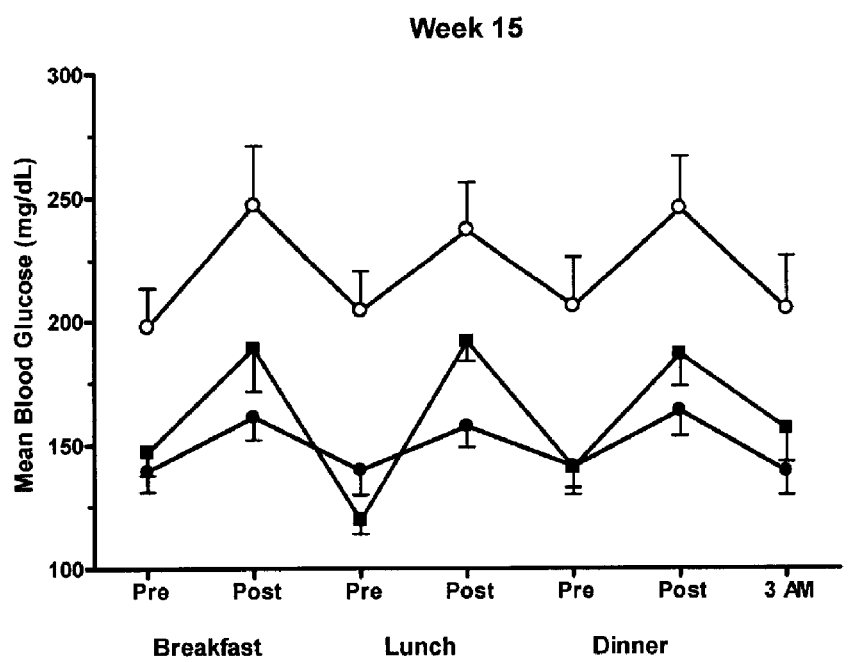

All 3 groups (0.8 mg, 2.0 mg & placebo) had similar self-monitored blood glucose profiles and similar mean average daily blood glucose concentrations at baseline (placebo LAR: 203 mg/dL, 0.8 mg: 205 mg/dL, 2.0 mg: 195 mg/dL) (FIG. 2B). By Week 15, the mean average daily blood glucose concentrations decreased for both LAR treatment groups (0.8 mg: to 165 mg/dL, 2.0 mg: to 149 mg/dL) and the mean average daily blood glucose concentration rose for the placebo LAR group (to 220 mg/dL). Preprandial and postprandial plasma glucose concentrations decreased for both exenatide LAR groups, with the magnitude of postprandial excursions decreased by as much as four-fold with 2.0 mg exenatide LAR compared to placebo LAR.

Figure 2C:
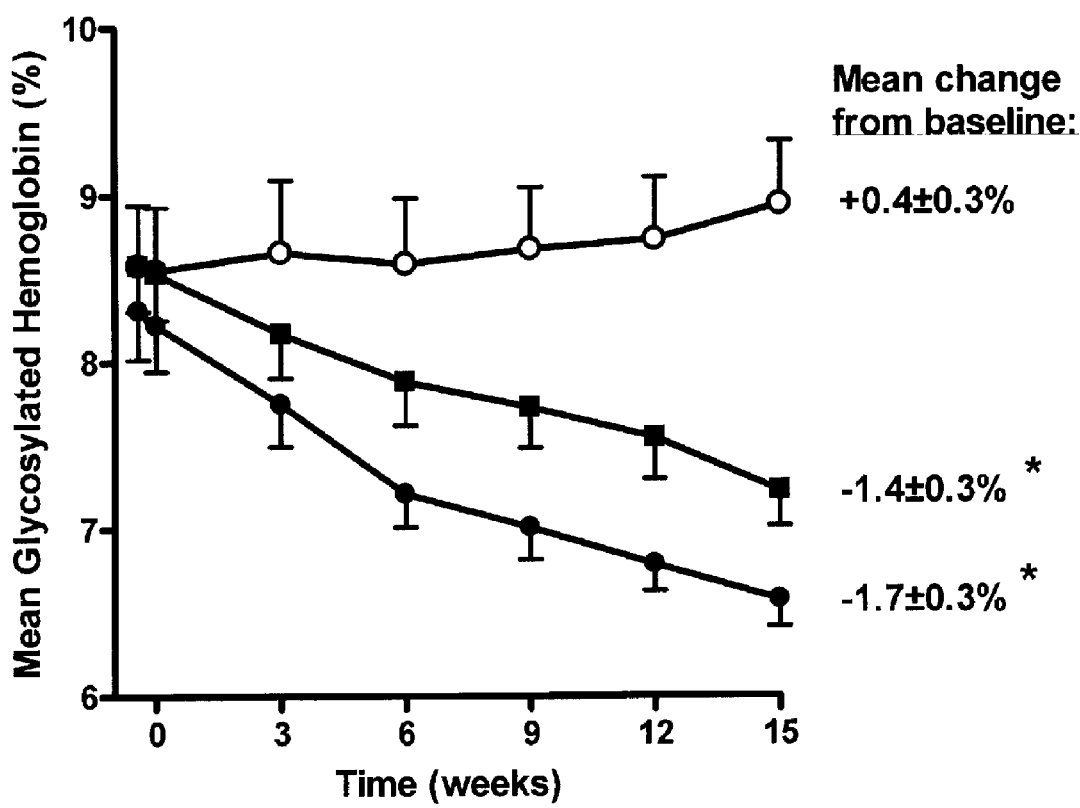
Figure 2D:
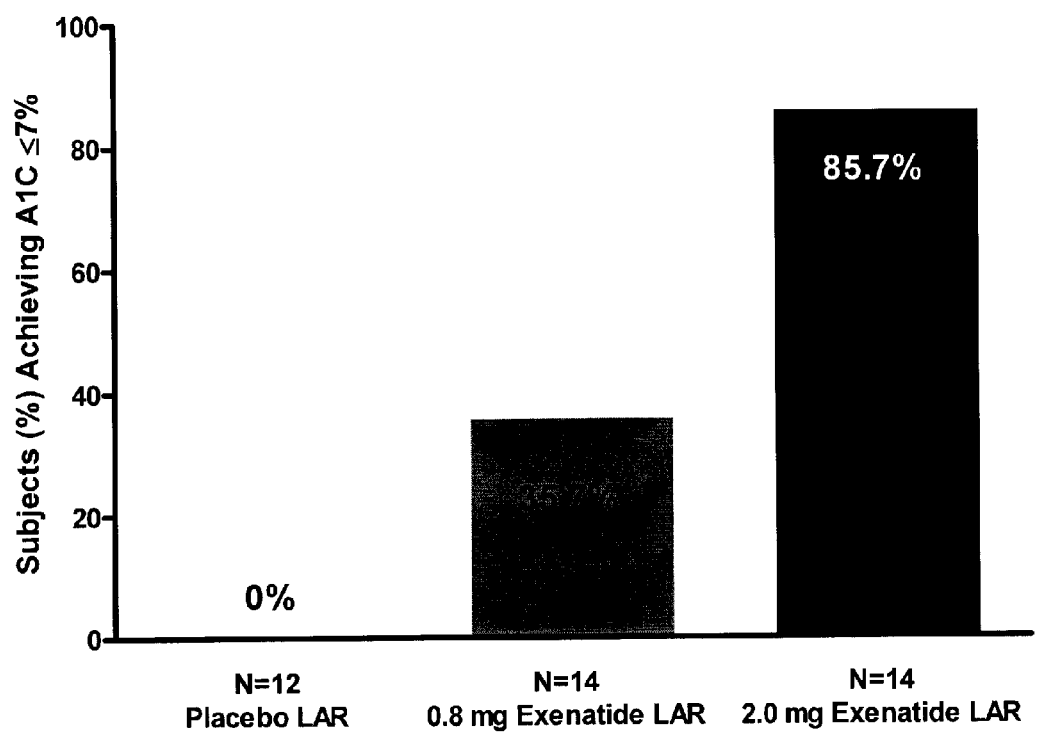

Glycosylated hemoglobin was reduced at the first post-exenatide LAR measurement (Week 3) for both exenatide LAR groups and progressively decreased throughout the treatment period (FIG. 2C). At Week 15, significant glycosylated hemoglobin changes from baseline of −1.4±0.3% and −1.7±0.3% were observed for the 0.8 and 2.0 mg exenatide LAR groups, respectively, compared to +0.4±0.3% for the placebo LAR group, resulting in mean glycosylated hemoglobin values of 7.2% and 6.6% in the 0.8 and 2.0 mg exenatide LAR groups, compared to 9.0% for the placebo LAR group. Eighty-six percent of subjects with baseline glycosylated hemoglobin >7% in the 2.0 mg group and 36% of subjects in the 0.8 mg group achieved achieved a glycosylated hemoglobin of ≦7% at Week 15, compared to 0% of subjects in the placebo LAR group (FIG. 2D).

Figure 3:
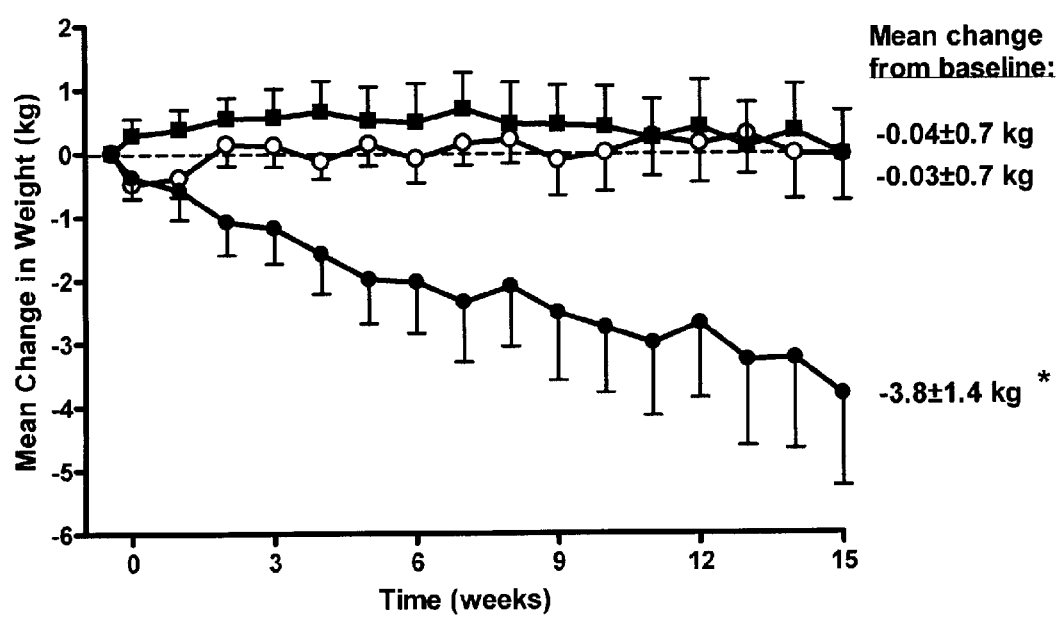
FIG. 3. Change in body weight from baseline over time (ITT, N=45; mean±SE). * indicates statistically significant results (compared to placebo). ○=placebo LAR, N=14, baseline 101.2 kg, ■=0.8 mg exenatide LAR, N=16, baseline 106.6 kg, ●=2.0 mg exenatide LAR, N=15, baseline 109.7 kg.

Body weight decreased progressively with 2.0 mg exenatide LAR treatment, with a significant change from baseline at Week 15 of −3.8±1.5 kg (3.5% of total body weight) (FIG. 3). Body weight was essentially unchanged for the 0.8 mg exenatide LAR and placebo LAR groups.

It is to be understood that the present invention has been described in detail by way of illustration and example in order to acquaint others skilled in the art with the invention, its principles, and its practical application. Particular formulations and processes of the present invention are not limited to the descriptions of the specific embodiments presented, but rather the descriptions and examples should be viewed in terms of the claims that follow and their equivalents. While some of the examples and descriptions above include some conclusions about the way the invention may function, the inventor does not intend to be bound by those conclusions and functions, but puts them forth only as possible explanations.

It is to be further understood that the specific embodiments of the present invention as set forth are not intended as being exhaustive or limiting of the invention, and that many alternatives, modifications, and variations will be apparent to those of ordinary skill in the art in light of the foregoing examples and detailed description. Accordingly, this invention is intended to embrace all such alternatives, modifications, and variations that fall within the scope of the following claims.

---

What is claimed is:

1. A method for treating diabetes in a human in need thereof comprising administering to the human an effective amount of a pharmaceutical composition comprising a biocompatible poly(lactide-co-glycolide) copolymer and exendin-4 or an exendin analog to achieve a mean steady state plasma concentration of the exendin-4 or the exendin-4 analog at least 170 pg/ml for at least one month in the human to treat diabetes.

2. The method of claim 1, wherein the pharmaceutical composition comprises exendin-4.

3. The method of claim 2, wherein the pharmaceutical composition further comprises a sugar.

4. The method of claim 1, wherein the pharmaceutical composition comprises the exendin analog.

5. The method of claim 4, wherein the exendin analog comprises the amino acid sequence of any one of SEQ ID NOs: 2 and 9-142.

6. The method of claim 1, wherein the poly(lactide-co-glycolide) copolymer is purified 50:50 (lactide:glycolide) poly(D,L-lactide-co-glycolide).

7. The method of claim 1, wherein the pharmaceutical composition is administered to the human once weekly.

8. The method of claim 1, wherein the exendin-4 or the exendin analog is present in the pharmaceutical composition in an amount of 1.0 mg to 5.0 mg.

9. The method of claim 1, wherein the pharmaceutical composition comprises 5% (w/w) exendin-4, 2% (w/w) sucrose, and 93% (w/w) poly(lactide-co-glycolide)copolymer.

10. The method of claim 1, wherein the mean steady state plasma concentration of exendin-4 or the exendin analog is 170 pg/ml to 600 pg/ml.

11. The method of claim 1, wherein the mean steady state plasma concentration of exendin-4 or the exendin analog is 170 pg/ml to 350 pg/ml.

12. The method of claim 1, wherein the mean steady state plasma concentration of exendin-4 or the exendin analog is 170 pg/ml to 290 pg/ml.

13. The method of claim 1, wherein the diabetes is type 2 diabetes.

14. The method of claim 1, wherein the diabetes is type 1 diabetes.

15. A method for reducing one or more of HbA1C, fasting plasma glucose, and body weight in a human in need thereof comprising administering to the human an effective amount of a pharmaceutical composition comprising a biocompatible poly(lactide-co-glycolide) copolymer and exendin-4 or an exendin analog in an amount to achieve a mean steady state concentration of exendin-4 or the exendin analog of at least 170 pg/ml for at least one month to reduce one or more of HbA1C, fasting plasma glucose, and body weight.

16. The method of claim 15, wherein the pharmaceutical composition comprises exendin-4.

17. The method of claim 15, wherein the method is for reducing HbA1C.

18. The method of claim 15, wherein the method is for reducing fasting plasma glucose.

19. The method of claim 15, wherein the method is for reducing body weight.

20. A method for treating type 2 diabetes in a human in need thereof comprising administering once weekly to the human an effective amount of a pharmaceutical composition comprising 5% (w/w) exendin-4, 2% (w/w) sucrose, and 93% (w/w) poly(lactide-co-glycolide)copolymer to achieve a mean steady state plasma concentration of exendin-4 at 170 pg/ml to 350 pg/ml for at least one month in the human to treat Type 2 diabetes.

* * * * *

SEQUENCE LISTING

```
<160> NUMBER OF SEQ ID NOS: 142

<210> SEQ ID NO 1
<211> LENGTH: 39
<212> TYPE: PRT
<213> ORGANISM: Heloderma horridum
<220> FEATURE:
<221> NAME/KEY: MOD_RES
<222> LOCATION: (39)..(39)
<223> OTHER INFORMATION: AMIDATION

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 2
<211> LENGTH: 39
<212> TYPE: PRT
<213> ORGANISM: Heloderma suspectum
<220> FEATURE:
<221> NAME/KEY: MOD_RES
<222> LOCATION: (39)..(39)
<223> OTHER INFORMATION: AMIDATION

<400> SEQUENCE: 2

His Ser Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30
```

Ser Gly Ala Pro Pro Ser
        35

<210> SEQ ID NO 3
<211> LENGTH: 30
<212> TYPE: PRT
<213> ORGANISM: Homo sapiens
<220> FEATURE:
<221> NAME/KEY: MOD_RES
<222> LOCATION: (30)..(30)
<223> OTHER INFORMATION: AMIDATION

<400> SEQUENCE: 3

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 4
<211> LENGTH: 31
<212> TYPE: PRT
<213> ORGANISM: Heloderma horridum
<220> FEATURE:
<221> NAME/KEY: MOD_RES
<222> LOCATION: (31)..(31)
<223> OTHER INFORMATION: AMIDATION

<400> SEQUENCE: 4

Asp Leu Ser Lys Gln Met Glu Glu Glu Ala Val Arg Leu Phe Ile Glu
1               5                   10                  15

Trp Leu Lys Asn Gly Gly Pro Ser Ser Gly Ala Pro Pro Ser
            20                  25                  30

<210> SEQ ID NO 5
<211> LENGTH: 38
<212> TYPE: PRT
<213> ORGANISM: Heloderma horridum

<400> SEQUENCE: 5

His Ser Asp Ala Thr Phe Thr Ala Glu Tyr Ser Lys Leu Leu Ala Lys
1               5                   10                  15

Leu Ala Leu Gln Lys Tyr Leu Glu Ser Ile Leu Gly Ser Ser Thr Ser
            20                  25                  30

Pro Arg Pro Pro Ser Ser
        35

<210> SEQ ID NO 6
<211> LENGTH: 37
<212> TYPE: PRT
<213> ORGANISM: Heloderma horridum

<400> SEQUENCE: 6

His Ser Asp Ala Thr Phe Thr Ala Glu Tyr Ser Lys Leu Leu Ala Lys
1               5                   10                  15

Leu Ala Leu Gln Lys Tyr Leu Glu Ser Ile Leu Gly Ser Ser Thr Ser
            20                  25                  30

Pro Arg Pro Pro Ser
        35

<210> SEQ ID NO 7
<211> LENGTH: 35
<212> TYPE: PRT
<213> ORGANISM: Heloderma suspectum
<220> FEATURE:

```
<221> NAME/KEY: MOD_RES
<222> LOCATION: (35)..(35)
<223> OTHER INFORMATION: AMIDATION

<400> SEQUENCE: 7

His Ser Asp Ala Ile Phe Thr Glu Glu Tyr Ser Lys Leu Leu Ala Lys
1               5                   10                  15

Leu Ala Leu Gln Lys Tyr Leu Ala Ser Ile Leu Gly Ser Arg Thr Ser
            20                  25                  30

Pro Pro Pro
        35

<210> SEQ ID NO 8
<211> LENGTH: 35
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (35)..(35)
<223> OTHER INFORMATION: AMIDATION

<400> SEQUENCE: 8

His Ser Asp Ala Ile Phe Thr Gln Gln Tyr Ser Lys Leu Leu Ala Lys
1               5                   10                  15

Leu Ala Leu Gln Lys Tyr Leu Ala Ser Ile Leu Gly Ser Arg Thr Ser
            20                  25                  30

Pro Pro Pro
        35

<210> SEQ ID NO 9
<211> LENGTH: 30
<212> TYPE: PRT
<213> ORGANISM: Artificial Sequence
<220> FEATURE:
<223> OTHER INFORMATION: synthetic peptide construct

<400> SEQUENCE: 9

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly
            20                  25                  30

<210> SEQ ID NO 10
<211> LENGTH: 30
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (30)..(30)
<223> OTHER INFORMATION: AMIDATION

<400> SEQUENCE: 10

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly
            20                  25                  30

<210> SEQ ID NO 11
<211> LENGTH: 28
<212> TYPE: PRT
<213> ORGANISM: Artificial Sequence
<220> FEATURE:
```

```
<223> OTHER INFORMATION: synthetic peptide construct
<220> FEATURE:
<221> NAME/KEY: MOD_RES
<222> LOCATION: (28)..(28)
<223> OTHER INFORMATION: AMIDATION

<400> SEQUENCE: 11

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn
            20                  25

<210> SEQ ID NO 12
<211> LENGTH: 39
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (39)..(39)
<223> OTHER INFORMATION: AMIDATION

<400> SEQUENCE: 12

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala Pro Pro Pro Ser
        35

<210> SEQ ID NO 13
<211> LENGTH: 28
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (28)..(28)
<223> OTHER INFORMATION: AMIDATION

<400> SEQUENCE: 13

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 14
<211> LENGTH: 28
<212> TYPE: PRT
<213> ORGANISM: Artificial Sequence
<220> FEATURE:
<221> NAME/KEY: MOD_RES
<222> LOCATION: (28)..(28)
<223> OTHER INFORMATION: AMIDATION
<220> FEATURE:
<223> OTHER INFORMATION: synthetic peptide construct

<400> SEQUENCE: 14

His Gly Glu Gly Thr Phe Thr Ser Asp Leu Ser Lys Gln Leu Glu Glu
1               5                   10                  15

Glu Ala Val Arg Leu Ala Ile Glu Phe Leu Lys Asn
            20                  25

<210> SEQ ID NO 15
<211> LENGTH: 38
```

```
<212> TYPE: PRT
<213> ORGANISM: Artificial Sequence
<220> FEATURE:
<223> OTHER INFORMATION: synthetic peptide construct
<220> FEATURE:
<221> NAME/KEY: MISC_FEATURE
<222> LOCATION: (1)..(1)
<223> OTHER INFORMATION: His, Arg, or Tyr
<220> FEATURE:
<221> NAME/KEY: MISC_FEATURE
<222> LOCATION: (2)..(2)
<223> OTHER INFORMATION: Ser, Gly, Ala or Thr
<220> FEATURE:
<221> NAME/KEY: MISC_FEATURE
<222> LOCATION: (3)..(3)
<223> OTHER INFORMATION: Ala, Asp or Glu
<220> FEATURE:
<221> NAME/KEY: MISC_FEATURE
<222> LOCATION: (4)..(4)
<223> OTHER INFORMATION: Gly, Ala or Thr
<220> FEATURE:
<221> NAME/KEY: MISC_FEATURE
<222> LOCATION: (5)..(5)
<223> OTHER INFORMATION: Ala or Thr
<220> FEATURE:
<221> NAME/KEY: MISC_FEATURE
<222> LOCATION: (6)..(6)
<223> OTHER INFORMATION: Ala, Phe, Tyr or naphthylalanine
<220> FEATURE:
<221> NAME/KEY: MISC_FEATURE
<222> LOCATION: (7)..(7)
<223> OTHER INFORMATION: Thr or Ser
<220> FEATURE:
<221> NAME/KEY: MISC_FEATURE
<222> LOCATION: (8)..(8)
<223> OTHER INFORMATION: Ala, Ser or Thr
<220> FEATURE:
<221> NAME/KEY: MISC_FEATURE
<222> LOCATION: (9)..(9)
<223> OTHER INFORMATION: Asp or Glu
<220> FEATURE:
<221> NAME/KEY: MISC_FEATURE
<222> LOCATION: (10)..(10)
<223> OTHER INFORMATION: Ala, Leu, Ile, Val, pentylglycine or Met
<220> FEATURE:
<221> NAME/KEY: MISC_FEATURE
<222> LOCATION: (11)..(11)
<223> OTHER INFORMATION: Ala or Ser
<220> FEATURE:
<221> NAME/KEY: MISC_FEATURE
<222> LOCATION: (12)..(12)
<223> OTHER INFORMATION: Ala or Lys
<220> FEATURE:
<221> NAME/KEY: MISC_FEATURE
<222> LOCATION: (13)..(13)
<223> OTHER INFORMATION: Ala or Gln
<220> FEATURE:
<221> NAME/KEY: MISC_FEATURE
<222> LOCATION: (14)..(14)
<223> OTHER INFORMATION: Ala, Leu, Ile, pentylglycine, Val or Met
<220> FEATURE:
<221> NAME/KEY: MISC_FEATURE
<222> LOCATION: (15)..(15)
<223> OTHER INFORMATION: Ala or Glu
<220> FEATURE:
<221> NAME/KEY: MISC_FEATURE
<222> LOCATION: (16)..(16)
<223> OTHER INFORMATION: Ala or Glu
<220> FEATURE:
<221> NAME/KEY: MISC_FEATURE
<222> LOCATION: (17)..(17)
<223> OTHER INFORMATION: Ala or Glu
<220> FEATURE:
<221> NAME/KEY: MISC_FEATURE
<222> LOCATION: (19)..(19)
<223> OTHER INFORMATION: Ala or Val
<220> FEATURE:
<221> NAME/KEY: MISC_FEATURE
<222> LOCATION: (20)..(20)
<223> OTHER INFORMATION: Ala or Arg
```

```
<220> FEATURE:
<221> NAME/KEY: MISC_FEATURE
<222> LOCATION: (21)..(21)
<223> OTHER INFORMATION: Ala or Leu
<220> FEATURE:
<221> NAME/KEY: MISC_FEATURE
<222> LOCATION: (22)..(22)
<223> OTHER INFORMATION: Ala, Phe, Tyr or naphthylalanine
<220> FEATURE:
<221> NAME/KEY: MISC_FEATURE
<222> LOCATION: (23)..(23)
<223> OTHER INFORMATION: Ile, Val, Leu, pentylglycine, tert-butylglycine
      or Met
<220> FEATURE:
<221> NAME/KEY: MISC_FEATURE
<222> LOCATION: (24)..(24)
<223> OTHER INFORMATION: Ala Glu or Asp
<220> FEATURE:
<221> NAME/KEY: MISC_FEATURE
<222> LOCATION: (25)..(25)
<223> OTHER INFORMATION: Ala, Trp, Phe, Tyr or naphthylalanine
<220> FEATURE:
<221> NAME/KEY: MISC_FEATURE
<222> LOCATION: (26)..(26)
<223> OTHER INFORMATION: Ala or Leu
<220> FEATURE:
<221> NAME/KEY: MISC_FEATURE
<222> LOCATION: (27)..(27)
<223> OTHER INFORMATION: Ala or Lys
<220> FEATURE:
<221> NAME/KEY: MISC_FEATURE
<222> LOCATION: (28)..(28)
<223> OTHER INFORMATION: Ala or Asn and is optionally amidated
<220> FEATURE:
<221> NAME/KEY: MISC_FEATURE
<222> LOCATION: (29)..(29)
<223> OTHER INFORMATION: Gly or absent and if present optionally
      amidated
<220> FEATURE:
<221> NAME/KEY: MISC_FEATURE
<222> LOCATION: (30)..(30)
<223> OTHER INFORMATION: Gly or absent and if present optionally
      amidated
<220> FEATURE:
<221> NAME/KEY: MISC_FEATURE
<222> LOCATION: (31)..(31)
<223> OTHER INFORMATION: Pro, homoproline, 3Hyp, 4Hyp, Thioproline,
      N-alkylglycine, N-alkylpentylglycine,
      N-alkylalanine or absent and if present
      optionally amidated
<220> FEATURE:
<221> NAME/KEY: MISC_FEATURE
<222> LOCATION: (32)..(32)
<223> OTHER INFORMATION: Ser or absent and if present optionally
      amidated
<220> FEATURE:
<221> NAME/KEY: MISC_FEATURE
<222> LOCATION: (33)..(33)
<223> OTHER INFORMATION: Ser or absent and if present optionally
      amidated
<220> FEATURE:
<221> NAME/KEY: MISC_FEATURE
<222> LOCATION: (34)..(34)
<223> OTHER INFORMATION: Gly or absent and if present optionally
      amidated
<220> FEATURE:
<221> NAME/KEY: MISC_FEATURE
<222> LOCATION: (35)..(35)
<223> OTHER INFORMATION: Ala or absent and if present optionally
      amidated
<220> FEATURE:
<221> NAME/KEY: MISC_FEATURE
<222> LOCATION: (36)..(38)
<223> OTHER INFORMATION: Pro, homoproline, 3Hyp, 4Hyp, Thioproline,
      N-alkylglycine, N-alkylpentylglycine,
      N-alkylalanine or absent and if present
      optionally amidated

<400> SEQUENCE: 15
```

```
Xaa Xaa Xaa Xaa Xaa Xaa Xaa Xaa Xaa Xaa Xaa Xaa Xaa Xaa
1               5                   10                  15

Xaa Ala Xaa Xaa Xaa Xaa Xaa Xaa Xaa Xaa Gly Gly Xaa Ser
            20                  25                  30

Ser Gly Ala Xaa Xaa Xaa
        35

<210> SEQ ID NO 16
<211> LENGTH: 39
<212> TYPE: PRT
<213> ORGANISM: Artificial Sequence
<220> FEATURE:
<223> OTHER INFORMATION: synthetic peptide construct
<220> FEATURE:
<221> NAME/KEY: MISC_FEATURE
<222> LOCATION: (1)..(1)
<223> OTHER INFORMATION: His, Arg, Tyr, Ala, Norval, Val or Norleu
<220> FEATURE:
<221> NAME/KEY: MISC_FEATURE
<222> LOCATION: (2)..(2)
<223> OTHER INFORMATION: Ser, Gly, Ala or Thr
<220> FEATURE:
<221> NAME/KEY: MISC_FEATURE
<222> LOCATION: (3)..(3)
<223> OTHER INFORMATION: Ala, Asp or Glu
<220> FEATURE:
<221> NAME/KEY: MISC_FEATURE
<222> LOCATION: (4)..(4)
<223> OTHER INFORMATION: Ala, Norval, Val, Norleu or Gly
<220> FEATURE:
<221> NAME/KEY: MISC_FEATURE
<222> LOCATION: (5)..(5)
<223> OTHER INFORMATION: Ala or Thr
<220> FEATURE:
<221> NAME/KEY: MISC_FEATURE
<222> LOCATION: (6)..(6)
<223> OTHER INFORMATION: Ala, Phe, Tyr or naphthylalanine
<220> FEATURE:
<221> NAME/KEY: MISC_FEATURE
<222> LOCATION: (7)..(7)
<223> OTHER INFORMATION: Thr or Ser
<220> FEATURE:
<221> NAME/KEY: MISC_FEATURE
<222> LOCATION: (8)..(8)
<223> OTHER INFORMATION: Ala, Ser or Thr
<220> FEATURE:
<221> NAME/KEY: MISC_FEATURE
<222> LOCATION: (9)..(9)
<223> OTHER INFORMATION: Ala, Norva, Val, Norleu, Asp or Glu
<220> FEATURE:
<221> NAME/KEY: MISC_FEATURE
<222> LOCATION: (10)..(10)
<223> OTHER INFORMATION: Ala, Leu, Ile, Val, pentylglycine or Met
<220> FEATURE:
<221> NAME/KEY: MISC_FEATURE
<222> LOCATION: (11)..(11)
<223> OTHER INFORMATION: Ala or Ser
<220> FEATURE:
<221> NAME/KEY: MISC_FEATURE
<222> LOCATION: (12)..(12)
<223> OTHER INFORMATION: Ala or Lys
<220> FEATURE:
<221> NAME/KEY: MISC_FEATURE
<222> LOCATION: (13)..(13)
<223> OTHER INFORMATION: Ala or Gln
<220> FEATURE:
<221> NAME/KEY: MISC_FEATURE
<222> LOCATION: (14)..(14)
<223> OTHER INFORMATION: Ala, Leu, Ile, pentylglycine, Val or Met
<220> FEATURE:
<221> NAME/KEY: MISC_FEATURE
<222> LOCATION: (15)..(17)
<223> OTHER INFORMATION: Ala or Glu
<220> FEATURE:
<221> NAME/KEY: MISC_FEATURE
<222> LOCATION: (19)..(19)
<223> OTHER INFORMATION: Ala or Val
```

```
<220> FEATURE:
<221> NAME/KEY: MISC_FEATURE
<222> LOCATION: (20)..(20)
<223> OTHER INFORMATION: Ala or Arg
<220> FEATURE:
<221> NAME/KEY: MISC_FEATURE
<222> LOCATION: (21)..(21)
<223> OTHER INFORMATION: Ala or Leu
<220> FEATURE:
<221> NAME/KEY: MISC_FEATURE
<222> LOCATION: (22)..(22)
<223> OTHER INFORMATION: Phe, Tyr or naphthylalanine
<220> FEATURE:
<221> NAME/KEY: MISC_FEATURE
<222> LOCATION: (23)..(23)
<223> OTHER INFORMATION: Ile, Val, Leu, pentylglycine, tert-butylglycine
      or Met
<220> FEATURE:
<221> NAME/KEY: MISC_FEATURE
<222> LOCATION: (24)..(24)
<223> OTHER INFORMATION: Ala, Glu or Asp
<220> FEATURE:
<221> NAME/KEY: MISC_FEATURE
<222> LOCATION: (25)..(25)
<223> OTHER INFORMATION: Ala, Trp, Phe, Tyr or naphthylalanine
<220> FEATURE:
<221> NAME/KEY: MISC_FEATURE
<222> LOCATION: (26)..(26)
<223> OTHER INFORMATION: Ala or Leu
<220> FEATURE:
<221> NAME/KEY: MISC_FEATURE
<222> LOCATION: (27)..(27)
<223> OTHER INFORMATION: Ala or Lys
<220> FEATURE:
<221> NAME/KEY: MISC_FEATURE
<222> LOCATION: (28)..(28)
<223> OTHER INFORMATION: Ala or Asn and optionally amidated
<220> FEATURE:
<221> NAME/KEY: MISC_FEATURE
<222> LOCATION: (29)..(30)
<223> OTHER INFORMATION: Gly or absent and if present optionally
      amidated
<220> FEATURE:
<221> NAME/KEY: MISC_FEATURE
<222> LOCATION: (31)..(31)
<223> OTHER INFORMATION: Pro, homoproline, 3Hyp, 4Hyp, thioproline,
      N-alkylglycine, N-alkylpentylglycine or
      N-alkylalanine or absent and if present
      optionally amidated
<220> FEATURE:
<221> NAME/KEY: MISC_FEATURE
<222> LOCATION: (32)..(33)
<223> OTHER INFORMATION: Ser or absent and if present optionally
      amidated
<220> FEATURE:
<221> NAME/KEY: MISC_FEATURE
<222> LOCATION: (34)..(34)
<223> OTHER INFORMATION: Gly or absent and if present optionally
      amidated
<220> FEATURE:
<221> NAME/KEY: MISC_FEATURE
<222> LOCATION: (36)..(38)
<223> OTHER INFORMATION: Pro, homoproline, 3Hyp, 4Hyp, thioproline,
      N-alkylglycine, N-alkylpentylglycine or
      N-alkylalanine or absent and if present
      optionally amidated
<220> FEATURE:
<221> NAME/KEY: MISC_FEATURE
<222> LOCATION: (39)..(39)
<223> OTHER INFORMATION: Ser, Tyr or absent and if present
      optionally amidated

<400> SEQUENCE: 16

Xaa Xaa Xaa Xaa Xaa Xaa Xaa Xaa Xaa Xaa Xaa Xaa Xaa Xaa Xaa
1               5                   10                  15

Xaa Ala Xaa Xaa Xaa Xaa Xaa Xaa Xaa Xaa Xaa Xaa Gly Gly Xaa Ser
            20                  25                  30
```

Ser Gly Ala Xaa Xaa Xaa Xaa
        35

<210> SEQ ID NO 17
<211> LENGTH: 38
<212> TYPE: PRT
<213> ORGANISM: Artificial Sequence
<220> FEATURE:
<223> OTHER INFORMATION: synthetic peptide construct
<220> FEATURE:
<221> NAME/KEY: MISC_FEATURE
<222> LOCATION: (1)..(1)
<223> OTHER INFORMATION: His or Arg
<220> FEATURE:
<221> NAME/KEY: MISC_FEATURE
<222> LOCATION: (2)..(2)
<223> OTHER INFORMATION: Gly or Ala
<220> FEATURE:
<221> NAME/KEY: MISC_FEATURE
<222> LOCATION: (3)..(3)
<223> OTHER INFORMATION: Ala, Asp or Glu
<220> FEATURE:
<221> NAME/KEY: MISC_FEATURE
<222> LOCATION: (5)..(5)
<223> OTHER INFORMATION: Ala or Thr
<220> FEATURE:
<221> NAME/KEY: MISC_FEATURE
<222> LOCATION: (6)..(6)
<223> OTHER INFORMATION: Ala, Phe or naphthylalanine
<220> FEATURE:
<221> NAME/KEY: MISC_FEATURE
<222> LOCATION: (7)..(7)
<223> OTHER INFORMATION: Thr or Ser
<220> FEATURE:
<221> NAME/KEY: MISC_FEATURE
<222> LOCATION: (8)..(8)
<223> OTHER INFORMATION: Ala, Ser or Thr
<220> FEATURE:
<221> NAME/KEY: MISC_FEATURE
<222> LOCATION: (9)..(9)
<223> OTHER INFORMATION: Asp or Glu
<220> FEATURE:
<221> NAME/KEY: MISC_FEATURE
<222> LOCATION: (10)..(10)
<223> OTHER INFORMATION: Ala, Leu or pentylglycine
<220> FEATURE:
<221> NAME/KEY: MISC_FEATURE
<222> LOCATION: (11)..(11)
<223> OTHER INFORMATION: Ala or Ser
<220> FEATURE:
<221> NAME/KEY: MISC_FEATURE
<222> LOCATION: (12)..(12)
<223> OTHER INFORMATION: Ala or Lys
<220> FEATURE:
<221> NAME/KEY: MISC_FEATURE
<222> LOCATION: (13)..(13)
<223> OTHER INFORMATION: Ala or Gln
<220> FEATURE:
<221> NAME/KEY: MISC_FEATURE
<222> LOCATION: (14)..(14)
<223> OTHER INFORMATION: Ala, Leu or pentylglycine
<220> FEATURE:
<221> NAME/KEY: MISC_FEATURE
<222> LOCATION: (15)..(17)
<223> OTHER INFORMATION: Ala or Glu
<220> FEATURE:
<221> NAME/KEY: MISC_FEATURE
<222> LOCATION: (19)..(19)
<223> OTHER INFORMATION: Ala or Val
<220> FEATURE:
<221> NAME/KEY: MISC_FEATURE
<222> LOCATION: (20)..(20)
<223> OTHER INFORMATION: Ala or Arg
<220> FEATURE:
<221> NAME/KEY: MISC_FEATURE
<222> LOCATION: (21)..(21)
<223> OTHER INFORMATION: Ala or Leu
<220> FEATURE:
<221> NAME/KEY: MISC_FEATURE

```
<222> LOCATION: (22)..(22)
<223> OTHER INFORMATION: Phe or napthylalanine
<220> FEATURE:
<221> NAME/KEY: MISC_FEATURE
<222> LOCATION: (23)..(23)
<223> OTHER INFORMATION: Ile, Val or tert-butylglycine
<220> FEATURE:
<221> NAME/KEY: MISC_FEATURE
<222> LOCATION: (24)..(24)
<223> OTHER INFORMATION: Ala, Glu or Asp
<220> FEATURE:
<221> NAME/KEY: MISC_FEATURE
<222> LOCATION: (25)..(25)
<223> OTHER INFORMATION: Ala, Trp or Phe
<220> FEATURE:
<221> NAME/KEY: MISC_FEATURE
<222> LOCATION: (26)..(26)
<223> OTHER INFORMATION: Ala or Leu
<220> FEATURE:
<221> NAME/KEY: MISC_FEATURE
<222> LOCATION: (27)..(27)
<223> OTHER INFORMATION: Ala or Lys
<220> FEATURE:
<221> NAME/KEY: MISC_FEATURE
<222> LOCATION: (28)..(28)
<223> OTHER INFORMATION: Ala or Asn and optionally amidated
<220> FEATURE:
<221> NAME/KEY: MISC_FEATURE
<222> LOCATION: (29)..(30)
<223> OTHER INFORMATION: Gly or absent and if present optionally
      amidated
<220> FEATURE:
<221> NAME/KEY: MISC_FEATURE
<222> LOCATION: (31)..(31)
<223> OTHER INFORMATION: Pro, homoproline, thioproline N-methylalanine
      or absent and if present optionally amidated
<220> FEATURE:
<221> NAME/KEY: MISC_FEATURE
<222> LOCATION: (32)..(33)
<223> OTHER INFORMATION: Ser or absent and if present optionally
      amidated
<220> FEATURE:
<221> NAME/KEY: MISC_FEATURE
<222> LOCATION: (34)..(34)
<223> OTHER INFORMATION: Gly or absent and if present optionally
      amidated
<220> FEATURE:
<221> NAME/KEY: MISC_FEATURE
<222> LOCATION: (35)..(35)
<223> OTHER INFORMATION: Ala or absent and if present optionally
      amidated
<220> FEATURE:
<221> NAME/KEY: MISC_FEATURE
<222> LOCATION: (36)..(38)
<223> OTHER INFORMATION: Pro, homoproline, thioproline N-methylalanine
      or absent and if present optionally amidated

<400> SEQUENCE: 17

Xaa Xaa Xaa Gly Xaa Xaa Xaa Xaa Xaa Xaa Xaa Xaa Xaa Xaa Xaa Xaa
1               5                   10                  15

Xaa Ala Xaa Xaa Xaa Xaa Xaa Xaa Xaa Xaa Xaa Xaa Gly Gly Xaa Ser
            20                  25                  30

Ser Gly Ala Xaa Xaa Xaa
            35

<210> SEQ ID NO 18
<211> LENGTH: 39
<212> TYPE: PRT
<213> ORGANISM: Artificial Sequence
<220> FEATURE:
<223> OTHER INFORMATION: synthetic peptide construct
<220> FEATURE:
<221> NAME/KEY: MISC_FEATURE
<222> LOCATION: (1)..(1)
<223> OTHER INFORMATION: His or Ala
<220> FEATURE:
```

-continued

```
<221> NAME/KEY: MISC_FEATURE
<222> LOCATION: (2)..(2)
<223> OTHER INFORMATION: Gly or Ala
<220> FEATURE:
<221> NAME/KEY: MISC_FEATURE
<222> LOCATION: (3)..(3)
<223> OTHER INFORMATION: Ala, Asp or Glu
<220> FEATURE:
<221> NAME/KEY: MISC_FEATURE
<222> LOCATION: (4)..(4)
<223> OTHER INFORMATION: Ala or Gly
<220> FEATURE:
<221> NAME/KEY: MISC_FEATURE
<222> LOCATION: (5)..(5)
<223> OTHER INFORMATION: Ala or Thr
<220> FEATURE:
<221> NAME/KEY: MISC_FEATURE
<222> LOCATION: (6)..(6)
<223> OTHER INFORMATION: Ala, Phe or naphthylalanine
<220> FEATURE:
<221> NAME/KEY: MISC_FEATURE
<222> LOCATION: (7)..(7)
<223> OTHER INFORMATION: Thr or Ser
<220> FEATURE:
<221> NAME/KEY: MISC_FEATURE
<222> LOCATION: (8)..(8)
<223> OTHER INFORMATION: Ala, Ser or Thr
<220> FEATURE:
<221> NAME/KEY: MISC_FEATURE
<222> LOCATION: (9)..(9)
<223> OTHER INFORMATION: Ala, Asp or Glu
<220> FEATURE:
<221> NAME/KEY: MISC_FEATURE
<222> LOCATION: (10)..(10)
<223> OTHER INFORMATION: Ala, Leu or pentylglycine
<220> FEATURE:
<221> NAME/KEY: MISC_FEATURE
<222> LOCATION: (11)..(11)
<223> OTHER INFORMATION: Ala or Ser
<220> FEATURE:
<221> NAME/KEY: MISC_FEATURE
<222> LOCATION: (12)..(12)
<223> OTHER INFORMATION: Ala or Lys
<220> FEATURE:
<221> NAME/KEY: MISC_FEATURE
<222> LOCATION: (13)..(13)
<223> OTHER INFORMATION: Ala or Gln
<220> FEATURE:
<221> NAME/KEY: MISC_FEATURE
<222> LOCATION: (14)..(14)
<223> OTHER INFORMATION: Ala, Leu, Met or pentylglycine
<220> FEATURE:
<221> NAME/KEY: MISC_FEATURE
<222> LOCATION: (15)..(17)
<223> OTHER INFORMATION: Ala or Glu
<220> FEATURE:
<221> NAME/KEY: MISC_FEATURE
<222> LOCATION: (19)..(19)
<223> OTHER INFORMATION: Ala or Val
<220> FEATURE:
<221> NAME/KEY: MISC_FEATURE
<222> LOCATION: (20)..(20)
<223> OTHER INFORMATION: Ala or Arg
<220> FEATURE:
<221> NAME/KEY: MISC_FEATURE
<222> LOCATION: (21)..(21)
<223> OTHER INFORMATION: Ala or Leu
<220> FEATURE:
<221> NAME/KEY: MISC_FEATURE
<222> LOCATION: (22)..(22)
<223> OTHER INFORMATION: Phe or naphthylalanine
<220> FEATURE:
<221> NAME/KEY: MISC_FEATURE
<222> LOCATION: (23)..(23)
<223> OTHER INFORMATION: Ile, Val or tert-butylglycine
<220> FEATURE:
<221> NAME/KEY: MISC_FEATURE
<222> LOCATION: (24)..(24)
<223> OTHER INFORMATION: Ala or Glu or Asp
<220> FEATURE:
```

```
<221> NAME/KEY: MISC_FEATURE
<222> LOCATION: (25)..(25)
<223> OTHER INFORMATION: Ala, Trp or Phe
<220> FEATURE:
<221> NAME/KEY: MISC_FEATURE
<222> LOCATION: (26)..(26)
<223> OTHER INFORMATION: Ala or Leu
<220> FEATURE:
<221> NAME/KEY: MISC_FEATURE
<222> LOCATION: (27)..(27)
<223> OTHER INFORMATION: Ala or Lys
<220> FEATURE:
<221> NAME/KEY: MISC_FEATURE
<222> LOCATION: (28)..(28)
<223> OTHER INFORMATION: Ala or Asn and optionally amidated
<220> FEATURE:
<221> NAME/KEY: MISC_FEATURE
<222> LOCATION: (29)..(30)
<223> OTHER INFORMATION: Gly or absent and if present optionally
      amidated
<220> FEATURE:
<221> NAME/KEY: MISC_FEATURE
<222> LOCATION: (31)..(31)
<223> OTHER INFORMATION: Pro, homoproline, thioproline, N-methylalanine
      or absent and if present optionally amidated
<220> FEATURE:
<221> NAME/KEY: MISC_FEATURE
<222> LOCATION: (32)..(33)
<223> OTHER INFORMATION: Ser or absent and if present optionally
      amidated
<220> FEATURE:
<221> NAME/KEY: MISC_FEATURE
<222> LOCATION: (34)..(34)
<223> OTHER INFORMATION: Gly or absent and if present optionally
      amidated
<220> FEATURE:
<221> NAME/KEY: MISC_FEATURE
<222> LOCATION: (35)..(35)
<223> OTHER INFORMATION: Ala or absent and if present optionally
      amidated
<220> FEATURE:
<221> NAME/KEY: MISC_FEATURE
<222> LOCATION: (36)..(38)
<223> OTHER INFORMATION: Pro, homoproline, thioproline, N-methylalanine
      or absent and if present optionally amidated
<220> FEATURE:
<221> NAME/KEY: MISC_FEATURE
<222> LOCATION: (39)..(39)
<223> OTHER INFORMATION: Ser or absent and if present optionally
      amidated

<400> SEQUENCE: 18

Xaa Xaa Xaa Xaa Xaa Xaa Xaa Xaa Xaa Xaa Xaa Xaa Xaa Xaa Xaa
1               5                   10                  15

Xaa Ala Xaa Xaa Xaa Xaa Xaa Xaa Xaa Xaa Xaa Gly Gly Xaa Ser
            20                  25                  30

Ser Gly Ala Xaa Xaa Xaa Ser
            35

<210> SEQ ID NO 19
<211> LENGTH: 38
<212> TYPE: PRT
<213> ORGANISM: Artificial Sequence
<220> FEATURE:
<223> OTHER INFORMATION: synthetic peptide construct
<220> FEATURE:
<221> NAME/KEY: MISC_FEATURE
<222> LOCATION: (1)..(1)
<223> OTHER INFORMATION: His, Arg, Tyr or imidazopropionyl
<220> FEATURE:
<221> NAME/KEY: MISC_FEATURE
<222> LOCATION: (2)..(2)
<223> OTHER INFORMATION: Ser, Gly, Ala or Thr
<220> FEATURE:
<221> NAME/KEY: MISC_FEATURE
<222> LOCATION: (3)..(3)
```

```
<223> OTHER INFORMATION: Ala, Asp or Glu
<220> FEATURE:
<221> NAME/KEY: MISC_FEATURE
<222> LOCATION: (5)..(5)
<223> OTHER INFORMATION: Ala or Thr
<220> FEATURE:
<221> NAME/KEY: MISC_FEATURE
<222> LOCATION: (6)..(6)
<223> OTHER INFORMATION: Ala, Phe, Tyr or naphthylalanine
<220> FEATURE:
<221> NAME/KEY: MISC_FEATURE
<222> LOCATION: (7)..(7)
<223> OTHER INFORMATION: Thr or Ser
<220> FEATURE:
<221> NAME/KEY: MISC_FEATURE
<222> LOCATION: (8)..(8)
<223> OTHER INFORMATION: Ala, Ser or Thr
<220> FEATURE:
<221> NAME/KEY: MISC_FEATURE
<222> LOCATION: (9)..(9)
<223> OTHER INFORMATION: Asp or Glu
<220> FEATURE:
<221> NAME/KEY: MISC_FEATURE
<222> LOCATION: (10)..(10)
<223> OTHER INFORMATION: Ala, Leu, Ile, Val, pentylglycine or Met
<220> FEATURE:
<221> NAME/KEY: MISC_FEATURE
<222> LOCATION: (11)..(11)
<223> OTHER INFORMATION: Ala or Ser
<220> FEATURE:
<221> NAME/KEY: MISC_FEATURE
<222> LOCATION: (12)..(12)
<223> OTHER INFORMATION: Ala or Lys
<220> FEATURE:
<221> NAME/KEY: MISC_FEATURE
<222> LOCATION: (13)..(13)
<223> OTHER INFORMATION: Ala or Gln
<220> FEATURE:
<221> NAME/KEY: MISC_FEATURE
<222> LOCATION: (14)..(14)
<223> OTHER INFORMATION: Ala, Leu, Ile, pentylglycine, Val or Met
<220> FEATURE:
<221> NAME/KEY: MISC_FEATURE
<222> LOCATION: (15)..(17)
<223> OTHER INFORMATION: Ala or Glu
<220> FEATURE:
<221> NAME/KEY: MISC_FEATURE
<222> LOCATION: (19)..(19)
<223> OTHER INFORMATION: Ala or Val
<220> FEATURE:
<221> NAME/KEY: MISC_FEATURE
<222> LOCATION: (20)..(20)
<223> OTHER INFORMATION: Ala or Arg
<220> FEATURE:
<221> NAME/KEY: MISC_FEATURE
<222> LOCATION: (21)..(21)
<223> OTHER INFORMATION: Ala, Leu or Lys-NH-R where R is Lys, Arg,
      C1-C10 straight chain or branched alkanoyl or cycloalkylalkanoyl
<220> FEATURE:
<221> NAME/KEY: MISC_FEATURE
<222> LOCATION: (22)..(22)
<223> OTHER INFORMATION: Phe, Tyr or naphthylalanine
<220> FEATURE:
<221> NAME/KEY: MISC_FEATURE
<222> LOCATION: (23)..(23)
<223> OTHER INFORMATION: Ile, Val, Leu, pentylglycine, tert-butylglycine
      or Met
<220> FEATURE:
<221> NAME/KEY: MISC_FEATURE
<222> LOCATION: (24)..(24)
<223> OTHER INFORMATION: Ala, Glu or Asp
<220> FEATURE:
<221> NAME/KEY: MISC_FEATURE
<222> LOCATION: (25)..(25)
<223> OTHER INFORMATION: Ala, Trp, Phe, Tyr or naphthylalanine
<220> FEATURE:
<221> NAME/KEY: MISC_FEATURE
<222> LOCATION: (26)..(26)
<223> OTHER INFORMATION: Ala or Leu
<220> FEATURE:
```

```
<221> NAME/KEY: MISC_FEATURE
<222> LOCATION: (27)..(27)
<223> OTHER INFORMATION: Lys, Asn, Ala or Lys-NH-R where R is Lys, Arg,
      C1-C10 straight chain or branched alkanoyl or cycloalkylalkanoyl
<220> FEATURE:
<221> NAME/KEY: MISC_FEATURE
<222> LOCATION: (28)..(28)
<223> OTHER INFORMATION: Lys, Asn, Ala or Lys-NH-R where R is Lys, Arg,
      C1-C10 straight chain or branched alkanoyl or cycloalkylalkanoyl
      and is optionally amidated
<220> FEATURE:
<221> NAME/KEY: MISC_FEATURE
<222> LOCATION: (29)..(30)
<223> OTHER INFORMATION: Gly or absent and if present optionally
      amidated
<220> FEATURE:
<221> NAME/KEY: MISC_FEATURE
<222> LOCATION: (31)..(31)
<223> OTHER INFORMATION: Pro, homoproline, 3Hyp, 4Hyp, thioproline,
      N-alkylglycine, N-alkylpentylglycine, N-alkylalanine or absent
      and if present is optionally amidated
<220> FEATURE:
<221> NAME/KEY: MISC_FEATURE
<222> LOCATION: (32)..(33)
<223> OTHER INFORMATION: Ser or absent and if present optionally
      amidated
<220> FEATURE:
<221> NAME/KEY: MISC_FEATURE
<222> LOCATION: (34)..(34)
<223> OTHER INFORMATION: Gly or absent and if present optionally
      amidated
<220> FEATURE:
<221> NAME/KEY: MISC_FEATURE
<222> LOCATION: (35)..(35)
<223> OTHER INFORMATION: Ala or absent and if present optionally
      amidated
<220> FEATURE:
<221> NAME/KEY: MISC_FEATURE
<222> LOCATION: (36)..(38)
<223> OTHER INFORMATION: Pro, homoproline, 3Hyp, 4Hyp, thioproline,
      N-alkylglycine, N-alkylpentylglycine, N-alkylalanine or absent
      and if present is optionally amidated

<400> SEQUENCE: 19

Xaa Xaa Xaa Gly Xaa Xaa Xaa Xaa Xaa Xaa Xaa Xaa Xaa Xaa Xaa
1               5                   10                  15

Xaa Ala Xaa Xaa Xaa Xaa Xaa Xaa Xaa Xaa Xaa Xaa Gly Gly Xaa Ser
            20                  25                  30

Ser Gly Ala Xaa Xaa Xaa
        35

<210> SEQ ID NO 20
<211> LENGTH: 39
<212> TYPE: PRT
<213> ORGANISM: Artificial Sequence
<220> FEATURE:
<223> OTHER INFORMATION: synthetic peptide construct
<220> FEATURE:
<221> NAME/KEY: MISC_FEATURE
<222> LOCATION: (1)..(1)
<223> OTHER INFORMATION: His, Arg, Tyr, Ala, Norval, Val Norleu or
      4-imidazopropionyl
<220> FEATURE:
<221> NAME/KEY: MISC_FEATURE
<222> LOCATION: (2)..(2)
<223> OTHER INFORMATION: Ser, Gly, Ala or Thr
<220> FEATURE:
<221> NAME/KEY: MISC_FEATURE
<222> LOCATION: (3)..(3)
<223> OTHER INFORMATION: Ala, Asp or Glu
<220> FEATURE:
<221> NAME/KEY: MISC_FEATURE
<222> LOCATION: (4)..(4)
<223> OTHER INFORMATION: Ala, Norval, Val, Norleu or Gly
<220> FEATURE:
<221> NAME/KEY: MISC_FEATURE
```

```
<222> LOCATION: (5)..(5)
<223> OTHER INFORMATION: Ala or Thr
<220> FEATURE:
<221> NAME/KEY: MISC_FEATURE
<222> LOCATION: (6)..(6)
<223> OTHER INFORMATION: Ala, Phe, Tyr or naphthylalanine
<220> FEATURE:
<221> NAME/KEY: MISC_FEATURE
<222> LOCATION: (7)..(7)
<223> OTHER INFORMATION: Thr or Ser
<220> FEATURE:
<221> NAME/KEY: MISC_FEATURE
<222> LOCATION: (8)..(8)
<223> OTHER INFORMATION: Ala, Ser or Thr
<220> FEATURE:
<221> NAME/KEY: MISC_FEATURE
<222> LOCATION: (9)..(9)
<223> OTHER INFORMATION: Ala, Norval, Val, Norleu, Asp or Glu
<220> FEATURE:
<221> NAME/KEY: MISC_FEATURE
<222> LOCATION: (10)..(10)
<223> OTHER INFORMATION: Ala, Leu, Ile, Val, pentylglycine or Met
<220> FEATURE:
<221> NAME/KEY: MISC_FEATURE
<222> LOCATION: (11)..(11)
<223> OTHER INFORMATION: Ala or Ser
<220> FEATURE:
<221> NAME/KEY: MISC_FEATURE
<222> LOCATION: (12)..(12)
<223> OTHER INFORMATION: Ala or Lys
<220> FEATURE:
<221> NAME/KEY: MISC_FEATURE
<222> LOCATION: (13)..(13)
<223> OTHER INFORMATION: Ala or Gln
<220> FEATURE:
<221> NAME/KEY: MISC_FEATURE
<222> LOCATION: (14)..(14)
<223> OTHER INFORMATION: Ala, Leu, Ile, pentylglycine, Val or Met
<220> FEATURE:
<221> NAME/KEY: MISC_FEATURE
<222> LOCATION: (15)..(17)
<223> OTHER INFORMATION: Ala or Glu
<220> FEATURE:
<221> NAME/KEY: MISC_FEATURE
<222> LOCATION: (19)..(19)
<223> OTHER INFORMATION: Ala or Val
<220> FEATURE:
<221> NAME/KEY: MISC_FEATURE
<222> LOCATION: (20)..(20)
<223> OTHER INFORMATION: Ala or Arg
<220> FEATURE:
<221> NAME/KEY: MISC_FEATURE
<222> LOCATION: (21)..(21)
<223> OTHER INFORMATION: Ala, Leu or Lys-NH-R where R is Lys, Arg,
      C1-10 straight chain or branched alkanoyl or cycloakylalkanoyl
<220> FEATURE:
<221> NAME/KEY: MISC_FEATURE
<222> LOCATION: (22)..(22)
<223> OTHER INFORMATION: Phe, Tyr or naphthylalanine
<220> FEATURE:
<221> NAME/KEY: MISC_FEATURE
<222> LOCATION: (23)..(23)
<223> OTHER INFORMATION: Ile, Val, Leu, pentylglycine, tert-butylglycine
      or Met
<220> FEATURE:
<221> NAME/KEY: MISC_FEATURE
<222> LOCATION: (24)..(24)
<223> OTHER INFORMATION: Ala, Glu or Asp
<220> FEATURE:
<221> NAME/KEY: MISC_FEATURE
<222> LOCATION: (25)..(25)
<223> OTHER INFORMATION: Ala, Trp, Phe, Tyr or naphthylalanine
<220> FEATURE:
<221> NAME/KEY: MISC_FEATURE
<222> LOCATION: (26)..(26)
<223> OTHER INFORMATION: Ala or Leu
<220> FEATURE:
<221> NAME/KEY: MISC_FEATURE
<222> LOCATION: (27)..(27)
<223> OTHER INFORMATION: Lys, Asn, Lys-NH-R or Ala where R is Lys, Arg,
```

```
        C1-10 straight chain or branched alkanoyl or cycloalkylalkanoyl
<220> FEATURE:
<221> NAME/KEY: MISC_FEATURE
<222> LOCATION: (28)..(28)
<223> OTHER INFORMATION: Lys, Asn, Lys-NH-R or Ala where R is Lys, Arg,
        C1-10 straight chain or branched alkanoyl or cycloalkylalkanoyl
        and is optionally amidated
<220> FEATURE:
<221> NAME/KEY: MISC_FEATURE
<222> LOCATION: (29)..(30)
<223> OTHER INFORMATION: Gly or absent and if present optionally
        amidated
<220> FEATURE:
<221> NAME/KEY: MISC_FEATURE
<222> LOCATION: (31)..(31)
<223> OTHER INFORMATION: Pro, homoproline, 3Hyp, 4Hyp, thiproline,
        N-alkylglycine, N-alkylpentylglycine, N-alkylalanine or absent
        and if present optionally amidated
<220> FEATURE:
<221> NAME/KEY: MISC_FEATURE
<222> LOCATION: (32)..(33)
<223> OTHER INFORMATION: Ser or absent and if present optionally
        amidated
<220> FEATURE:
<221> NAME/KEY: MISC_FEATURE
<222> LOCATION: (34)..(34)
<223> OTHER INFORMATION: Gly or absent and if present optionally
        amidated
<220> FEATURE:
<221> NAME/KEY: MISC_FEATURE
<222> LOCATION: (35)..(35)
<223> OTHER INFORMATION: Ala or absent and if present optionally
        amidated
<220> FEATURE:
<221> NAME/KEY: MISC_FEATURE
<222> LOCATION: (36)..(38)
<223> OTHER INFORMATION: Pro, homoproline, 3Hyp, 4Hyp, thiproline,
        N-alkylglycine, N-alkylpentylglycine, N-alkylalanine or absent
        and if present optionally amidated
<220> FEATURE:
<221> NAME/KEY: MISC_FEATURE
<222> LOCATION: (39)..(39)
<223> OTHER INFORMATION: Ser, Tyr or absent and if present optionally
        amidated

<400> SEQUENCE: 20

Xaa Xaa Xaa Xaa Xaa Xaa Xaa Xaa Xaa Xaa Xaa Xaa Xaa Xaa Xaa Xaa
1               5                   10                  15

Xaa Ala Xaa Xaa Xaa Xaa Xaa Xaa Xaa Xaa Xaa Xaa Gly Gly Xaa Ser
            20                  25                  30

Ser Gly Ala Xaa Xaa Xaa Xaa
        35

<210> SEQ ID NO 21
<211> LENGTH: 39
<212> TYPE: PRT
<213> ORGANISM: Artificial Sequence
<220> FEATURE:
<223> OTHER INFORMATION: synthetic peptide construct
<220> FEATURE:
<221> NAME/KEY: MISC_FEATURE
<222> LOCATION: (1)..(1)
<223> OTHER INFORMATION: His, Arg or Tyr
<220> FEATURE:
<221> NAME/KEY: MISC_FEATURE
<222> LOCATION: (2)..(2)
<223> OTHER INFORMATION: Ser, Gly, Ala or Thr
<220> FEATURE:
<221> NAME/KEY: MISC_FEATURE
<222> LOCATION: (3)..(3)
<223> OTHER INFORMATION: Asp or Glu
<220> FEATURE:
<221> NAME/KEY: MISC_FEATURE
<222> LOCATION: (6)..(6)
<223> OTHER INFORMATION: Phe, Tyr or naphthylalanine
<220> FEATURE:
```

```
<221> NAME/KEY: MISC_FEATURE
<222> LOCATION: (7)..(7)
<223> OTHER INFORMATION: Thr or Ser
<220> FEATURE:
<221> NAME/KEY: MISC_FEATURE
<222> LOCATION: (8)..(8)
<223> OTHER INFORMATION: Ser or Thr
<220> FEATURE:
<221> NAME/KEY: MISC_FEATURE
<222> LOCATION: (9)..(9)
<223> OTHER INFORMATION: Asp or Glu
<220> FEATURE:
<221> NAME/KEY: MISC_FEATURE
<222> LOCATION: (10)..(10)
<223> OTHER INFORMATION: Leu, Ile, Val, pentylglycine or Met
<220> FEATURE:
<221> NAME/KEY: MISC_FEATURE
<222> LOCATION: (14)..(14)
<223> OTHER INFORMATION: Leu, Ile, pentylglycine, Val or Met
<220> FEATURE:
<221> NAME/KEY: MISC_FEATURE
<222> LOCATION: (22)..(22)
<223> OTHER INFORMATION: Phe, Tyr or naphthylalanine
<220> FEATURE:
<221> NAME/KEY: MISC_FEATURE
<222> LOCATION: (23)..(23)
<223> OTHER INFORMATION: Ile, Val, Leu, pentylglycine, tert-butylglycine
      or Met
<220> FEATURE:
<221> NAME/KEY: MISC_FEATURE
<222> LOCATION: (24)..(24)
<223> OTHER INFORMATION: Glu or Asp
<220> FEATURE:
<221> NAME/KEY: MISC_FEATURE
<222> LOCATION: (25)..(25)
<223> OTHER INFORMATION: Trp, Phe, Tyr or naphthylalanine
<220> FEATURE:
<221> NAME/KEY: MISC_FEATURE
<222> LOCATION: (31)..(31)
<223> OTHER INFORMATION: Pro, homoproline, 3Hyp, 4Hyp, thioproline,
      N-alkylglycine, N-alkylpentylglycine or N-alkylalanine
<220> FEATURE:
<221> NAME/KEY: MISC_FEATURE
<222> LOCATION: (36)..(38)
<223> OTHER INFORMATION: Pro, homoproline, 3Hyp, 4Hyp, thioproline,
      N-alkylglycine, N-alkylpentylglycine or N-alkylalanine
<220> FEATURE:
<221> NAME/KEY: MISC_FEATURE
<222> LOCATION: (39)..(39)
<223> OTHER INFORMATION: Ser, Thr or Tyr and optionally amidated

<400> SEQUENCE: 21

Xaa Xaa Xaa Gly Thr Xaa Xaa Xaa Xaa Xaa Ser Lys Gln Xaa Glu Glu
1               5                   10                  15

Glu Ala Val Arg Leu Xaa Xaa Xaa Xaa Leu Lys Asn Gly Gly Xaa Ser
            20                  25                  30

Ser Gly Ala Xaa Xaa Xaa Xaa
        35

<210> SEQ ID NO 22
<211> LENGTH: 39
<212> TYPE: PRT
<213> ORGANISM: Artificial Sequence
<220> FEATURE:
<223> OTHER INFORMATION: synthetic peptide construct
<220> FEATURE:
<221> NAME/KEY: MISC_FEATURE
<222> LOCATION: (1)..(1)
<223> OTHER INFORMATION: His, Arg, Tyr, 4-imidazopropionyl
<220> FEATURE:
<221> NAME/KEY: MISC_FEATURE
<222> LOCATION: (2)..(2)
<223> OTHER INFORMATION: Ser, Gly, Ala or Thr
<220> FEATURE:
<221> NAME/KEY: MISC_FEATURE
<222> LOCATION: (3)..(3)
```

```
<223> OTHER INFORMATION: Asp or Glu
<220> FEATURE:
<221> NAME/KEY: MISC_FEATURE
<222> LOCATION: (6)..(6)
<223> OTHER INFORMATION: Phe, Tyr or naphthylalanine
<220> FEATURE:
<221> NAME/KEY: MISC_FEATURE
<222> LOCATION: (7)..(8)
<223> OTHER INFORMATION: Thr or Ser
<220> FEATURE:
<221> NAME/KEY: MISC_FEATURE
<222> LOCATION: (9)..(9)
<223> OTHER INFORMATION: Asp or Glu
<220> FEATURE:
<221> NAME/KEY: MISC_FEATURE
<222> LOCATION: (10)..(10)
<223> OTHER INFORMATION: Leu, Ile, Val, pentylglycine or Met
<220> FEATURE:
<221> NAME/KEY: MISC_FEATURE
<222> LOCATION: (14)..(14)
<223> OTHER INFORMATION: Leu, Ile, pentylglycine, Val or Met
<220> FEATURE:
<221> NAME/KEY: MISC_FEATURE
<222> LOCATION: (22)..(22)
<223> OTHER INFORMATION: Phe, Tyr or naphthylalanine
<220> FEATURE:
<221> NAME/KEY: MISC_FEATURE
<222> LOCATION: (23)..(23)
<223> OTHER INFORMATION: Ile, Val, Leu, pentylglycine, tert-butylglycine
      or Met
<220> FEATURE:
<221> NAME/KEY: MISC_FEATURE
<222> LOCATION: (24)..(24)
<223> OTHER INFORMATION: Glu or Asp
<220> FEATURE:
<221> NAME/KEY: MISC_FEATURE
<222> LOCATION: (25)..(25)
<223> OTHER INFORMATION: Trp, Phe, Tyr, or naphthylalanine
<220> FEATURE:
<221> NAME/KEY: MISC_FEATURE
<222> LOCATION: (27)..(28)
<223> OTHER INFORMATION: Lys, Asn or Lys-NH-R where R is Lys, Arg,
      C1-C10 straight chain or branched alkanoyl or cycloalkylalkanoyl
<220> FEATURE:
<221> NAME/KEY: MISC_FEATURE
<222> LOCATION: (31)..(31)
<223> OTHER INFORMATION: Pro, homoproline, 3Hyp, 4Hyp, thioproline,
      N-alkylglycine, N-alkylpentylglycine or N-alkylalanine
<220> FEATURE:
<221> NAME/KEY: MISC_FEATURE
<222> LOCATION: (36)..(38)
<223> OTHER INFORMATION: Pro, homoproline, 3Hyp, 4Hyp, thioproline,
      N-alkylglycine, N-alkylpentylglycine or N-alkylalanine
<220> FEATURE:
<221> NAME/KEY: MISC_FEATURE
<222> LOCATION: (39)..(39)
<223> OTHER INFORMATION: Ser, Thr or Tyr and is optionally amidated

<400> SEQUENCE: 22

Xaa Xaa Xaa Gly Thr Xaa Xaa Xaa Xaa Xaa Ser Lys Gln Xaa Glu Glu
1               5                   10                  15

Glu Ala Val Arg Leu Xaa Xaa Xaa Xaa Leu Xaa Xaa Gly Gly Xaa Ser
            20                  25                  30

Ser Gly Ala Xaa Xaa Xaa Xaa
        35

<210> SEQ ID NO 23
<211> LENGTH: 30
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (30)...(30)
<223> OTHER INFORMATION: AMIDATION
```

```
<400> SEQUENCE: 23

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly
            20                  25                  30

<210> SEQ ID NO 24
<211> LENGTH: 28
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (28)...(28)
<223> OTHER INFORMATION: AMIDATION

<400> SEQUENCE: 24

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn
            20                  25

<210> SEQ ID NO 25
<211> LENGTH: 28
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (28)...(28)
<223> OTHER INFORMATION: AMIDATION

<400> SEQUENCE: 25

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 26
<211> LENGTH: 28
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (28)...(28)
<223> OTHER INFORMATION: AMIDATION

<400> SEQUENCE: 26

His Ala Glu Gly Thr Phe Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 27
<211> LENGTH: 28
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (28)...(28)
<223> OTHER INFORMATION: AMIDATION
```

<400> SEQUENCE: 27

His Gly Glu Gly Ala Phe Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 28
<211> LENGTH: 28
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (28)...(28)
<223> OTHER INFORMATION: AMIDATION

<400> SEQUENCE: 28

His Gly Glu Gly Thr Ala Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 29
<211> LENGTH: 28
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (28)...(28)
<223> OTHER INFORMATION: AMIDATION

<400> SEQUENCE: 29

His Gly Glu Gly Thr Phe Thr Ala Asp Leu Ser Lys Gln Leu Glu Glu
1               5                   10                  15

Glu Ala Val Arg Leu Phe Ile Glu Phe Leu Lys Asn
            20                  25

<210> SEQ ID NO 30
<211> LENGTH: 28
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (28)...(28)
<223> OTHER INFORMATION: AMIDATION

<400> SEQUENCE: 30

His Gly Glu Gly Thr Phe Thr Ser Asp Ala Ser Lys Gln Leu Glu Glu
1               5                   10                  15

Glu Ala Val Arg Leu Phe Ile Glu Phe Leu Lys Asn
            20                  25

<210> SEQ ID NO 31
<211> LENGTH: 28
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (28)...(28)
<223> OTHER INFORMATION: AMIDATION

```
<400> SEQUENCE: 31

His Gly Glu Gly Thr Phe Thr Ser Asp Leu Ala Lys Gln Leu Glu Glu
1               5                   10                  15

Glu Ala Val Arg Leu Phe Ile Glu Phe Leu Lys Asn
            20                  25

<210> SEQ ID NO 32
<211> LENGTH: 28
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD-RES
<222> LOCATION: (28)...(28)
<223> OTHER INFORMATION: AMIDATION

<400> SEQUENCE: 32

His Gly Glu Gly Thr Phe Thr Ser Asp Leu Ser Ala Gln Leu Glu Glu
1               5                   10                  15

Glu Ala Val Arg Leu Phe Ile Glu Phe Leu Lys Asn
            20                  25

<210> SEQ ID NO 33
<211> LENGTH: 28
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (28)...(28)
<223> OTHER INFORMATION: AMIDATION

<400> SEQUENCE: 33

His Gly Glu Gly Thr Phe Thr Ser Asp Leu Ser Lys Ala Leu Glu Glu
1               5                   10                  15

Glu Ala Val Arg Leu Phe Ile Glu Phe Leu Lys Asn
            20                  25

<210> SEQ ID NO 34
<211> LENGTH: 28
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (28)...(28)
<223> OTHER INFORMATION: AMIDATION

<400> SEQUENCE: 34

His Gly Glu Gly Thr Phe Thr Ser Asp Leu Ser Lys Gln Ala Glu Glu
1               5                   10                  15

Glu Ala Val Arg Leu Phe Ile Glu Phe Leu Lys Asn
            20                  25

<210> SEQ ID NO 35
<211> LENGTH: 28
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (28)...(28)
<223> OTHER INFORMATION: AMIDATION
```

```
<400> SEQUENCE: 35

His Gly Glu Gly Thr Phe Thr Ser Asp Leu Ser Lys Gln Leu Ala Glu
1               5                   10                  15

Glu Ala Val Arg Leu Phe Ile Glu Phe Leu Lys Asn
            20                  25

<210> SEQ ID NO 36
<211> LENGTH: 28
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (28)...(28)
<223> OTHER INFORMATION: AMIDATION

<400> SEQUENCE: 36

His Gly Glu Gly Thr Phe Thr Ser Asp Leu Ser Lys Gln Leu Glu Ala
1               5                   10                  15

Glu Ala Val Arg Leu Phe Ile Glu Phe Leu Lys Asn
            20                  25

<210> SEQ ID NO 37
<211> LENGTH: 28
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (28)...(28)
<223> OTHER INFORMATION: AMIDATION

<400> SEQUENCE: 37

His Gly Glu Gly Thr Phe Thr Ser Asp Leu Ser Lys Gln Leu Glu Glu
1               5                   10                  15

Ala Ala Val Arg Leu Phe Ile Glu Phe Leu Lys Asn
            20                  25

<210> SEQ ID NO 38
<211> LENGTH: 28
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: AMIDATION
<222> LOCATION: (28)...(28)
<223> OTHER INFORMATION: amidated Asn (Asparaginamide)

<400> SEQUENCE: 38

His Gly Glu Gly Thr Phe Thr Ser Asp Leu Ser Lys Gln Leu Glu Glu
1               5                   10                  15

Glu Ala Ala Arg Leu Phe Ile Glu Phe Leu Lys Asn
            20                  25

<210> SEQ ID NO 39
<211> LENGTH: 28
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (28)...(28)
```

```
<223> OTHER INFORMATION: AMIDATION

<400> SEQUENCE: 39

His Gly Glu Gly Thr Phe Thr Ser Asp Leu Ser Lys Gln Leu Glu Glu
1               5                   10                  15

Glu Ala Val Ala Leu Phe Ile Glu Phe Leu Lys Asn
            20                  25

<210> SEQ ID NO 40
<211> LENGTH: 28
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (28)...(28)
<223> OTHER INFORMATION: AMIDATION

<400> SEQUENCE: 40

His Gly Glu Gly Thr Phe Thr Ser Asp Leu Ser Lys Gln Leu Glu Glu
1               5                   10                  15

Glu Ala Val Arg Ala Phe Ile Glu Phe Leu Lys Asn
            20                  25

<210> SEQ ID NO 41
<211> LENGTH: 28
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (28)...(28)
<223> OTHER INFORMATION: AMIDATION

<400> SEQUENCE: 41

His Gly Glu Gly Thr Phe Thr Ser Asp Leu Ser Lys Gln Leu Glu Glu
1               5                   10                  15

Glu Ala Val Arg Leu Phe Ile Ala Phe Leu Lys Asn
            20                  25

<210> SEQ ID NO 42
<211> LENGTH: 28
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (28)...(28)
<223> OTHER INFORMATION: AMIDATION

<400> SEQUENCE: 42

His Gly Glu Gly Thr Phe Thr Ser Asp Leu Ser Lys Gln Leu Glu Glu
1               5                   10                  15

Glu Ala Val Arg Leu Phe Ile Glu Ala Leu Lys Asn
            20                  25

<210> SEQ ID NO 43
<211> LENGTH: 28
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD-RES
<222> LOCATION: (28)...(28)
```

<223> OTHER INFORMATION: AMIDATION

<400> SEQUENCE: 43

His Gly Glu Gly Thr Phe Thr Ser Asp Leu Ser Lys Gln Leu Glu Glu
1               5                   10                  15

Glu Ala Val Arg Leu Phe Ile Glu Phe Ala Lys Asn
            20                  25

<210> SEQ ID NO 44
<211> LENGTH: 28
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (28)...(28)
<223> OTHER INFORMATION: AMIDATION

<400> SEQUENCE: 44

His Gly Glu Gly Thr Phe Thr Ser Asp Leu Ser Lys Gln Leu Glu Glu
1               5                   10                  15

Glu Ala Val Arg Leu Phe Ile Glu Phe Leu Ala Asn
            20                  25

<210> SEQ ID NO 45
<211> LENGTH: 28
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD-RES
<222> LOCATION: (28)...(28)
<223> OTHER INFORMATION: AMIDATION

<400> SEQUENCE: 45

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Ala
            20                  25

<210> SEQ ID NO 46
<211> LENGTH: 38
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (38)...(38)
<223> OTHER INFORMATION: AMIDATION

<400> SEQUENCE: 46

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro
    35

<210> SEQ ID NO 47
<211> LENGTH: 38
<212> TYPE: PRT
<213> ORGANISM: Artificial Sequence
<220> FEATURE:
<223> OTHER INFORMATION: synthetic peptide construct

```
<220> FEATURE:
<221> NAME/KEY: MOD_RES
<222> LOCATION: (38)...(38)
<223> OTHER INFORMATION: AMIDATION

<400> SEQUENCE: 47

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala Pro Pro Pro
        35

<210> SEQ ID NO 48
<211> LENGTH: 37
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (37)...(37)
<223> OTHER INFORMATION: AMIDATION

<400> SEQUENCE: 48

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro
        35

<210> SEQ ID NO 49
<211> LENGTH: 37
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (37)...(37)
<223> OTHER INFORMATION: AMIDATION

<400> SEQUENCE: 49

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala Pro Pro
        35

<210> SEQ ID NO 50
<211> LENGTH: 36
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (36)...(36)
<223> OTHER INFORMATION: AMIDATION

<400> SEQUENCE: 50

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
```

Ser Gly Ala Pro
        35

<210> SEQ ID NO 51
<211> LENGTH: 36
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (36)...(36)
<223> OTHER INFORMATION: AMIDATION

<400> SEQUENCE: 51

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala Pro
        35

<210> SEQ ID NO 52
<211> LENGTH: 35
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (35)...(35)
<223> OTHER INFORMATION: AMIDATION

<400> SEQUENCE: 52

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala
        35

<210> SEQ ID NO 53
<211> LENGTH: 35
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (35)...(35)
<223> OTHER INFORMATION: AMIDATION

<400> SEQUENCE: 53

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala
        35

<210> SEQ ID NO 54
<211> LENGTH: 34
<212> TYPE: PRT
<213> ORGANISM: Artificial Sequence
<220> FEATURE:

```
<223> OTHER INFORMATION: synthetic peptide construct
<220> FEATURE:
<221> NAME/KEY: MOD_RES
<222> LOCATION: (34)...(34)
<223> OTHER INFORMATION: AMIDATION

<400> SEQUENCE: 54

His Gly Glu Gly Thr Phe Thr Ser Asp Leu Ser Lys Gln Met Glu Glu
1               5                   10                  15
Glu Ala Val Arg Leu Phe Ile Glu Trp Leu Lys Asn Gly Gly Pro Ser
            20                  25                  30
Ser Gly

<210> SEQ ID NO 55
<211> LENGTH: 34
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (34)...(34)
<223> OTHER INFORMATION: AMIDATION

<400> SEQUENCE: 55

His Gly Glu Gly Thr Phe Thr Ser Asp Leu Ser Lys Gln Leu Glu Glu
1               5                   10                  15
Glu Ala Val Arg Leu Phe Ile Glu Phe Leu Lys Asn Gly Gly Pro Ser
            20                  25                  30
Ser Gly

<210> SEQ ID NO 56
<211> LENGTH: 33
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (33)...(33)
<223> OTHER INFORMATION: AMIDATION

<400> SEQUENCE: 56

His Gly Glu Gly Thr Phe Thr Ser Asp Leu Ser Lys Gln Met Glu Glu
1               5                   10                  15
Glu Ala Val Arg Leu Phe Ile Glu Trp Leu Lys Asn Gly Gly Pro Ser
            20                  25                  30
Ser

<210> SEQ ID NO 57
<211> LENGTH: 33
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (33)...(33)
<223> OTHER INFORMATION: AMIDATION

<400> SEQUENCE: 57

His Gly Glu Gly Thr Phe Thr Ser Asp Leu Ser Lys Gln Leu Glu Glu
1               5                   10                  15
Glu Ala Val Arg Leu Phe Ile Glu Phe Leu Lys Asn Gly Gly Pro Ser
            20                  25                  30
```

Ser

```
<210> SEQ ID NO 58
<211> LENGTH: 32
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (32)...(32)
<223> OTHER INFORMATION: AMIDATION

<400> SEQUENCE: 58
```

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

```
<210> SEQ ID NO 59
<211> LENGTH: 32
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (32)...(32)
<223> OTHER INFORMATION: AMIDATION

<400> SEQUENCE: 59
```

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

```
<210> SEQ ID NO 60
<211> LENGTH: 31
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (31)...(31)
<223> OTHER INFORMATION: AMIDATION

<400> SEQUENCE: 60
```

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro
            20                  25                  30

```
<210> SEQ ID NO 61
<211> LENGTH: 31
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (31)...(31)
<223> OTHER INFORMATION: AMIDATION

<400> SEQUENCE: 61
```

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro

<210> SEQ ID NO 62
<211> LENGTH: 30
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (30)...(30)
<223> OTHER INFORMATION: AMIDATION

<400> SEQUENCE: 62

His Gly Glu Gly Thr Phe Thr Ser Asp Leu Ser Lys Gln Leu Glu Glu
1               5                   10                  15
Glu Ala Val Arg Leu Phe Ile Glu Phe Leu Lys Asn Gly Gly
            20                  25                  30

<210> SEQ ID NO 63
<211> LENGTH: 29
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (29)...(29)
<223> OTHER INFORMATION: AMIDATION

<400> SEQUENCE: 63

His Gly Glu Gly Thr Phe Thr Ser Asp Leu Ser Lys Gln Met Glu Glu
1               5                   10                  15
Glu Ala Val Arg Leu Phe Ile Glu Trp Leu Lys Asn Gly
            20                  25

<210> SEQ ID NO 64
<211> LENGTH: 29
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (29)...(29)
<223> OTHER INFORMATION: AMIDATION

<400> SEQUENCE: 64

His Gly Glu Gly Thr Phe Thr Ser Asp Leu Ser Lys Gln Leu Glu Glu
1               5                   10                  15
Glu Ala Val Arg Leu Phe Ile Glu Phe Leu Lys Asn Gly
            20                  25

<210> SEQ ID NO 65
<211> LENGTH: 38
<212> TYPE: PRT
<213> ORGANISM: Artificial Sequence
<220> FEATURE:
<223> OTHER INFORMATION: synthetic peptide construct
<220> FEATURE:
<221> NAME/KEY: MISC_FEATURE
<222> LOCATION: (31)...(31)
<223> OTHER INFORMATION: thioproline
<220> FEATURE:
<221> NAME/KEY: MISC_FEATURE
<222> LOCATION: (36)...(38)
<223> OTHER INFORMATION: thioproline
<220> FEATURE:
<221> NAME/KEY: MOD_RES
<222> LOCATION: (38)...(38)

<223> OTHER INFORMATION: AMIDATION

<400> SEQUENCE: 65

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Xaa Ser
            20                  25                  30

Ser Gly Ala Xaa Xaa Xaa
        35

<210> SEQ ID NO 66
<211> LENGTH: 38
<212> TYPE: PRT
<213> ORGANISM: Artificial Sequence
<220> FEATURE:
<223> OTHER INFORMATION: synthetic peptide construct
<220> FEATURE:
<221> NAME/KEY: MISC_FEATURE
<222> LOCATION: (36)...(38)
<223> OTHER INFORMATION: thioproline
<220> FEATURE:
<221> NAME/KEY: MOD_RES
<222> LOCATION: (38)...(38)
<223> OTHER INFORMATION: AMIDATION

<400> SEQUENCE: 66

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Xaa Xaa Xaa
        35

<210> SEQ ID NO 67
<211> LENGTH: 37
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (31)...(31)
<223> OTHER INFORMATION: N-methyl ala.
<220> FEATURE:
<221> NAME/KEY: MOD_RES
<222> LOCATION: (37)...(37)
<223> OTHER INFORMATION: AMIDATION

<400> SEQUENCE: 67

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Ala Ser
            20                  25                  30

Ser Gly Ala Pro Pro
        35

<210> SEQ ID NO 68
<211> LENGTH: 37
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (31)...(31)
<223> OTHER INFORMATION: N-methyl ala
<220> FEATURE:
<221> NAME/KEY: MOD_RES

```
<222> LOCATION: (36)...(37)
<223> OTHER INFORMATION: N-methyl ala
<220> FEATURE:
<221> NAME/KEY: MOD_RES
<222> LOCATION: (37)...(37)
<223> OTHER INFORMATION: AMIDATION

<400> SEQUENCE: 68

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Ala Ser
            20                  25                  30

Ser Gly Ala Ala Ala
        35

<210> SEQ ID NO 69
<211> LENGTH: 37
<212> TYPE: PRT
<213> ORGANISM: Artificial Sequence
<220> FEATURE:
<223> OTHER INFORMATION: synthetic peptide construct
<220> FEATURE:
<221> NAME/KEY: MISC_FEATURE
<222> LOCATION: (31)...(31)
<223> OTHER INFORMATION: homoproline
<220> FEATURE:
<221> NAME/KEY: MISC_FEATURE
<222> LOCATION: (36)...(37)
<223> OTHER INFORMATION: homoproline
<220> FEATURE:
<221> NAME/KEY: MOD_RES
<222> LOCATION: (37)...(37)
<223> OTHER INFORMATION: AMIDATION

<400> SEQUENCE: 69

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Xaa Ser
            20                  25                  30

Ser Gly Ala Xaa Xaa
        35

<210> SEQ ID NO 70
<211> LENGTH: 36
<212> TYPE: PRT
<213> ORGANISM: Artificial Sequence
<220> FEATURE:
<223> OTHER INFORMATION: synthetic peptide construct
<220> FEATURE:
<221> NAME/KEY: MISC_FEATURE
<222> LOCATION: (31)...(31)
<223> OTHER INFORMATION: homoproline
<220> FEATURE:
<221> NAME/KEY: MISC_FEATURE
<222> LOCATION: (36)...(36)
<223> OTHER INFORMATION: homoproline.
<220> FEATURE:
<221> NAME/KEY: MOD_RES
<222> LOCATION: (36)...(36)
<223> OTHER INFORMATION: AMIDATION

<400> SEQUENCE: 70

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Xaa Ser
            20                  25                  30

Ser Gly Ala Xaa
        35
```

```
<210> SEQ ID NO 71
<211> LENGTH: 35
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (35)...(35)
<223> OTHER INFORMATION: AMIDATION

<400> SEQUENCE: 71

Arg Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala
        35

<210> SEQ ID NO 72
<211> LENGTH: 30
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (30)...(30)
<223> OTHER INFORMATION: AMIDATION

<400> SEQUENCE: 72

His Gly Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly
            20                  25                  30

<210> SEQ ID NO 73
<211> LENGTH: 28
<212> TYPE: PRT
<213> ORGANISM: Artificial Sequence
<220> FEATURE:
<223> OTHER INFORMATION: synthetic peptide construct
<220> FEATURE:
<221> NAME/KEY: MISC_FEATURE
<222> LOCATION: (6)...(6)
<223> OTHER INFORMATION: naphthylalanine
<220> FEATURE:
<221> NAME/KEY: MOD_RES
<222> LOCATION: (28)...(28)
<223> OTHER INFORMATION: AMIDATION

<400> SEQUENCE: 73

His Gly Glu Gly Thr Xaa Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 74
<211> LENGTH: 28
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (28)...(28)
<223> OTHER INFORMATION: AMIDATION

<400> SEQUENCE: 74
```

His Gly Glu Gly Thr Phe Ser Ser Asp Leu Ser Lys Gln Met Glu Glu
1               5                   10                  15

Glu Ala Val Arg Leu Phe Ile Glu Trp Leu Lys Asn
            20                  25

<210> SEQ ID NO 75
<211> LENGTH: 28
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (28)...(28)
<223> OTHER INFORMATION: AMIDATION

<400> SEQUENCE: 75

His Gly Glu Gly Thr Phe Ser Thr Asp Leu Ser Lys Gln Met Glu Glu
1               5                   10                  15

Glu Ala Val Arg Leu Phe Ile Glu Trp Leu Lys Asn
            20                  25

<210> SEQ ID NO 76
<211> LENGTH: 28
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (28)...(28)
<223> OTHER INFORMATION: AMIDATON

<400> SEQUENCE: 76

His Gly Glu Gly Thr Phe Thr Ser Glu Leu Ser Lys Gln Met Ala Glu
1               5                   10                  15

Glu Ala Val Arg Leu Phe Ile Glu Trp Leu Lys Asn
            20                  25

<210> SEQ ID NO 77
<211> LENGTH: 28
<212> TYPE: PRT
<213> ORGANISM: Artificial Sequence
<220> FEATURE:
<223> OTHER INFORMATION: synthetic peptide construct
<220> FEATURE:
<221> NAME/KEY: MISC_FEATURE
<222> LOCATION: (10)...(10)
<223> OTHER INFORMATION: pentylglycine
<220> FEATURE:
<221> NAME/KEY: MOD_RES
<222> LOCATION: (28)...(28)
<223> OTHER INFORMATION: AMIDATION

<400> SEQUENCE: 77

His Gly Glu Gly Thr Phe Thr Ser Asp Xaa Ser Lys Gln Leu Glu Glu
1               5                   10                  15

Glu Ala Val Arg Leu Phe Ile Glu Phe Leu Lys Asn
            20                  25

<210> SEQ ID NO 78
<211> LENGTH: 28
<212> TYPE: PRT
<213> ORGANISM: Artificial Sequence
<220> FEATURE:
<223> OTHER INFORMATION: synthetic peptide construct
<220> FEATURE:
<221> NAME/KEY: MISC_FEATURE

```
<222> LOCATION: (22)...(22)
<223> OTHER INFORMATION: naphthylalanine
<220> FEATURE:
<221> NAME/KEY: MOD_RES
<222> LOCATION: (28)...(28)
<223> OTHER INFORMATION: AMIDATION

<400> SEQUENCE: 78

His Gly Glu Gly Thr Phe Thr Ser Asp Leu Ser Lys Gln Leu Glu Glu
1               5                   10                  15

Glu Ala Val Arg Leu Xaa Ile Glu Phe Leu Lys Asn
            20                  25

<210> SEQ ID NO 79
<211> LENGTH: 28
<212> TYPE: PRT
<213> ORGANISM: Artificial Sequence
<220> FEATURE:
<223> OTHER INFORMATION: synthetic peptide construct
<220> FEATURE:
<221> NAME/KEY: MISC_FEATURE
<222> LOCATION: (23)...(23)
<223> OTHER INFORMATION: tert-butylglycine
<220> FEATURE:
<221> NAME/KEY: MOD_RES
<222> LOCATION: (28)...(28)
<223> OTHER INFORMATION: AMIDATION

<400> SEQUENCE: 79

His Gly Glu Gly Thr Phe Thr Ser Asp Leu Ser Lys Gln Met Glu Glu
1               5                   10                  15

Glu Ala Val Arg Leu Phe Xaa Glu Trp Leu Lys Asn
            20                  25

<210> SEQ ID NO 80
<211> LENGTH: 28
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (28)...(28)
<223> OTHER INFORMATION: AMIDATION

<400> SEQUENCE: 80

His Gly Glu Gly Thr Phe Thr Ser Asp Leu Ser Lys Gln Leu Glu Glu
1               5                   10                  15

Glu Ala Val Arg Leu Phe Ile Asp Phe Leu Lys Asn
            20                  25

<210> SEQ ID NO 81
<211> LENGTH: 33
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (33)...(33)
<223> OTHER INFORMATION: AMIDATION

<400> SEQUENCE: 81

His Gly Glu Gly Thr Phe Thr Ser Asp Ala Ser Lys Gln Leu Glu Glu
1               5                   10                  15

Glu Ala Val Arg Leu Phe Ile Glu Phe Leu Lys Asn Gly Gly Pro Ser
            20                  25                  30

Ser
```

<210> SEQ ID NO 82
<211> LENGTH: 29
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (29)...(29)
<223> OTHER INFORMATION: AMIDATON

<400> SEQUENCE: 82

His Gly Glu Gly Thr Phe Thr Ser Asp Ala Ser Lys Gln Met Glu Glu
1               5                   10                  15

Glu Ala Val Arg Leu Phe Ile Glu Trp Leu Lys Asn Gly
            20                  25

<210> SEQ ID NO 83
<211> LENGTH: 37
<212> TYPE: PRT
<213> ORGANISM: Artificial Sequence
<220> FEATURE:
<223> OTHER INFORMATION: artificially synthesized sequence of novel
      exendin agonist compound
<220> FEATURE:
<221> NAME/KEY: MISC_FEATURE
<222> LOCATION: (31)...(31)
<223> OTHER INFORMATION: homoproline
<220> FEATURE:
<221> NAME/KEY: MISC_FEATURE
<222> LOCATION: (36)...(37)
<223> OTHER INFORMATION: homoproline
<220> FEATURE:
<221> NAME/KEY: MOD_RES
<222> LOCATION: (37)...(37)
<223> OTHER INFORMATION: AMIDATION

<400> SEQUENCE: 83

His Gly Glu Gly Thr Phe Thr Ser Asp Ala Ser Lys Gln Met Glu Glu
1               5                   10                  15

Glu Ala Val Arg Leu Phe Ile Glu Trp Leu Lys Asn Gly Gly Xaa Ser
            20                  25                  30

Ser Gly Ala Xaa Xaa
        35

<210> SEQ ID NO 84
<211> LENGTH: 27
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (1)...(1)
<223> OTHER INFORMATION: 4-imidazolylpropionyl-Gly
<220> FEATURE:
<221> NAME/KEY: MOD_RES
<222> LOCATION: (26)...(26)
<223> OTHER INFORMATION: Lys-NH(epsilon)octanoyl.
<220> FEATURE:
<221> NAME/KEY: MOD_RES
<222> LOCATION: (27)...(27)
<223> OTHER INFORMATION: AMIDATION

<400> SEQUENCE: 84

Gly Glu Gly Thr Phe Thr Ser Asp Leu Ser Lys Gln Met Glu Glu Glu
1               5                   10                  15

Ala Val Arg Leu Phe Ile Glu Trp Leu Lys Asn
            20                  25

```
<210> SEQ ID NO 85
<211> LENGTH: 27
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (1)...(1)
<223> OTHER INFORMATION: 4-imidazolylpropionyl-Gly
<220> FEATURE:
<221> NAME/KEY: MOD_RES
<222> LOCATION: (26)...(26)
<223> OTHER INFORMATION: Lys-NH(epsilon)octanoyl.
<220> FEATURE:
<221> NAME/KEY: MOD_RES
<222> LOCATION: (27)...(27)
<223> OTHER INFORMATION: AMIDATION

<400> SEQUENCE: 85

Gly Glu Gly Thr Phe Thr Ser Asp Leu Ser Lys Gln Leu Glu Glu
1               5                   10                  15

Ala Val Arg Leu Phe Ile Glu Phe Leu Lys Asn
            20                  25

<210> SEQ ID NO 86
<211> LENGTH: 29
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (1)...(1)
<223> OTHER INFORMATION: 4-imidazolylpropionyl-Gly
<220> FEATURE:
<221> NAME/KEY: MOD_RES
<222> LOCATION: (26)...(26)
<223> OTHER INFORMATION: Lys-NH(epsilon)octanoyl.
<220> FEATURE:
<221> NAME/KEY: MOD_RES
<222> LOCATION: (29)...(29)
<223> OTHER INFORMATION: AMIDATION

<400> SEQUENCE: 86

Gly Glu Gly Thr Phe Thr Ser Asp Leu Ser Lys Gln Met Glu Glu
1               5                   10                  15

Ala Val Arg Leu Phe Ile Glu Trp Leu Lys Asn Gly Gly
            20                  25

<210> SEQ ID NO 87
<211> LENGTH: 29
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (1)...(1)
<223> OTHER INFORMATION: 4-imidazolylpropionyl-Gly
<220> FEATURE:
<221> NAME/KEY: MOD_RES
<222> LOCATION: (26)...(26)
<223> OTHER INFORMATION: Lys-NH(epsilon)octanoyl.
<220> FEATURE:
<221> NAME/KEY: MOD_RES
<222> LOCATION: (29)...(29)
<223> OTHER INFORMATION: AMIDATION

<400> SEQUENCE: 87

Gly Glu Gly Thr Phe Thr Ser Asp Leu Ser Lys Gln Leu Glu Glu Glu
```

```
                1               5                  10                  15
Ala Val Arg Leu Phe Ile Glu Phe Leu Lys Asn Gly Gly
            20                  25
```

<210> SEQ ID NO 88
<211> LENGTH: 27
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (1)...(1)
<223> OTHER INFORMATION: 4-imidazolylpropionyl-Gly
<220> FEATURE:
<221> NAME/KEY: MOD_RES
<222> LOCATION: (27)...(27)
<223> OTHER INFORMATION: Lys-NH(epsilon)octanoyl.
<220> FEATURE:
<221> NAME/KEY: MOD_RES
<222> LOCATION: (27)...(27)
<223> OTHER INFORMATION: AMIDATION

<400> SEQUENCE: 88

```
Gly Glu Gly Thr Phe Thr Ser Asp Leu Ser Lys Gln Met Glu Glu Glu
1               5                  10                  15
Ala Val Arg Leu Phe Ile Glu Trp Leu Asn Lys
            20                  25
```

<210> SEQ ID NO 89
<211> LENGTH: 27
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (1)...(1)
<223> OTHER INFORMATION: 4-imidazolylpropionyl-Gly
<220> FEATURE:
<221> NAME/KEY: MOD_RES
<222> LOCATION: (27)...(27)
<223> OTHER INFORMATION: Lys-NH(epsilon)octanoyl.
<220> FEATURE:
<221> NAME/KEY: MOD_RES
<222> LOCATION: (27)...(27)
<223> OTHER INFORMATION: AMIDATION

<400> SEQUENCE: 89

```
Gly Glu Gly Thr Phe Thr Ser Asp Leu Ser Lys Gln Leu Glu Glu Glu
1               5                  10                  15
Ala Val Arg Leu Phe Ile Glu Phe Leu Asn Lys
            20                  25
```

<210> SEQ ID NO 90
<211> LENGTH: 29
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (1)...(1)
<223> OTHER INFORMATION: 4-imidazolylpropionyl-Gly
<220> FEATURE:
<221> NAME/KEY: MOD_RES
<222> LOCATION: (27..(27)
<223> OTHER INFORMATION: Lys-NH(epsilon)octanoyl.
<220> FEATURE:
<221> NAME/KEY: MOD_RES
<222> LOCATION: (29)...(29)
<223> OTHER INFORMATION: AMIDTION

```
<400> SEQUENCE: 90

Gly Glu Gly Thr Phe Thr Ser Asp Leu Ser Lys Gln Met Glu Glu
1               5                   10                  15

Ala Val Arg Leu Phe Ile Glu Trp Leu Asn Lys Gly Gly
            20                  25

<210> SEQ ID NO 91
<211> LENGTH: 29
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD-RES
<222> LOCATION: (1)...(1)
<223> OTHER INFORMATION: 4-imidazolylpropionyl-Gly
<220> FEATURE:
<221> NAME/KEY: MOD_RES
<222> LOCATION: (27)...(27)
<223> OTHER INFORMATION: Lys-NH(epsilon)octanoyl.
<220> FEATURE:
<221> NAME/KEY: MOD_RES
<222> LOCATION: (29)...(29)
<223> OTHER INFORMATION: AMIDATION

<400> SEQUENCE: 91

Gly Glu Gly Thr Phe Thr Ser Asp Leu Ser Lys Gln Leu Glu Glu
1               5                   10                  15

Ala Val Arg Leu Phe Ile Glu Phe Leu Asn Lys Gly Gly
            20                  25

<210> SEQ ID NO 92
<211> LENGTH: 27
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (27)...(27)
<223> OTHER INFORMATION: AMIDATION
<220> FEATURE:
<221> NAME/KEY: MOD_RES
<222> LOCATION: (1)...(1)
<223> OTHER INFORMATION: 4-imidazolylpropionyl-Gly
<220> FEATURE:
<221> NAME/KEY: MOD_RES
<222> LOCATION: (26)...(26)
<223> OTHER INFORMATION: Lys-NH(epsilon)octanoyl

<400> SEQUENCE: 92

Xaa Glu Gly Thr Phe Thr Ser Ala Leu Ser Lys Gln Met Glu Glu
1               5                   10                  15

Ala Val Arg Leu Phe Ile Glu Trp Leu Xaa Asn
            20                  25

<210> SEQ ID NO 93
<211> LENGTH: 27
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (27)...(27)
<223> OTHER INFORMATION: AMIDATION
<220> FEATURE:
<221> NAME/KEY: MOD_RES
<222> LOCATION: (1)...(1)
<223> OTHER INFORMATION: 4-imidazolylpropionyl-Gly
```

```
<220> FEATURE:
<221> NAME/KEY: MOD_RES
<222> LOCATION: (26)...(26)
<223> OTHER INFORMATION: Lys-NH(epsilon)octanoyl

<400> SEQUENCE: 93

Xaa Glu Gly Thr Phe Thr Ser Ala Leu Ser Lys Gln Leu Glu Glu Glu
1               5                   10                  15

Ala Val Arg Leu Phe Ile Glu Phe Leu Xaa Asn
            20                  25

<210> SEQ ID NO 94
<211> LENGTH: 29
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (29)...(29)
<223> OTHER INFORMATION: AMIDATION
<220> FEATURE:
<221> NAME/KEY: MOD_RES
<222> LOCATION: (1)...(1)
<223> OTHER INFORMATION: 4-imidazolylpropionyl-Gly
<220> FEATURE:
<221> NAME/KEY: MOD_RES
<222> LOCATION: (26),,,(26)
<223> OTHER INFORMATION: Lys-NH(epsilon)octanoyl

<400> SEQUENCE: 94

Xaa Glu Gly Thr Phe Thr Ser Ala Leu Ser Lys Gln Met Glu Glu Glu
1               5                   10                  15

Ala Val Arg Leu Phe Ile Glu Trp Leu Xaa Asn Gly Gly
            20                  25

<210> SEQ ID NO 95
<211> LENGTH: 29
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (29)...(29)
<223> OTHER INFORMATION: AMIDATION
<220> FEATURE:
<221> NAME/KEY: MOD_RES
<222> LOCATION: (1)...(1)
<223> OTHER INFORMATION: 4-imidazolylpropionyl-Gly
<220> FEATURE:
<221> NAME/KEY: MOD_RES
<222> LOCATION: (26)...(26)
<223> OTHER INFORMATION: Lys-NH(epsilon)octanoyl

<400> SEQUENCE: 95

Xaa Glu Gly Thr Phe Thr Ser Ala Leu Ser Lys Gln Leu Glu Glu Glu
1               5                   10                  15

Ala Val Arg Leu Phe Ile Glu Phe Leu Xaa Asn Gly Gly
            20                  25

<210> SEQ ID NO 96
<211> LENGTH: 27
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (27)...(27)
<223> OTHER INFORMATION: AMIDATION
```

```
<220> FEATURE:
<221> NAME/KEY: MOD_RES
<222> LOCATION: (1)...(1)
<223> OTHER INFORMATION: 4-imidazolylpropionyl-Gly
<220> FEATURE:
<221> NAME/KEY: MOD_RES
<222> LOCATION: (27)...(27)
<223> OTHER INFORMATION: Lys-NH(epsilon)octanoyl

<400> SEQUENCE: 96

Xaa Glu Gly Thr Phe Thr Ser Ala Leu Ser Lys Gln Met Glu Glu Glu
1               5                   10                  15

Ala Val Arg Leu Phe Ile Glu Trp Leu Asn Xaa
            20                  25

<210> SEQ ID NO 97
<211> LENGTH: 27
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (27)...(27)
<223> OTHER INFORMATION: AMIDATION
<220> FEATURE:
<221> NAME/KEY: MOD_RES
<222> LOCATION: (1)...(1)
<223> OTHER INFORMATION: 4-imidazolylpropionyl-Gly
<220> FEATURE:
<221> NAME/KEY: MOD_RES
<222> LOCATION: (27)...(27)
<223> OTHER INFORMATION: Lys-NH(epsilon)octanoyl

<400> SEQUENCE: 97

Xaa Glu Gly Thr Phe Thr Ser Ala Leu Ser Lys Gln Leu Glu Glu Glu
1               5                   10                  15

Ala Val Arg Leu Phe Ile Glu Phe Leu Asn Xaa
            20                  25

<210> SEQ ID NO 98
<211> LENGTH: 29
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (29)...(29)
<223> OTHER INFORMATION: AMIDATION
<220> FEATURE:
<221> NAME/KEY: MOD_RES
<222> LOCATION: (1)...(1)
<223> OTHER INFORMATION: 4-imidazolylpropionyl-Gly
<220> FEATURE:
<221> NAME/KEY: MOD_RES
<222> LOCATION: (27)...(27)
<223> OTHER INFORMATION: Lys-NH(epsilon)octanoyl

<400> SEQUENCE: 98

Xaa Glu Gly Thr Phe Thr Ser Ala Leu Ser Lys Gln Met Glu Glu Glu
1               5                   10                  15

Ala Val Arg Leu Phe Ile Glu Trp Leu Asn Xaa Gly Gly
            20                  25

<210> SEQ ID NO 99
<211> LENGTH: 29
<212> TYPE: PRT
<213> ORGANISM: Artificial Sequence
<220> FEATURE:
<223> OTHER INFORMATION: synthetic peptide construct
```

```
<220> FEATURE:
<221> NAME/KEY: MOD_RES
<222> LOCATION: (29)...(29)
<223> OTHER INFORMATION: AMIDATION
<220> FEATURE:
<221> NAME/KEY: MOD_RES
<222> LOCATION: (1),,,(1)
<223> OTHER INFORMATION: 4-imidazolylpropionyl-Gly
<220> FEATURE:
<221> NAME/KEY: MOD_RES
<222> LOCATION: (27),,,(27)
<223> OTHER INFORMATION: Lys-NH(epsilon)octanoyl

<400> SEQUENCE: 99

Xaa Glu Gly Thr Phe Thr Ser Ala Leu Ser Lys Gln Leu Glu Glu
1               5                   10                  15

Ala Val Arg Leu Phe Ile Glu Phe Leu Asn Xaa Gly Gly
            20                  25

<210> SEQ ID NO 100
<211> LENGTH: 28
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (28)...(28)
<223> OTHER INFORMATION: AMIDATION
<220> FEATURE:
<221> NAME/KEY: MOD_RES
<222> LOCATION: (27)...(27)
<223> OTHER INFORMATION: Lys-NH(epsilon)octanoyl

<400> SEQUENCE: 100

Ala Gly Glu Gly Thr Phe Thr Ser Asp Leu Ser Lys Gln Met Glu Glu
1               5                   10                  15

Glu Ala Val Arg Leu Phe Ile Glu Trp Leu Xaa Asn
            20                  25

<210> SEQ ID NO 101
<211> LENGTH: 28
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (28)...(28)
<223> OTHER INFORMATION: AMIDATION
<220> FEATURE:
<221> NAME/KEY: MOD_RES
<222> LOCATION: (27)...(27)
<223> OTHER INFORMATION: Lys-NH(epsilon)octanoyl

<400> SEQUENCE: 101

Ala Gly Glu Gly Thr Phe Thr Ser Asp Leu Ser Lys Gln Leu Glu Glu
1               5                   10                  15

Glu Ala Val Arg Leu Phe Ile Glu Phe Leu Xaa Asn
            20                  25

<210> SEQ ID NO 102
<211> LENGTH: 30
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (30)...(30)
<223> OTHER INFORMATION: AMIDATION
```

```
<220> FEATURE:
<221> NAME/KEY: MOD_RES
<222> LOCATION: (27)...(27)
<223> OTHER INFORMATION: Lys-NH(epsilon)octanoyl

<400> SEQUENCE: 102

Ala Gly Glu Gly Thr Phe Thr Ser Asp Leu Ser Lys Gln Met Glu Glu
1               5                   10                  15

Glu Ala Val Arg Leu Phe Ile Glu Trp Leu Xaa Asn Gly Gly
            20                  25                  30

<210> SEQ ID NO 103
<211> LENGTH: 30
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (30)...(30)
<223> OTHER INFORMATION: AMIDATION
<220> FEATURE:
<221> NAME/KEY: MOD_RES
<222> LOCATION: (27)...(27)
<223> OTHER INFORMATION: Lys-NH(epsilon)octanoyl

<400> SEQUENCE: 103

Ala Gly Glu Gly Thr Phe Thr Ser Asp Leu Ser Lys Gln Leu Glu Glu
1               5                   10                  15

Glu Ala Val Arg Leu Phe Ile Glu Phe Leu Xaa Asn Gly Gly
            20                  25                  30

<210> SEQ ID NO 104
<211> LENGTH: 28
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (28)...(28)
<223> OTHER INFORMATION: AMIDATION
<220> FEATURE:
<221> NAME/KEY: MOD_RES
<222> LOCATION: (27)...(27)
<223> OTHER INFORMATION: Lys-NH(epsilon)octanoyl

<400> SEQUENCE: 104

Ala Gly Glu Gly Thr Phe Thr Ser Asp Leu Ser Lys Gln Met Glu Glu
1               5                   10                  15

Glu Ala Val Arg Leu Phe Ile Glu Trp Leu Asn Xaa
            20                  25

<210> SEQ ID NO 105
<211> LENGTH: 28
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (28)...(28)
<223> OTHER INFORMATION: AMIDATION
<220> FEATURE:
<221> NAME/KEY: MOD_RES
<222> LOCATION: (27)...(27)
<223> OTHER INFORMATION: Lys-NH(epsilon)octanoyl

<400> SEQUENCE: 105

Ala Gly Glu Gly Thr Phe Thr Ser Asp Leu Ser Lys Gln Leu Glu Glu
```

```
1               5                   10                  15
Glu Ala Val Arg Leu Phe Ile Glu Phe Leu Asn Xaa
            20                  25
```

<210> SEQ ID NO 106
<211> LENGTH: 30
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (30)...(30)
<223> OTHER INFORMATION: AMIDATION
<220> FEATURE:
<221> NAME/KEY: MOD_RES
<222> LOCATION: (28)...(28)
<223> OTHER INFORMATION: Lys-NH(epsilon)octanoyl

<400> SEQUENCE: 106

```
Ala Gly Glu Gly Thr Phe Thr Ser Asp Leu Ser Lys Gln Met Glu Glu
1               5                   10                  15

Glu Ala Val Arg Leu Phe Ile Glu Trp Leu Asn Xaa Gly Gly
            20                  25                  30
```

<210> SEQ ID NO 107
<211> LENGTH: 30
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (30)...(30)
<223> OTHER INFORMATION: AMIDATION
<220> FEATURE:
<221> NAME/KEY: MOD_RES
<222> LOCATION: (28)...(28)
<223> OTHER INFORMATION: Lys-NH(epsilon)octanoyl

<400> SEQUENCE: 107

```
Ala Gly Glu Gly Thr Phe Thr Ser Asp Leu Ser Lys Gln Leu Glu Glu
1               5                   10                  15

Glu Ala Val Arg Leu Phe Ile Glu Phe Leu Asn Xaa Gly Gly
            20                  25                  30
```

<210> SEQ ID NO 108
<211> LENGTH: 39
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD-RES
<222> LOCATION: (39)...(39)
<223> OTHER INFORMATION: AMIDATION

<400> SEQUENCE: 108

```
His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala Pro Pro Ser
        35
```

<210> SEQ ID NO 109
<211> LENGTH: 39
<212> TYPE: PRT

```
<213> ORGANISM: Artificial Sequence
<220> FEATURE:
<223> OTHER INFORMATION: synthetic peptide construct
<220> FEATURE:
<221> NAME/KEY: MOD-RES
<222> LOCATION: (39)...(39)
<223> OTHER INFORMATION: AMIDATION

<400> SEQUENCE: 109

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 110
<211> LENGTH: 39
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD-RES
<222> LOCATION: (39)...(39)
<223> OTHER INFORMATION: AMIDATION

<400> SEQUENCE: 110

His Gly Glu Gly Thr Phe Thr Ser Asp Leu Ser Lys Gln Met Glu Glu
1               5                   10                  15

Glu Ala Val Arg Leu Phe Ile Glu Phe Leu Lys Asn Gly Gly Pro Ser
            20                  25                  30

Ser Gly Ala Pro Pro Pro Ser
        35

<210> SEQ ID NO 111
<211> LENGTH: 39
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD-RES
<222> LOCATION: (39)...(39)
<223> OTHER INFORMATION: AMIDATION

<400> SEQUENCE: 111

Tyr Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 112
<211> LENGTH: 39
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD-RES
<222> LOCATION: (39)...(39)
<223> OTHER INFORMATION: AMIDATION

<400> SEQUENCE: 112

His Gly Glu Gly Thr Phe Thr Ser Asp Leu Ser Lys Gln Met Glu Glu
```

```
1               5                   10                  15
Glu Ala Val Arg Leu Phe Ile Glu Trp Leu Lys Asn Gly Gly Pro Ser
                20                  25                  30

Ser Gly Ala Pro Pro Tyr
        35

<210> SEQ ID NO 113
<211> LENGTH: 39
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD-RES
<222> LOCATION: (39)...(39)
<223> OTHER INFORMATION: AMIDATION

<400> SEQUENCE: 113

His Gly Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Ser
        35

<210> SEQ ID NO 114
<211> LENGTH: 39
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (6)...(6)
<223> OTHER INFORMATION: napthylalanine
<220> FEATURE:
<221> NAME/KEY: MOD-RES
<222> LOCATION: (39)...(39)
<223> OTHER INFORMATION: AMIDATION

<400> SEQUENCE: 114

His Gly Glu Gly Thr Xaa Thr Ser Asp Leu Ser Lys Gln Met Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Ser
        35

<210> SEQ ID NO 115
<211> LENGTH: 39
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD-RES
<222> LOCATION: (39)...(39)
<223> OTHER INFORMATION: AMIDATION

<400> SEQUENCE: 115

His Gly Glu Gly Thr Phe Ser Ser Asp Leu Ser Lys Gln Met Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Ser
        35
```

<210> SEQ ID NO 116
<211> LENGTH: 39
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD-RES
<222> LOCATION: (39)...(39)
<223> OTHER INFORMATION: AMIDATION

<400> SEQUENCE: 116

His Gly Glu Gly Thr Phe Ser Thr Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 117
<211> LENGTH: 39
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD-RES
<222> LOCATION: (39)...(39)
<223> OTHER INFORMATION: AMIDATION

<400> SEQUENCE: 117

His Gly Glu Gly Thr Phe Thr Thr Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 118
<211> LENGTH: 39
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD-RES
<222> LOCATION: (39)...(39)
<223> OTHER INFORMATION: AMIDATION

<400> SEQUENCE: 118

His Gly Glu Gly Thr Phe Thr Ser Glu Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 119
<211> LENGTH: 39
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (10)...(10)

```
<223> OTHER INFORMATION: pentylglycine
<220> FEATURE:
<221> NAME/KEY: MOD-RES
<222> LOCATION: (39)...(39)
<223> OTHER INFORMATION: AMIDATION

<400> SEQUENCE: 119

His Gly Glu Gly Thr Phe Thr Ser Asp Xaa Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 120
<211> LENGTH: 39
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (10)...(10)
<223> OTHER INFORMATION: pentylglycine
<220> FEATURE:
<221> NAME/KEY: MOD-RES
<222> LOCATION: (39)...(39)
<223> OTHER INFORMATION: AMIDATION

<400> SEQUENCE: 120

His Gly Glu Gly Thr Phe Thr Ser Asp Xaa Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala Pro Pro Pro Ser
        35

<210> SEQ ID NO 121
<211> LENGTH: 39
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (14)...(14)
<223> OTHER INFORMATION: pentylglycine
<220> FEATURE:
<221> NAME/KEY: MOD-RES
<222> LOCATION: (39)...(39)
<223> OTHER INFORMATION: AMIDATION

<400> SEQUENCE: 121

His Gly Glu Gly Thr Phe Thr Ser Asp Leu Ser Lys Gln Xaa Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 122
<211> LENGTH: 39
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD-RES
```

```
<222> LOCATION: (39)...(39)
<223> OTHER INFORMATION: AMIDATION
<220> FEATURE:
<221> NAME/KEY: MOD_RES
<222> LOCATION: (14)...(14)
<223> OTHER INFORMATION: pentylglycine

<400> SEQUENCE: 122

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala Pro Pro Pro Ser
        35

<210> SEQ ID NO 123
<211> LENGTH: 39
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (22)..(22)
<223> OTHER INFORMATION: napthylalanine
<220> FEATURE:
<221> NAME/KEY: MOD-RES
<222> LOCATION: (39)...(39)
<223> OTHER INFORMATION: AMIDATION

<400> SEQUENCE: 123

His Gly Glu Gly Thr Phe Thr Ser Asp Leu Ser Lys Gln Met Glu Glu
1               5                   10                  15

Glu Ala Val Arg Leu Xaa Ile Glu Trp Leu Lys Asn Gly Gly Pro Ser
            20                  25                  30

Ser Gly Ala Pro Pro Pro Ser
        35

<210> SEQ ID NO 124
<211> LENGTH: 39
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD-RES
<222> LOCATION: (39)...(39)
<223> OTHER INFORMATION: AMIDATION

<400> SEQUENCE: 124

His Gly Glu Gly Thr Phe Thr Ser Asp Leu Ser Lys Gln Met Glu Glu
1               5                   10                  15

Glu Ala Val Arg Leu Phe Val Glu Trp Leu Lys Asn Gly Gly Pro Ser
            20                  25                  30

Ser Gly Ala Pro Pro Pro Ser
        35

<210> SEQ ID NO 125
<211> LENGTH: 39
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD-RES
<222> LOCATION: (39)...(39)
<223> OTHER INFORMATION: AMIDATION
```

```
<400> SEQUENCE: 125

His Gly Glu Gly Thr Phe Thr Ser Asp Leu Ser Lys Gln Leu Glu Glu
1               5                   10                  15

Glu Ala Val Arg Leu Phe Val Glu Phe Leu Lys Asn Gly Gly Pro Ser
            20                  25                  30

Ser Gly Ala Pro Pro Pro Ser
        35

<210> SEQ ID NO 126
<211> LENGTH: 39
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (23)...(23)
<223> OTHER INFORMATION: tert-butylglycine
<220> FEATURE:
<221> NAME/KEY: MOD-RES
<222> LOCATION: (39)...(39)
<223> OTHER INFORMATION: AMIDATION

<400> SEQUENCE: 126

His Gly Glu Gly Thr Phe Thr Ser Asp Leu Ser Lys Gln Met Glu Glu
1               5                   10                  15

Glu Ala Val Arg Leu Phe Xaa Glu Trp Leu Lys Asn Gly Gly Pro Ser
            20                  25                  30

Ser Gly Ala Pro Pro Pro Ser
        35

<210> SEQ ID NO 127
<211> LENGTH: 39
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (23)...(23)
<223> OTHER INFORMATION: tert-butylglycine
<220> FEATURE:
<221> NAME/KEY: MOD-RES
<222> LOCATION: (39)...(39)
<223> OTHER INFORMATION: AMIDATION

<400> SEQUENCE: 127

His Gly Glu Gly Thr Phe Thr Ser Asp Leu Ser Lys Gln Leu Glu Glu
1               5                   10                  15

Glu Ala Val Arg Leu Phe Xaa Glu Phe Leu Lys Asn Gly Gly Pro Ser
            20                  25                  30

Ser Gly Ala Pro Pro Pro Ser
        35

<210> SEQ ID NO 128
<211> LENGTH: 39
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD-RES
<222> LOCATION: (39)...(39)
<223> OTHER INFORMATION: AMIDATION

<400> SEQUENCE: 128

His Gly Glu Gly Thr Phe Thr Ser Asp Leu Ser Lys Gln Met Glu Glu
```

-continued

```
                1               5                  10                  15
Glu Ala Val Arg Leu Phe Ile Asp Trp Leu Lys Asn Gly Gly Pro Ser
                20                  25                  30

Ser Gly Ala Pro Pro Pro Ser
        35

<210> SEQ ID NO 129
<211> LENGTH: 39
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD-RES
<222> LOCATION: (39)...(39)
<223> OTHER INFORMATION: AMIDATION

<400> SEQUENCE: 129

His Gly Glu Gly Thr Phe Thr Ser Asp Leu Ser Lys Gln Met Glu Glu
1               5                  10                  15

Glu Ala Val Arg Leu Phe Ile Glu Phe Leu Lys Asn Gly Gly Pro Ser
                20                  25                  30

Ser Gly Ala Pro Pro Pro Ser
        35

<210> SEQ ID NO 130
<211> LENGTH: 39
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (31)...(31)
<223> OTHER INFORMATION: thioproline
<220> FEATURE:
<221> NAME/KEY: MOD_RES
<222> LOCATION: (36)..(38)
<223> OTHER INFORMATION: thioproline
<220> FEATURE:
<221> NAME/KEY: MOD-RES
<222> LOCATION: (39)...(39)
<223> OTHER INFORMATION: AMIDATION

<400> SEQUENCE: 130

His Gly Glu Gly Thr Phe Thr Ser Asp Leu Ser Lys Gln Met Glu Glu
1               5                  10                  15

Glu Ala Val Arg Leu Phe Ile Glu Trp Leu Lys Asn Gly Gly Xaa Ser
                20                  25                  30

Ser Gly Ala Xaa Xaa Xaa Ser
        35

<210> SEQ ID NO 131
<211> LENGTH: 39
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (36)..(38)
<223> OTHER INFORMATION: thioproline
<220> FEATURE:
<221> NAME/KEY: MOD-RES
<222> LOCATION: (39)...(39)
<223> OTHER INFORMATION: AMIDATION

<400> SEQUENCE: 131
```

```
His Gly Glu Gly Thr Phe Thr Ser Asp Leu Ser Lys Gln Met Glu
1               5                   10                  15

Glu Ala Val Arg Leu Phe Ile Glu Trp Leu Lys Asn Gly Gly Pro Ser
                20                  25                  30

Ser Gly Ala Xaa Xaa Xaa Ser
            35

<210> SEQ ID NO 132
<211> LENGTH: 39
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (31)...(31)
<223> OTHER INFORMATION: homoproline
<220> FEATURE:
<221> NAME/KEY: MOD_RES
<222> LOCATION: (36)..(38)
<223> OTHER INFORMATION: homoproline
<220> FEATURE:
<221> NAME/KEY: MOD-RES
<222> LOCATION: (39)...(39)
<223> OTHER INFORMATION: AMIDATION

<400> SEQUENCE: 132

His Gly Glu Gly Thr Phe Thr Ser Asp Leu Ser Lys Gln Met Glu
1               5                   10                  15

Glu Ala Val Arg Leu Phe Ile Glu Trp Leu Lys Asn Gly Gly Xaa Ser
                20                  25                  30

Ser Gly Ala Xaa Xaa Xaa Ser
            35

<210> SEQ ID NO 133
<211> LENGTH: 39
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (36)..(38)
<223> OTHER INFORMATION: homoproline
<220> FEATURE:
<221> NAME/KEY: MOD-RES
<222> LOCATION: (39)...(39)
<223> OTHER INFORMATION: AMIDATION

<400> SEQUENCE: 133

His Gly Glu Gly Thr Phe Thr Ser Asp Leu Ser Lys Gln Met Glu
1               5                   10                  15

Glu Ala Val Arg Leu Phe Ile Glu Trp Leu Lys Asn Gly Gly Pro Ser
                20                  25                  30

Ser Gly Ala Xaa Xaa Xaa Ser
            35

<210> SEQ ID NO 134
<211> LENGTH: 39
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (31)...(31)
<223> OTHER INFORMATION: thioproline
<220> FEATURE:
<221> NAME/KEY: MOD_RES
```

```
<222> LOCATION: (36)..(38)
<223> OTHER INFORMATION: thioproline
<220> FEATURE:
<221> NAME/KEY: MOD-RES
<222> LOCATION: (39)...(39)
<223> OTHER INFORMATION: AMIDATION

<400> SEQUENCE: 134

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Xaa Ser
            20                  25                  30

Ser Gly Ala Xaa Xaa Xaa Ser
        35

<210> SEQ ID NO 135
<211> LENGTH: 39
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (31)...(31)
<223> OTHER INFORMATION: homoproline
<220> FEATURE:
<221> NAME/KEY: MOD_RES
<222> LOCATION: (36)..(38)
<223> OTHER INFORMATION: homoproline
<220> FEATURE:
<221> NAME/KEY: MOD-RES
<222> LOCATION: (39)...(39)
<223> OTHER INFORMATION: AMIDATION

<400> SEQUENCE: 135

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Xaa Ser
            20                  25                  30

Ser Gly Ala Xaa Xaa Xaa Ser
        35

<210> SEQ ID NO 136
<211> LENGTH: 39
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (31)...(31)
<223> OTHER INFORMATION: N-methylalanine
<220> FEATURE:
<221> NAME/KEY: MOD_RES
<222> LOCATION: (36)..(38)
<223> OTHER INFORMATION: N-methylalanine
<220> FEATURE:
<221> NAME/KEY: MOD_RES
<222> LOCATION: (39)...(39)
<223> OTHER INFORMATION: AMIDATION

<400> SEQUENCE: 136

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Xaa Ser
            20                  25                  30

Ser Gly Ala Xaa Xaa Xaa Ser
        35
```

<210> SEQ ID NO 137
<211> LENGTH: 39
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (36)..(38)
<223> OTHER INFORMATION: N-methylalanine
<220> FEATURE:
<221> NAME/KEY: MOD-RES
<222> LOCATION: (39)...(39)
<223> OTHER INFORMATION: AMIDATION

<400> SEQUENCE: 137

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Xaa Xaa Xaa Ser
        35

<210> SEQ ID NO 138
<211> LENGTH: 39
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (31)...(31)
<223> OTHER INFORMATION: N-methylalanine
<220> FEATURE:
<221> NAME/KEY: MOD_RES
<222> LOCATION: (36)..(38)
<223> OTHER INFORMATION: N-methylalanine
<220> FEATURE:
<221> NAME/KEY: MOD-RES
<222> LOCATION: (39)...(39)
<223> OTHER INFORMATION: AMIDATION

<400> SEQUENCE: 138

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Xaa Ser
            20                  25                  30

Ser Gly Ala Xaa Xaa Xaa Ser
        35

<210> SEQ ID NO 139
<211> LENGTH: 39
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (1)...(1)
<223> OTHER INFORMATION: 4-Imidazolylpropionyl
<220> FEATURE:
<221> NAME/KEY: MOD_RES
<222> LOCATION: (27)...(27)
<223> OTHER INFORMATION: Lys-NH(epsilon) octanoyl
<220> FEATURE:
<221> NAME/KEY: MOD_RES
<222> LOCATION: (39)...(39)
<223> OTHER INFORMATION: AMIDATION

<400> SEQUENCE: 139

```
Xaa Gly Glu Gly Thr Phe Thr Ser Asp Leu Ser Lys Gln Met Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
            35

<210> SEQ ID NO 140
<211> LENGTH: 39
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (1)...(1)
<223> OTHER INFORMATION: 4-Imidazolylpropionyl
<220> FEATURE:
<221> NAME/KEY: MOD_RES
<222> LOCATION: (27)...(27)
<223> OTHER INFORMATION: Lys-NH(epsilon) octanoyl
<220> FEATURE:
<221> NAME/KEY: MOD-RES
<222> LOCATION: (39)...(39)
<223> OTHER INFORMATION: AMIDATION

<400> SEQUENCE: 140

Xaa Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala Pro Pro Pro Ser
            35

<210> SEQ ID NO 141
<211> LENGTH: 39
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
<222> LOCATION: (1)...(1)
<223> OTHER INFORMATION: 4-Imidazolylpropionyl
<220> FEATURE:
<221> NAME/KEY: MOD_RES
<222> LOCATION: (28)...(28)
<223> OTHER INFORMATION: Lys-NH(epsilon) octanoyl
<220> FEATURE:
<221> NAME/KEY: MOD-RES
<222> LOCATION: (39)...(39)
<223> OTHER INFORMATION: AMIDATION

<400> SEQUENCE: 141

Xaa Gly Glu Gly Thr Phe Thr Ser Asp Leu Ser Lys Gln Met Glu
1               5                   10                  15

Glu Ala Val Arg Leu Phe Ile Glu Trp Leu Asn Lys Gly Gly Pro Ser
            20                  25                  30

Ser Gly Ala Pro Pro Pro Ser
            35

<210> SEQ ID NO 142
<211> LENGTH: 39
<212> TYPE: PRT
<213> ORGANISM: Artificial Sequence
<220> FEATURE:
<223> OTHER INFORMATION: synthetic peptide construct
<220> FEATURE:
<221> NAME/KEY: MOD_RES
```

```
<222> LOCATION: (1)...(1)
<223> OTHER INFORMATION: 4-Imidazolylpropionyl
<220> FEATURE:
<221> NAME/KEY: MOD_RES
<222> LOCATION: (28)...(28)
<223> OTHER INFORMATION: Lys-NH(epsilon) octanoyl
<220> FEATURE:
<221> NAME/KEY: MOD-RES
<222> LOCATION: (39)...(39)
<223> OTHER INFORMATION: AMIDATION

<400> SEQUENCE: 142

Xaa Gly Glu Gly Thr Phe Thr Ser Asp Leu Ser Lys Gln Leu Glu Glu
1               5                   10                  15

Glu Ala Val Arg Leu Phe Ile Glu Phe Leu Asn Lys Gly Gly Pro Ser
            20                  25                  30

Ser Gly Ala Pro Pro Pro Ser
            35
```